(12) United States Patent
Park et al.

(10) Patent No.: US 10,249,824 B2
(45) Date of Patent: Apr. 2, 2019

(54) CONDENSED-CYCLIC COMPOUND AND ORGANIC LIGHT-EMITTING DIODE COMPRISING THE SAME

(71) Applicant: Samsung Display Co. Ltd., Yongin-si, Gyeonggi-do (KR)

(72) Inventors: Bum-Woo Park, Yongin-si (KR); Yoon-Hyun Kwak, Yongin-si (KR); Sun-Young Lee, Yongin-si (KR); Se-Jin Cho, Yongin-si (KR)

(73) Assignee: Samsung Display Co., Ltd., Yongin-si (KR)

(*) Notice: Subject to any disclaimer, the term of this patent is extended or adjusted under 35 U.S.C. 154(b) by 863 days.

(21) Appl. No.: 13/686,909

(22) Filed: Nov. 27, 2012

(65) Prior Publication Data
US 2013/0292653 A1    Nov. 7, 2013

(30) Foreign Application Priority Data

May 3, 2012   (KR) .................. 10-2012-0047120

(51) Int. Cl.
| H01L 51/00 | (2006.01) |
| C07D 221/08 | (2006.01) |
| C07D 401/04 | (2006.01) |
| C07D 417/14 | (2006.01) |
| C07D 471/04 | (2006.01) |
| C07D 491/04 | (2006.01) |
| C07D 495/04 | (2006.01) |
| C07D 401/14 | (2006.01) |

(52) U.S. Cl.
CPC ........ H01L 51/0054 (2013.01); C07D 221/08 (2013.01); C07D 401/04 (2013.01); C07D 401/14 (2013.01); C07D 417/14 (2013.01); C07D 471/04 (2013.01); C07D 491/04 (2013.01); C07D 495/04 (2013.01)

(58) Field of Classification Search
CPC .. C07D 221/08; C07D 401/04; C07D 401/14; C07D 417/14; C07D 471/04; C07D 491/04; C07D 495/04; H01L 51/0054
See application file for complete search history.

(56) References Cited

U.S. PATENT DOCUMENTS

| 4,018,780 A | * | 4/1977 | Lappi | ................. | C07D 333/76 |
| | | | | | 546/62 |
| 4,060,527 A | * | 11/1977 | Nakamoto | ......... | C07D 219/08 |
| | | | | | 546/102 |
| 5,077,142 A | * | 12/1991 | Sakon | ................. | C09K 11/06 |
| | | | | | 313/504 |
| 5,589,326 A | * | 12/1996 | Deng | ................. | C07F 15/0026 |
| | | | | | 435/14 |
| 5,635,308 A | | 6/1997 | Inoue et al. | | |
| 5,645,948 A | | 7/1997 | Shi et al. | | |
| 5,972,247 A | | 10/1999 | Shi et al. | | |
| 6,465,115 B2 | | 10/2002 | Shi et al. | | |
| 6,596,415 B2 | | 7/2003 | Shi et al. | | |
| 6,696,177 B1 | * | 2/2004 | Hatwar | ................. | C09K 11/06 |
| | | | | | 257/88 |
| 6,830,833 B2 | | 12/2004 | Li | | |
| 8,389,132 B2 | * | 3/2013 | Seo | ..................... | C07F 15/0033 |
| | | | | | 257/E51.044 |
| 8,569,751 B2 | * | 10/2013 | Horiuchi | ............. | C07D 471/04 |
| | | | | | 257/40 |
| 8,686,139 B2 | | 4/2014 | Lux et al. | | |
| 9,062,054 B2 | * | 6/2015 | Clement | ............. | C07D 471/14 |
| 9,318,707 B2 | * | 4/2016 | Hattori | ................ | H01L 51/0043 |
| 9,416,107 B2 | * | 8/2016 | Lee | ....................... | C07D 401/14 |
| 2004/0076853 A1 | * | 4/2004 | Jarikov | .................. | C09K 11/06 |
| | | | | | 428/690 |
| 2006/0097227 A1 | | 5/2006 | Okajima et al. | | |
| 2010/0187510 A1 | | 7/2010 | Rostovtsev | | |
| 2010/0207108 A1 | | 8/2010 | Herron et al. | | |
| 2011/0156017 A1 | | 6/2011 | Lee et al. | | |
| 2011/0266526 A1 | * | 11/2011 | Ma | ......................... | C09K 11/06 |
| | | | | | 257/40 |
| 2012/0217485 A1 | | 8/2012 | Lee et al. | | |

(Continued)

FOREIGN PATENT DOCUMENTS

| EP | 2072517 A1 | 6/2009 |
| EP | 2 436 679 A1 | 4/2012 |
| JP | 8-12600 | 1/1996 |

(Continued)

OTHER PUBLICATIONS

C.P. Buu-Hoi, 76B Berichte der Deutschen Chemischen Gesellschaft [Abteilung] B: Abhandlungen, 1269-1274 (1943).*

(Continued)

*Primary Examiner* — Alexander R Pagano
(74) *Attorney, Agent, or Firm* — Lewis Roca Rothgerber Christie LLP

(57) ABSTRACT

Embodiments of the present invention are directed to a condensed-cyclic compound represented by Formula 1, and to an organic light-emitting diode including the same.

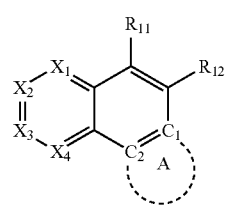

Formula 1

29 Claims, 1 Drawing Sheet

(56) References Cited

U.S. PATENT DOCUMENTS

| | | | | |
|---|---|---|---|---|
| 2012/0280613 A1* | 11/2012 | Kang | ............ | C09K 11/06 313/504 |
| 2014/0117331 A1* | 5/2014 | Kim | ............ | H01L 51/0067 257/40 |

FOREIGN PATENT DOCUMENTS

| | | | | |
|---|---|---|---|---|
| JP | 2000-003782 | | 1/2000 | |
| JP | 2004-055258 | | 2/2004 | |
| JP | 2004-182737 | | 7/2004 | |
| JP | 2004-311184 | | 11/2004 | |
| JP | 2006-241053 | | 9/2006 | |
| JP | 2010-027761 | | 2/2010 | |
| JP | 2010-045281 | | 2/2010 | |
| JP | WO 2011021545 A1 * | | 2/2011 | ........... C07D 471/04 |
| JP | 2011-46616 A | | 3/2011 | |
| JP | 2012-185241 A | | 9/2012 | |
| KR | 10-2010-0003624 A | | 1/2010 | |
| KR | 10-2010-0108924 | | 10/2010 | |
| KR | 10-2010-0111037 A | | 10/2010 | |
| KR | 10-2011-0047803 A | | 5/2011 | |
| KR | 10-2011-0058250 | | 6/2011 | |
| KR | 10-2012-0031771 A | | 4/2012 | |
| KR | 10-2012-0117693 | | 10/2012 | |
| KR | 2010111037 A * | | 10/2014 | |
| TW | 200934776 | | 8/2009 | |
| WO | WO 2009/083197 A2 | | 7/2009 | |
| WO | WO 2009/104733 A1 | | 8/2009 | |
| WO | WO 2010/075379 A2 | | 7/2010 | |
| WO | WO 2010/114264 A1 | | 10/2010 | |
| WO | WO 2011/024391 A1 | | 3/2011 | |
| WO | WO 2011/063927 A1 | | 6/2011 | |
| WO | WO 2011/126225 A1 | | 10/2011 | |
| WO | WO 2012/091225 A1 | | 7/2012 | |

OTHER PUBLICATIONS

F.G. Smith et al., 25 Analytical Chemistry, 510-511 (1953).*
R.F. Parcell et al., 28 Journal of Organic Chemistry, 3468-3473 (1963).*
B. Schaefer et al., 25 European Journal of Inorganic Chemistry, 4056-4063 (2007).*
S.L. Harbeson et al., Deuterium in Drug Discovery and Development, in 46 Annual Reports in Medicinal Chemistry, 403-417, 405 (2011).*
CAS Registry No. 856970-59-7 (1956).*
CAS Registry No. 856353-90-7 (1937).*
J. Dobson et al., Journal of the Chemical Society,150-155 (1946).*
E. Chelain et al., 115 Journal of the American Chemical Society, 10568-10580 (1993).*
P. J. Campos et al., 54 Tetrahedron, 6929-6938 (1998).*
Abstract of Park et al., KR 2010111037 (2010).*
A. Shafiee et al., 13 Journal of Heterocyclic Chemistry (1976).*
T. Koyama et al., 24 Chemical & Pharmaceutical Bulletin, 591-595 (1976).*
E.P. Burrows et al., 30 Journal of Mass Spectroscopy, 312-318, (1995).*
CAS Abstract Teuber, Chemische Berichte (1967).*
H.J. Teuber et al., 100 Chemische Berichte, 2077-2092 (1967).*
CAS Abstract of Nakamoto et al., U.S. Pat. No. 4,060,527 (1977).*
CAS Reg No. 132379-14-7 (1991).*
CAS Abstract and Indexed Compounds Adams (1944).*
CAS Abstract and Indexed Compounds Shafiee (1953).*
CAS Abstract and Indexed Compounds Minsenzhikov (1979).*
I. Alkorta et al., 21 Tetrahedron: Asymmetry, 962-968 (2010).*
R. Adams et al., 66 Journal of the American Chemical Society, 22-26 (1944).*
A. Shafiee et al., 13 Journal of Heterocyclic Chemistry, 141-144 (1976).*
Chelain, Evelyne et al., Reaction of Aminocarbene Complexes of Chromium with Alkynes. 2. Intramolecular Insertions Leading to Polycyclic Lactams, Journal of the American Chemical Society, 1993, pp. 10568-10580, vol. 115, American Chemical Society, United States.
Favaro, G. et al., Luminescence spectra and triplet lifetimes of neutral and protonated azaphenanthrenes, Spectrochimica Acts, 1971, pp. 915-921, vol. 27A, Pergamon Press, Northern Ireland.
Kethe, Anila et al., Ring closing and opening reactions leading to aza-polycyclic aromatic compounds, Tetrahedron, Mar. 3, 2012, pp. 3357-3360, vol. 68, Elsevier, DeKalb, IL, United States.
Li, Bin et al., Direct Cross-Coupling of C—H Bonds with Grignard Reagents through Cobalt Catalysis, Angewandte Chemie International, 2011, pp. 1109-1113, vol. 50, Wiley-VCH Verlag GmbH & Co. KGaA, Weinheim, Germany.
Li, Bing et al., One-pot synthesis of benzo[a]phenanthridin-5-ones by photoinduced cycloaddition of 3-chloroisoquinolin-1-ones with styrenes, Tetrahedron Letters, May 31, 2010, pp. 3748-3751, vol. 51, Elsevier, Lanzhou, China.
Mandadapu, Anil K. et al., Synthesis of 8-aryl substituted benzo[a]phenanthridine derivatives by consecutive three component tandem reaction and 6-endo carbocyclization, Tetrahedron, Jul. 23, 2012, pp. 8207-8215, vol. 68, Elsevier, Lucknow, India.
Partial European Search Report, dated Oct. 14, 2013 for European Patent Application No. 13165991.4, 9 pages.
Adachi, Chihaya et al., Confinement of Charge Carriers and Molecular Excitons Within 5-nm-Thick Emitter Layer in Organic Electroluminescent Devices With a Double Heterostructure, Aug. 6, 1990, pp. 531-533, Appl. Phys. Letter., vol. 57, No. 6.
Sakamoto, Youichi et al., Synthesis, Characterization, and Electron-Transport Property of Perfluorinated Phenylene Dendrimers, Feb. 15, 2000, pp. 1832-1833, American Chemical Society, J. Am. Chem., Soc. 2000.
Tang, C.W. et al., Organic Electroluminescent Diodes, Sep. 21, 1987, pp. 913-915, Appl. Phys. Lett. 51 (12).
Yamaguchi, Shigehiro et al., Diphenylamino-Substituted 2,5-Diarylsiloles for Single-Layer Organic Electroluminescent Devices, Nov. 10, 2000; pp. 98-99, Chemistry Letters 2001, The Chemical Society of Japan.
EPO Search Report dated Mar. 6, 2014, for corresponding European Patent application 13165991.4, (20 pages).
Chelucci, G., et al, *Synthesis of stereodefined 1-aryl(heteroaryl) substituted 1,2-bis(2-bromopyridin-3-yl)ethenes by selective tandem Suzuki-Miyaura cross-coupling reactions*, ScienceDirect, Tetrahedron Letters, vol. 49, Mar. 2, 2008, pp. 2738-2742, XP22558373.
Schäfer, B., et al, *Synthesis and Properties of Tetrasubstituted 1,10-Phenanthrolines and Their Ruthenium Complexes*, Eur. J. Inorg. Chem., vol. 25, (2007), pp. 4056-4063, XP 2720339.
Cho, G., et al *Diimide nanoclusters play hole trapping and electron injections roles in organic light-emitting devices*, Nanoscale, vol. 3, (2011), pp. 1073-1077, XP 2720340.
Lee, H., et al, Phenanthroline diimide as an organic electron-injecting material for organic light-emitting devices, The Royal Society of Chemistry, vol. 2, Jul. 26, 2012, pp. 8762-8767, XP 2720341.
KIPO Office action dated Nov. 5, 2015, for Korean priority Patent application 10-2012-0047120, (19 pages).
English Abstract, and English machine translation of claims only for Japanese Publication 2004-055258 dated Feb. 19, 2004, listed above, (3 pages).
SIPO Office action dated May 26, 2016, for corresponding Chinese Patent application 201310160697.4, (6 pages).
KIPO Office action dated May 24, 2016, for Korean priority Patent application 10-2012-0047120, (9 pages).
Chemical Dictionary 7, reduced version, Kyoritsu Publishing Co., Ltd., p. 676.

* cited by examiner

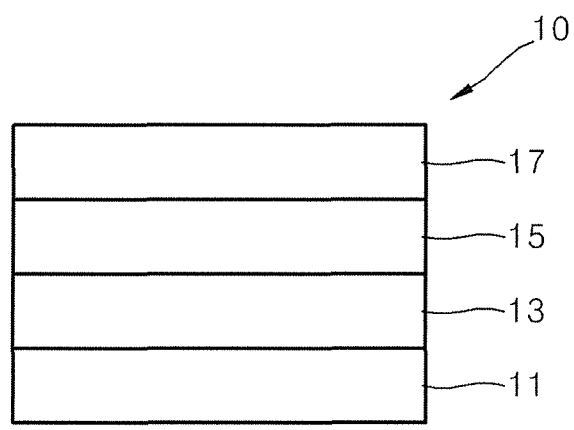

CONDENSED-CYCLIC COMPOUND AND ORGANIC LIGHT-EMITTING DIODE COMPRISING THE SAME

CROSS-REFERENCE TO RELATED PATENT APPLICATION

This application claims priority to and the benefit of Korean Patent Application No. 10-2012-0047120, filed on May 3, 2012 in the Korean Intellectual Property Office, the entire content of which is incorporated herein by reference.

BACKGROUND

1. Technical Field

The present invention relates to condensed-cyclic compounds and organic light-emitting diodes including the same.

2. Description of the Related Art

Organic light-emitting diodes (OLEDs) are self-emitting devices having wide viewing angles, good contrast, quick response speeds, high brightness, and good driving voltage characteristics. Also, OLEDs can provide multicolored images.

In general, the structure of an organic light-emitting diode includes a substrate on which is stacked (in sequential order) an anode, a hole transport layer (HTL), an emission layer (EML), an electron transport layer (ETL), and a cathode. Typically, the HTL, the EML, and the ETL are organic thin films formed of organic compounds.

The operating principle of an organic light-emitting diode having the above-described structure is as follows. A voltage is applied between the anode and the cathode, thereby causing holes injected from the anode to move to the EML via the HTL, and causing electrons injected from the cathode to move to the EML via the ETL. These carriers (i.e., the holes and electrons) recombine in the EML to generate excitons. When the excitons drop from an excited state to a ground state, light is emitted.

SUMMARY

Embodiments of the present invention are directed to condensed-cyclic compounds and to organic light-emitting diodes including the condensed-cyclic compounds.

According to embodiments of the present invention, a condensed-cyclic compound is represented by Formula 1 below:

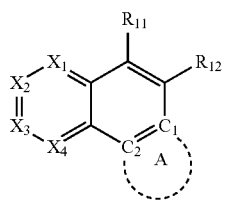

Formula 1

In Formula 1, $X_1$ is N or $C(R_1)$. $X_2$ is N or $C(R_2)$. $X_3$ is N or $C(R_3)$. $X_4$ is N or $C(R_4)$. At least one of $X_1$ to $X_4$ is N.

Additionally, ring A is a substituted or unsubstituted benzene, a substituted or unsubstituted naphthalene, a substituted or unsubstituted pyridine, a substituted or unsubstituted pyridazine, a substituted or unsubstituted pyrimidine, a substituted or unsubstituted pyrazine, a substituted or unsubstituted triazine, a substituted or unsubstituted quinoline, a substituted or unsubstituted isoquinoline, a substituted or unsubstituted phthalazine, a substituted or unsubstituted naphthyridine, a substituted or unsubstituted quinoxaline, a substituted or unsubstituted quinazoline, a substituted or unsubstituted cinnoline, a substituted or unsubstituted benzothiophene, a substituted or unsubstituted benzofuran, a substituted or unsubstituted dibenzothiophene, or a substituted or unsubstituted dibenzofuran.

Each of $R_1$ to $R_4$, $R_{11}$ and $R_{12}$ is independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, $-Si(R_{31})(R_{32})(R_{33})$, or $-N(R_{34})(R_{35})$.

Each of $R_{31}$ to $R_{35}$ is independently a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group.

According to embodiments of the present invention, an organic light-emitting diode includes a first electrode; a second electrode facing the first electrode; and an organic layer between the first electrode and the second electrode. The organic layer includes at least one of the condensed-cyclic compounds.

BRIEF DESCRIPTION OF THE DRAWINGS

The above and other features and advantages of the present invention will be better understood by reference to the following detailed description when considered in conjunction with the attached drawing, in which:

FIG. 1 is a schematic cross-sectional view of an organic light-emitting diode according to an embodiment of the present invention.

DETAILED DESCRIPTION OF THE INVENTION

Hereinafter, the present invention will be described more fully with reference to the accompanying drawings, in which exemplary embodiments of the invention are shown. As used herein, the term "and/or" includes any and all combinations of one or more of the associated listed items. Expressions such as "at least one of," when preceding a list of elements, modify the entire list of elements and do not modify the individual elements of the list.

A condensed-cyclic compound according to an embodiment of the present invention is represented by Formula 1 below.

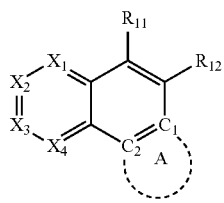

Formula 1

In Formula 1, "$C_1$" and "$C_2$" indicate the positions of those carbon atoms.

In Formula 1, $X_1$ is N or $C(R_1)$. $X_2$ is N or $C(R_2)$. $X_3$ is N or $C(R_3)$. $X_4$ is N or $C(R_4)$. At least one of $X_1$ to $X_4$ is N. In some embodiments, one or two of $X_1$ to $X_4$ may be N.

For example, in Formula 1, $X_1$ may be $C(R_1)$, $X_2$ may be $C(R_2)$, $X_3$ may be $C(R_3)$, and $X_4$ may be N. Alternatively, in Formula 1, $X_1$ may be N, $X_2$ may be $C(R_2)$, $X_3$ may be $C(R_3)$, and $X_4$ may be $C(R_4)$.

In Formula 1, each of $R_1$ to $R_4$, $R_{11}$, and $R_{12}$ may be independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —$Si(R_{31})(R_{32})(R_{33})$, or —$N(R_{34})(R_{35})$. Each of $R_{31}$ to $R_{35}$ is independently a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group. Here, in Formula 1, compounds in which both of $R_{11}$ and $R_{12}$ are hydrogen are excluded.

For example, in Formula 1, each of $R_1$ to $R_4$ may be independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{10}$ alkyl group, a substituted or unsubstituted $C_1$-$C_{10}$ alkoxy group, a substituted or unsubstituted $C_6$-$C_{14}$ aryl group, or a substituted or unsubstituted $C_2$-$C_{14}$ heteroaryl group.

Particularly, in Formula 1, each of $R_1$ to $R_4$ may be independently a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkyl group or a $C_1$-$C_{10}$ alkoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, or a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, or a chrysenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a fluoro-$C_1$-$C_{10}$ alkyl group, and a $C_1$-$C_{10}$ alkoxy group; an indolyl group; a benzoimidazolyl group; a carbazolyl group; an imidazolyl group; an imidazolinyl group; an imidazopyridinyl group; an imidazopyrimidinyl group; a pyridinyl group; a pyrimidinyl group; a triazinyl group; a quinolinyl group; or an indolyl group, a benzoimidazolyl group, a carbazolyl group, an imidazolyl group, an imidazolinyl group, an imidazopyridinyl group, an imidazopyrimidinyl group, a pyridinyl group, a pyrimidinyl group, a triazinyl group, or a quinolinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a fluoro-$C_1$-$C_{10}$ alkyl group, a $C_1$-$C_{10}$ alkoxy group, a phenyl group, or a naphthyl group.

According to an embodiment, in Formula 1, each of $R_1$ to $R_4$ may be independently a hydrogen atom, a deuterium atom, a halogen atom, a cyano group, a methyl group, an ethyl group, a propyl group, a butyl group, a pentyl group, a methoxy group, an ethoxy group, a propoxy group, a butoxy group, a pentoxy group, a phenyl group, or a naphthyl group, but $R_1$ to $R_4$ are not limited thereto.

In Formula 1, ring A may be a substituted or unsubstituted benzene, a substituted or unsubstituted naphthalene, a substituted or unsubstituted pyridine, a substituted or unsubstituted pyridazine, a substituted or unsubstituted pyrimidine, a substituted or unsubstituted pyrazine, a substituted or unsubstituted triazine, a substituted or unsubstituted quinoline, a substituted or unsubstituted isoquinoline, a substituted or unsubstituted phthalazine, a substituted or unsubstituted naphthyridine, a substituted or unsubstituted quinoxaline, a substituted or unsubstituted quinazoline, a substituted or unsubstituted cinnoline, a substituted or unsubstituted benzothiophene, a substituted or unsubstituted benzofuran, a substituted or unsubstituted dibenzothiophene, or a substituted or unsubstituted dibenzofuran.

For example, in Formula 1, ring A may be a substituted or unsubstituted benzene, a substituted or unsubstituted naphthalene, a substituted or unsubstituted pyridine, a substituted or unsubstituted pyrimidine, a substituted or unsubstituted quinoline, a substituted or unsubstituted isoquinoline, a substituted or unsubstituted benzothiophene, a substituted or unsubstituted benzofuran, a substituted or unsubstituted dibenzothiophene, or a substituted or unsubstituted dibenzofuran.

For example, in Formula 1, ring A may be a substituted or unsubstituted benzothiophene, a substituted or unsubstituted benzofuran, a substituted or unsubstituted dibenzothiophene, or a substituted or unsubstituted dibenzofuran. In this regard, the compound represented by Formula 1 may be used as a dopant of an EML of an organic light-emitting diode.

In Formula 1, ring A may also be a substituted or unsubstituted benzene, a substituted or unsubstituted pyridine, a substituted or unsubstituted pyrimidine, a substituted or unsubstituted quinoline, or a substituted or unsubstituted isoquinoline. In this regard, the compound of Formula 1 may be used as a host of an EML of an organic light-emitting diode.

According to an embodiment of the present invention, ring A of Formula 1 may be one of Formulae 2A to 2I below.

Formula 2A
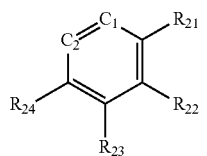

Formula 2B
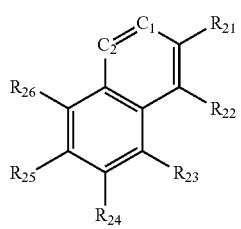

Formula 2C
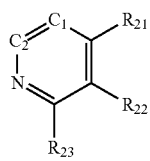

Formula 2D
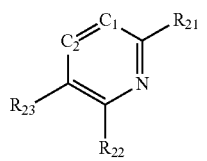

Formula 2E
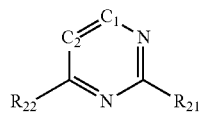

Formula 2F
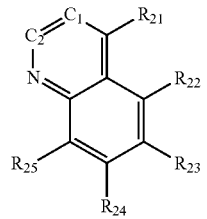

Formula 2G
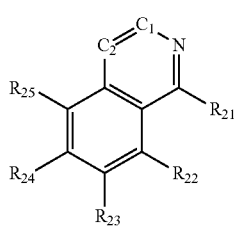

Formula 2H
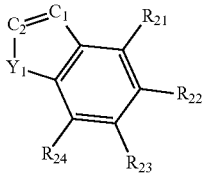

Formula 2I
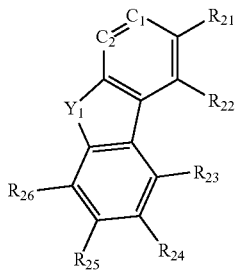

For example, in Formula 1, ring A may be represented by Formula 2A, 2C, 2F, 2I, or 2H, but ring A is not limited thereto.

For example, ring A of Formula 1 may be represented by Formula 2H or 2I, but ring A is not limited thereto. The compound of Formula 1 may be used as a dopant of an EML of an organic light-emitting diode.

For example, ring A of Formula 1 may be represented by Formula 2A, 2C, or 2F, but ring A is not limited thereto. The compound of Formula 1 may be used as a host of an EML of an organic light-emitting diode.

In Formulae 2A to 2I, each of $R_{21}$ to $R_{26}$ may be independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, or a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group. $Y_1$ may be S or O.

For example, in Formulae 2A to 2I, each of $R_{21}$ to $R_{26}$ may be independently a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkyl group or a $C_1$-$C_{10}$ alkoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, or a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, or a chrysenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, or a $C_1$-$C_{10}$ alkoxy group; an indolyl group; a benzoimidazolyl group; a carbazolyl group; an imidazolyl group; an imidazolinyl group; an imidazopyridinyl group; an imidazopyrimidinyl group; a pyridinyl group; a pyrimidinyl group; a triazinyl group; a quinolinyl group; or an indolyl group, a benzoimidazolyl group, a carbazolyl group, an imidazolyl group, an imidazolinyl group, an imidazopyridinyl group, an imidazopyrimidinyl group, a pyridinyl group, a pyrimidinyl group, a triazinyl group, or a quinolinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, or a naphthyl group, but $R_{21}$ to $R_{26}$ are not limited thereto.

According to an embodiment, in Formulae 2A to 2I, each of $R_{21}$ to $R_{26}$ may be hydrogen, but $R_{21}$ to $R_{26}$ are not limited thereto.

In Formula 1, each of $R_{11}$ and $R_{12}$ may be independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ alkoxy group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentacenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted indolyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzofuranyl group, a substituted or unsubstituted triazinyl group, or a substituted or unsubstituted oxadiazolyl group.

For example, each of $R_{11}$ and $R_{12}$ may be independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted phenyl group, a substituted or unsubstituted naphthyl group, a substituted or unsubstituted fluorenyl group, a substituted or unsubstituted phenanthrenyl group, a substituted or unsubstituted anthryl group, a substituted or unsubstituted pyrenyl group, a substituted or unsubstituted pyridinyl group, a substituted or unsubstituted indolyl group, a substituted or unsubstituted carbazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted benzothiophenyl group, a substituted or unsubstituted dibenzothiophenyl group, a substituted or unsubstituted dibenzofuranyl group, or a substituted or unsubstituted triazinyl group.

According to an embodiment, each of $R_{11}$ and $R_{12}$ may be independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{10}$ alkyl group, a substituted or unsubstituted $C_1$-$C_{10}$ alkoxy group, or one of Formulae 3A to 3P below.

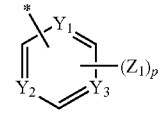

Formula 3A

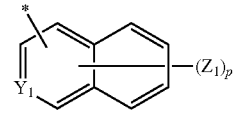

Formula 3B

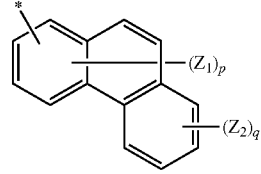

Formula 3C

In Formulae 3A to 3P, each of $Y_1$ to $Y_3$ is independently =N— or =C($Z_{11}$)—. $T_1$ is —S—, —O—, —N($Z_{12}$)—, or —C($Z_{13}$)($Z_{14}$)—. Each of $Z_1$ to $Z_3$ and $Z_{11}$ to $Z_{14}$ is independently a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ cycloalkyl group; a $C_6$-$C_{60}$ aryl group; a $C_6$-$C_{60}$ aryloxy group; a $C_6$-$C_{60}$ arylthio group; a $C_2$-$C_{60}$ heteroaryl group; a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_6$-$C_{60}$ aryl group, a $C_6$-$C_{60}$ aryloxy group, a $C_6$-$C_{60}$ arylthio group, or a $C_2$-$C_{60}$ heteroaryl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group; —N($Q_{11}$)($Q_{12}$); or —Si($Q_{13}$)($Q_{14}$)($Q_{15}$) where each of $Q_{11}$ to $Q_{15}$ is independently a $C_3$-$C_{60}$ cycloalkyl group; a $C_6$-$C_{60}$ aryl group; a $C_6$-$C_{60}$ aryloxy group; a $C_6$-$C_{60}$ arylthio group; a $C_2$-$C_{60}$ heteroaryl group; or a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_6$-$C_{60}$ aryl group, a $C_6$-$C_{60}$ aryloxy group, a $C_6$-$C_{60}$ arylthio group, or a $C_2$-$C_{60}$ heteroaryl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group.

Also, in Formulae 3A to 3P, p is an integer from 1 to 9, q is an integer from 1 to 4, and r is an integer from 1 to 3.

For example, each of $Z_1$ to $Z_3$ and $Z_{11}$ to $Z_{14}$ may be independently a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a methyl group; an ethyl group; a propyl group; a butyl group; a pentyl group; a methoxy group; an ethoxy group; a propoxy group; a butoxy group; a pentoxy group; a methyl group, an ethyl group, a propyl group, a butyl group, a pentyl group, a methoxy group, an ethoxy group, a propoxy group, a butoxy group, or a pentoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, or a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, phenanthrenyl group, an anthryl group, a pyrenyl group, or a chrysenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, a propyl group, a butyl group, a pentyl group, a methoxy group, an ethoxy group, a propoxy group, a butoxy group, or a pentoxy group; a carbazolyl group; an imidazolyl group; an imidazolinyl group; an imidazopyridinyl group; an imidazopyrimidinyl group; a pyridinyl group; a pyrimidinyl group; a triazinyl group; a quinolinyl group; a carbazolyl group, an imidazolyl group, an imidazolinyl group, an imidazopyridinyl group, an imidazopyrimidinyl group, a pyridinyl group, a pyrimidinyl group, a triazinyl group, or a quinolinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, a propyl group, a butyl group, a pentyl group, a methoxy group, an ethoxy group, a propoxy group, a butoxy group, or a pentoxy group; or —N($Q_{11}$)($Q_{12}$) where each of $Q_{11}$ and $Q_{12}$ is independently a phenyl group; a naphthyl group; a fluorenyl group; a phenanthrenyl group; an anthryl group; a pyrenyl group; a chrysenyl group; or a phenyl group, a naphthyl group, a fluorenyl group, a phenanthrenyl group, an anthryl group, a pyrenyl group, or a chrysenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, a propyl group, a butyl group, a pentyl group, a methoxy group, an ethoxy group, a propoxy group, a butoxy group, or a pentoxy group.

According to an embodiment, in Formula 1, each of $R_{11}$ and $R_{12}$ may be independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, or any one of Formulae 4-1 to 4-49 below:

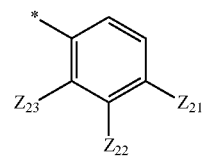

Formula 4-1

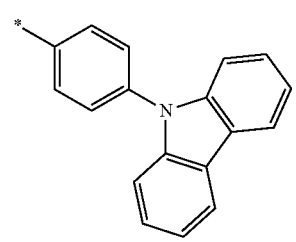

Formula 4-2

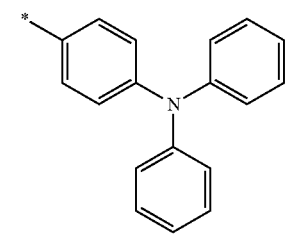

Formula 4-3

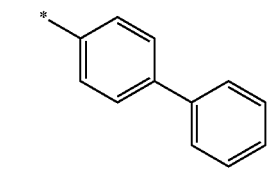

Formula 4-4

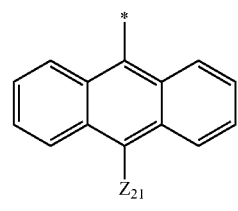

Formula 4-5

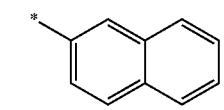

Formula 4-6

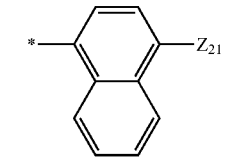

Formula 4-7

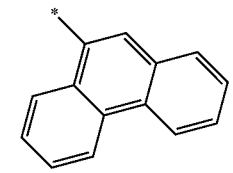

Formula 4-8

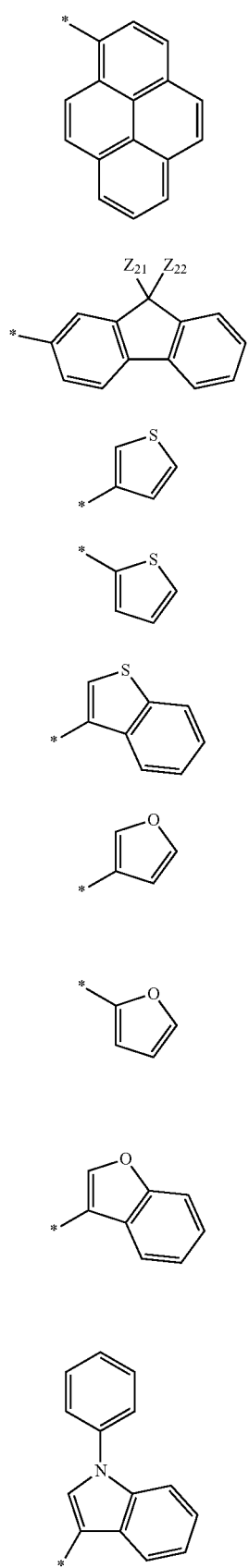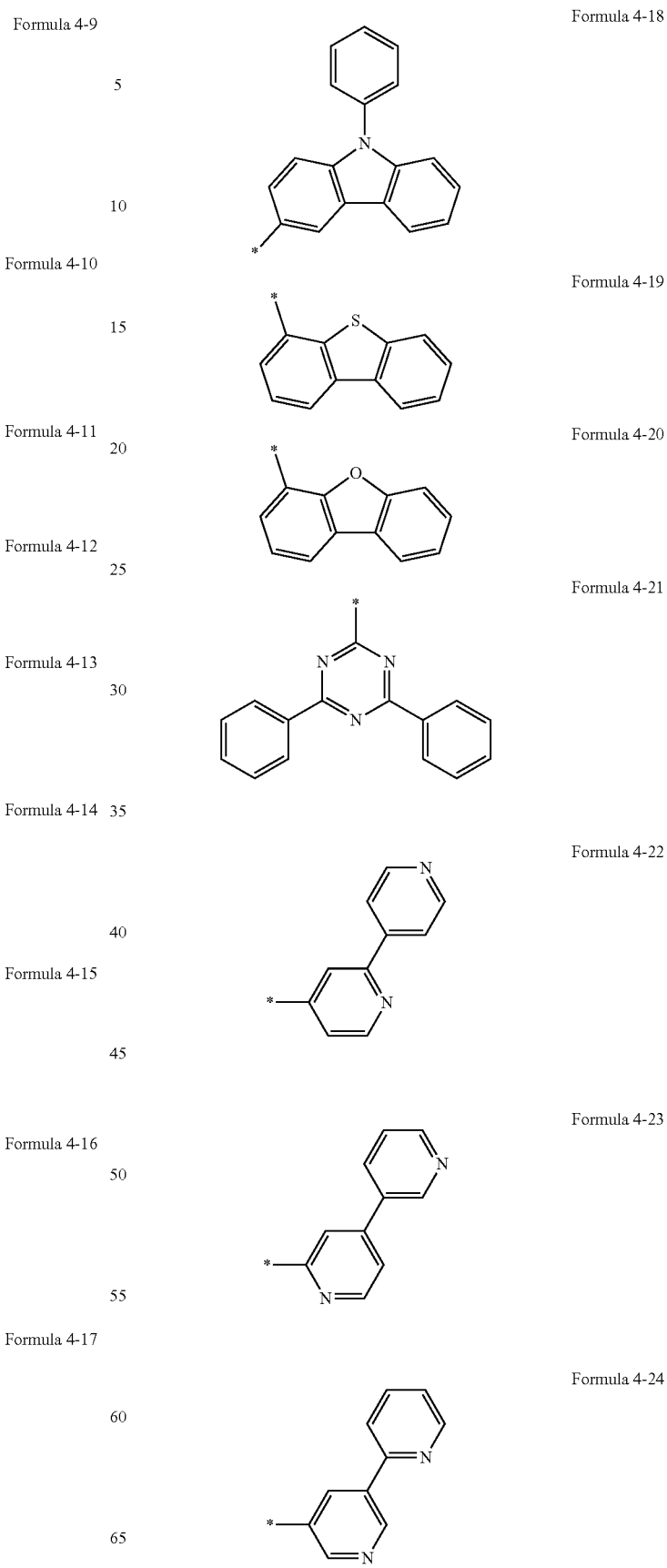

-continued
Formula 4-25
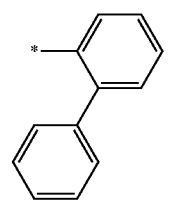
Formula 4-26
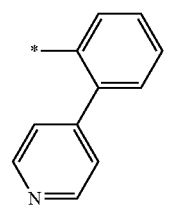
Formula 4-27
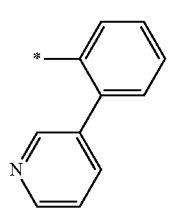
Formula 4-28
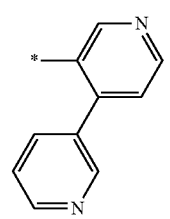
Formula 4-29
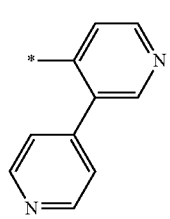
Formula 4-30
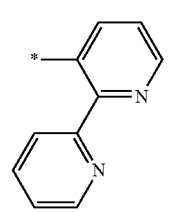
Formula 4-31
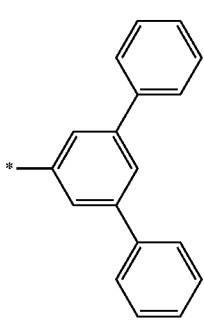
-continued
Formula 4-32
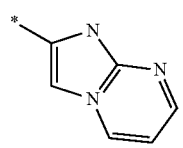
Formula 4-33
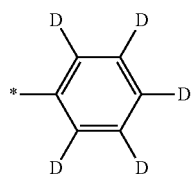
Formula 4-34
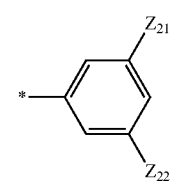
Formula 4-35
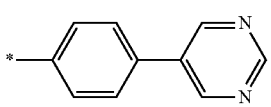
Formula 4-36
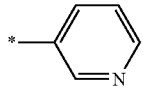
Formula 4-37
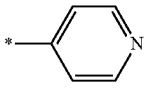
Formula 4-38
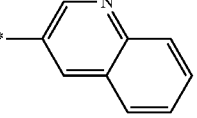
Formula 4-39
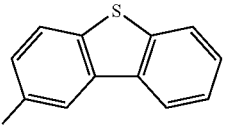
Formula 4-40
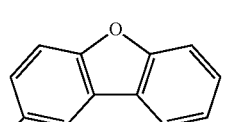
Formula 4-41
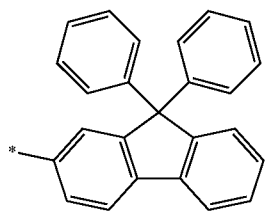

Formula 4-42

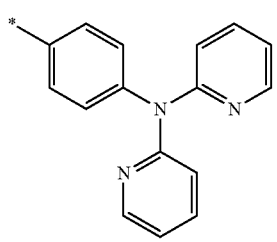

Formula 4-43

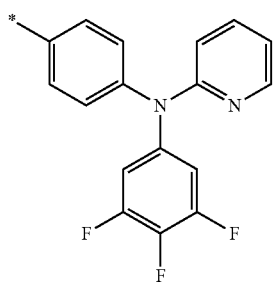

Formula 4-44

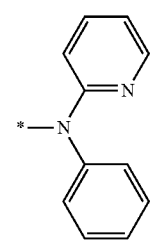

Formula 4-45

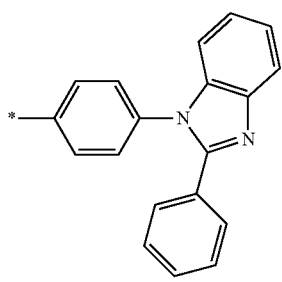

Formula 4-46

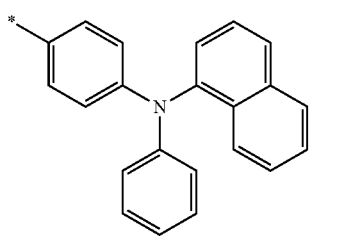

Formula 4-47

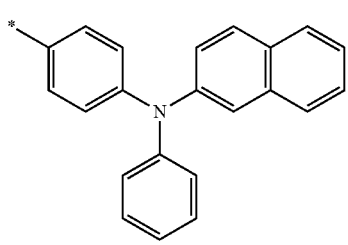

Formula 4-48

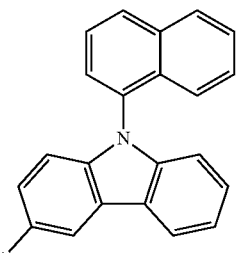

Formula 4-49

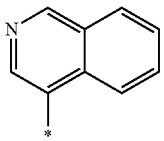

In Formulae 4-1 to 4-49, each of $Z_{21}$ to $Z_{23}$ may be independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, a propyl group, a butyl group, a pentyl group, a methoxy group, an ethoxy group, a propoxy group, a butoxy group, and a pentoxy group; or a methyl group, an ethyl group, a propyl group, a butyl group, a pentyl group, a methoxy group, an ethoxy group, a propoxy group, a butoxy group, or a pentoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, or a phosphoric acid group or a salt thereof, but $Z_{21}$ to $Z_{23}$ are not limited thereto.

The condensed-cyclic compound may be represented by one of Formulae 1A to 1E below.

Formula 1A

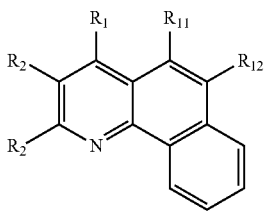

Formula 1B

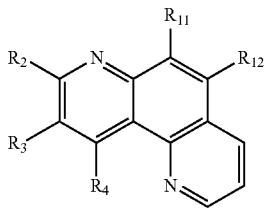

Formula 1C

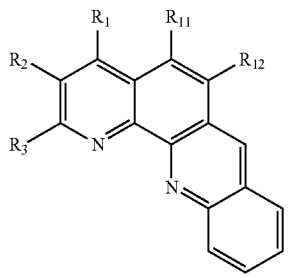

Formula 1D

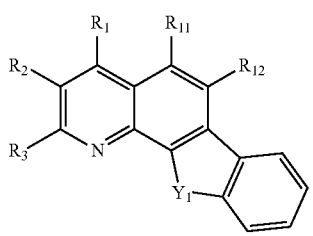

Formula 1E

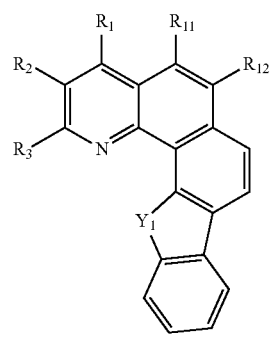

In Formulae 1A to 1E, $Y_1$, $R_1$ to $R_3$, $R_{11}$, and $R_{12}$ are as defined above.

For example, in Formulae 1A to 1E, compounds in which both of $R_{11}$ and $R_{12}$ are hydrogen are excluded.

For example, in Formulae 1A to 1E, each of $R_1$ to $R_4$ may be independently a hydrogen atom, a deuterium atom, a halogen atom, a cyano group, a methyl group, an ethyl group, a propyl group, a butyl group, a pentyl group, a methoxy group, an ethoxy group, a propoxy group, a butoxy group, a pentoxy group, a phenyl group or a naphthyl group, but $R_1$ to $R_4$ are not limited thereto. Each of $R_{11}$ and $R_{12}$ may be independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, or one of the compounds represented by Formulae 4-1 to 4-49, but $R_{11}$ and $R_{12}$ are not limited thereto.

The condensed-cyclic compound represented by Formula 1 may be any one of Compounds 1 to 25 below, but is not limited thereto.

1

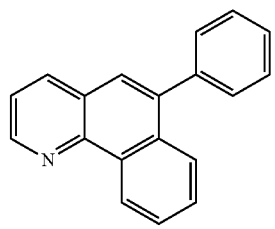

2

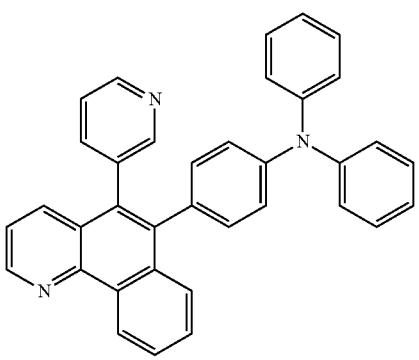

3

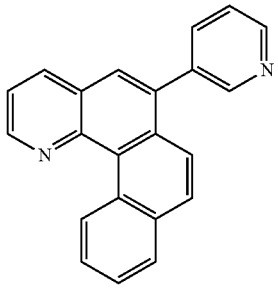

4

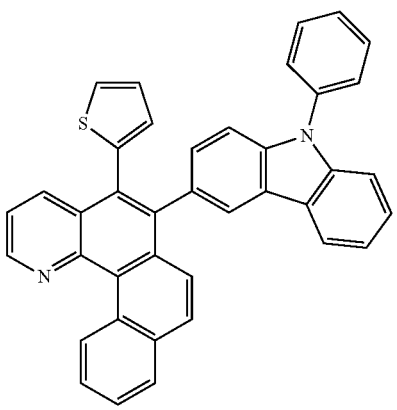

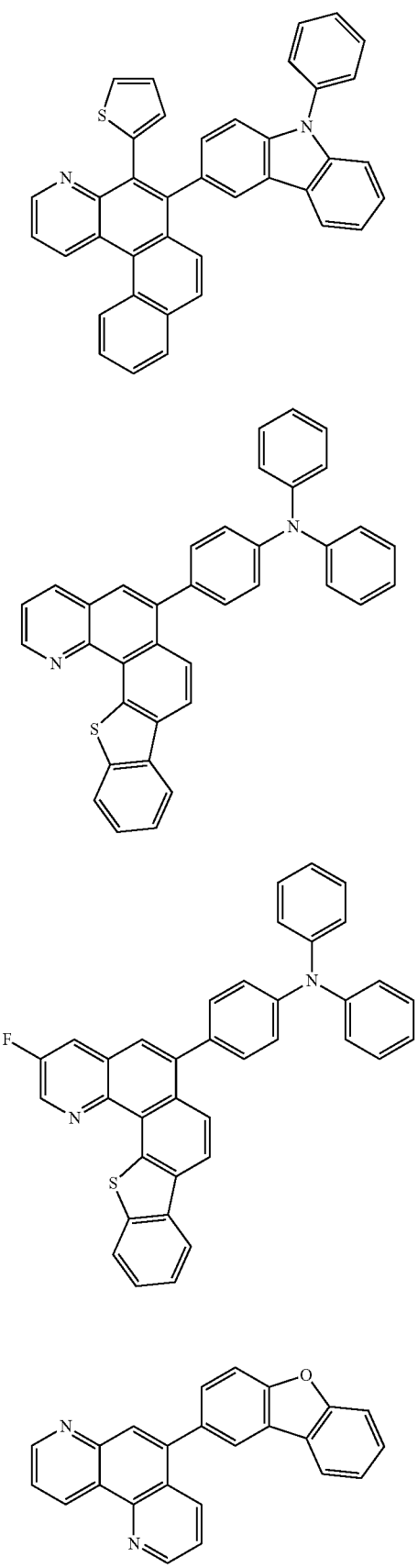
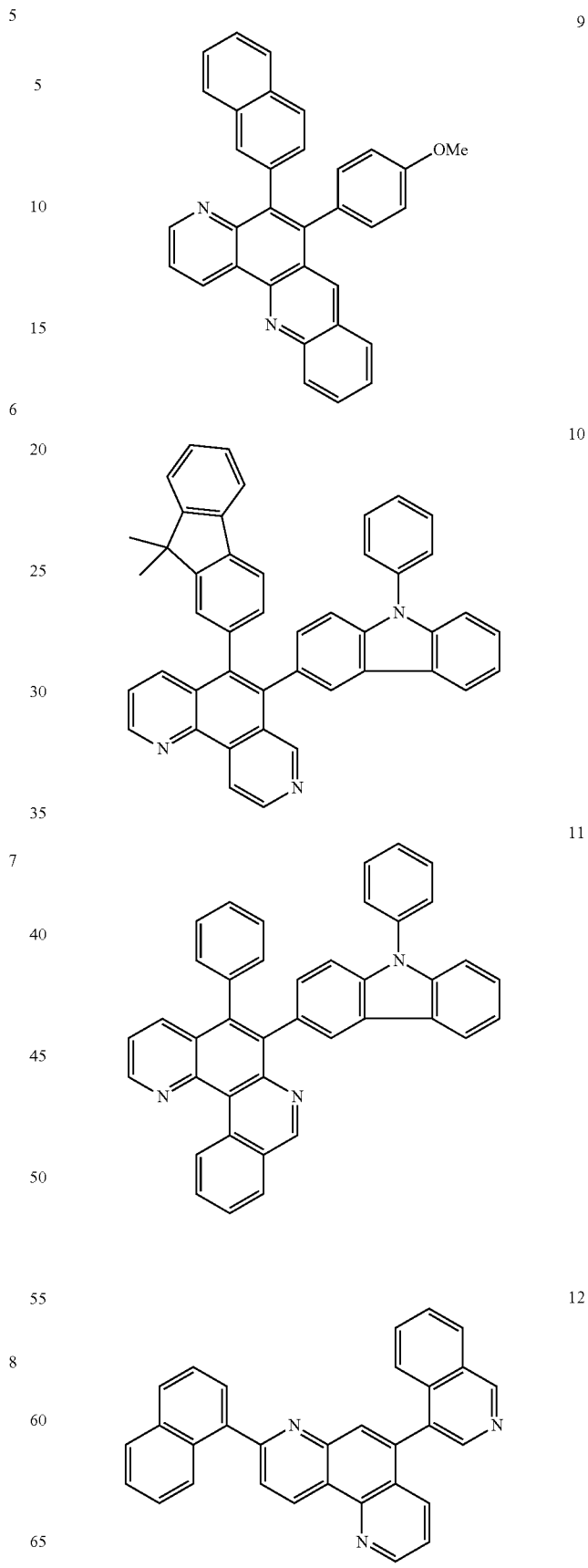

13
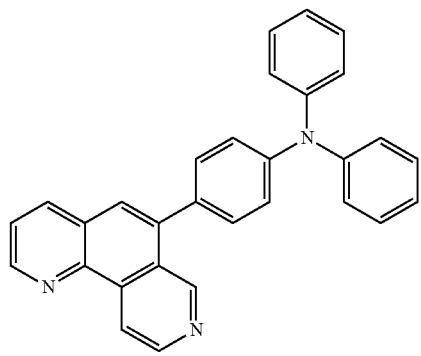
14
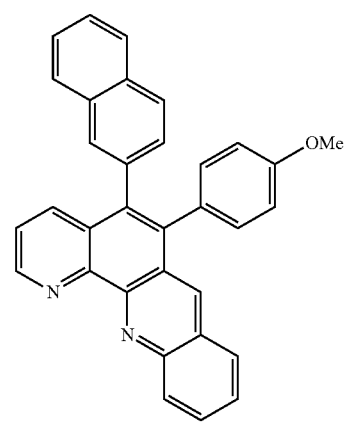
15
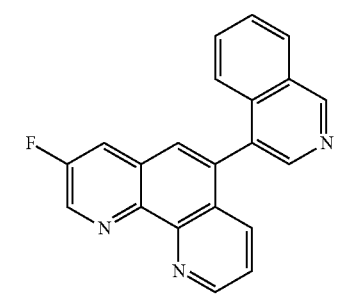
16
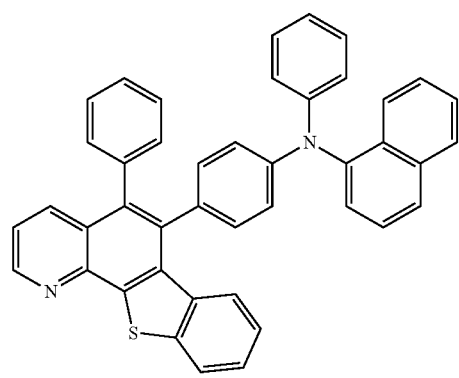
17
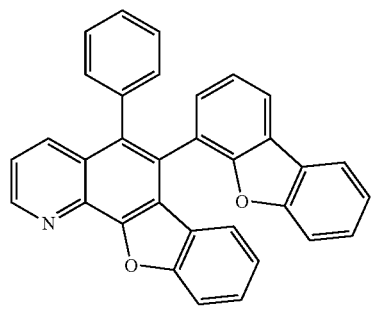
18
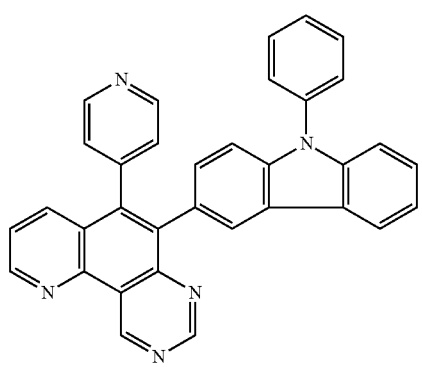
19
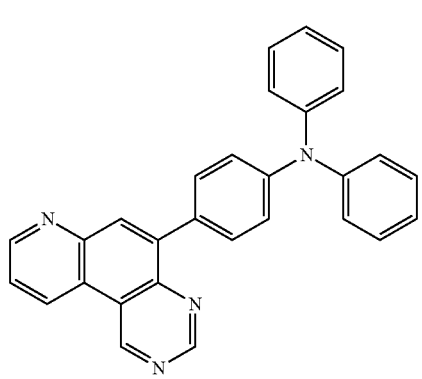
20
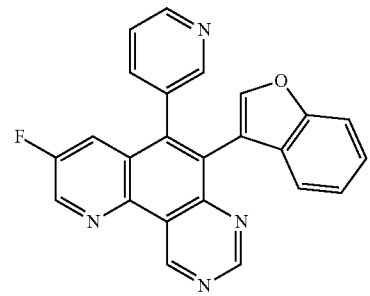

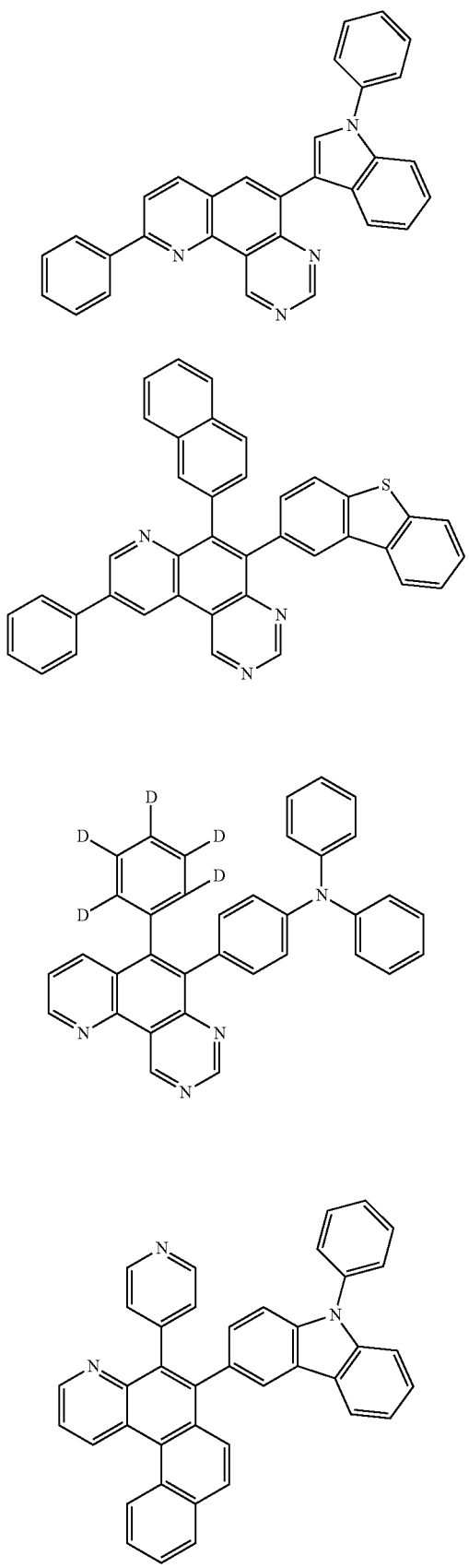
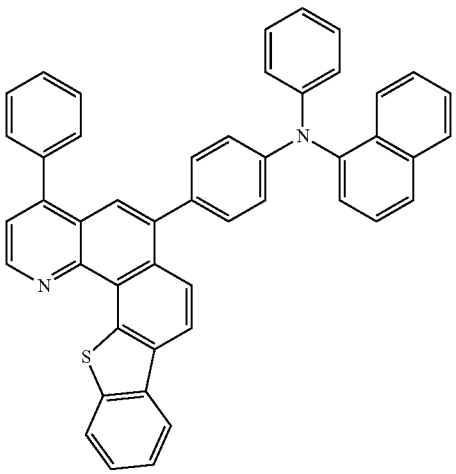

The condensed-cyclic compounds represented by Formula 1, as described above, includes a hetero ring, which gives the compounds a high glass transition temperature and/or melting point. Thus, when positioned between a pair of electrodes (e.g., an anode and cathode) of an organic light-emitting diode, the condensed-cyclic compounds may have good thermal resistance against Joule's heat generated in organic layers between the pair of electrodes, between the organic layers, or between the organic layer and the electrode during operation of the organic light-emitting diode.

The condensed-cyclic compounds represented by Formula 1 may be synthesized using known organic synthesis methods. Methods of synthesizing the condensed-cyclic compounds will be known or discernible to those of ordinary skill in the art without undue experimentation, especially with reference to the examples described below.

A condensed-cyclic compound of Formula 1 may be positioned between a pair of electrodes of an organic light-emitting diode. For example, the condensed-cyclic compound may be used in an EML and/or a layer between an EML and an anode (e.g., a hole injection layer (HIL), a hole transport layer (HTL), or a functional layer having both hole injecting and hole transporting capabilities).

According to another embodiment of the present invention, an organic light-emitting diode includes a first electrode, a second electrode facing the first electrode, and an organic layer between the first electrode and the second electrode. The organic layer includes at least one condensed-cyclic compound represented by Formula 1, as described above.

The phrase "[t]he organic layer includes at least one condensed-cyclic compound," as used herein, may be interpreted as either that the organic layer may include one condensed-cyclic compound represented by Formula 1, or that the organic layer includes at least two different condensed-cyclic compounds represented by Formula 1.

For example, the organic layer may include Compound 6 alone, as the condensed-cyclic compound. In this regard, Compound 6 may be present in the EML of the organic light-emitting diode. Alternatively, the organic layer may include Compound 6 and Compound 2, as the condensed-cyclic compounds. In this regard, Compound 6 and Compound 2 may be included in the same layer (for example, Compound 6 and Compound 2 may be included in the EML), or in different layers (for example, Compound 6 may be included in the EML and Compound 2 may be included in the ETL).

The organic layer may include at least one of an HIL, an HTL, a functional layer having both hole injecting and hole transporting capabilities (H-functional layer), a buffer layer, an electron blocking layer (EBL), an EML, a hole blocking layer (HBL), an electron transport layer (ETL), an electron injection layer (EIL), and/or a functional layer having both electron injecting and electron transporting capabilities (E-functional layer).

The term "organic layer," as used herein, refers to a single layer and/or multiple layers between the first and second electrodes of the organic light-emitting diode.

The organic layer may include an EML that includes the condensed-cyclic compound. Alternatively, the organic layer may include at least one of the HIL, the HTL, and the H-functional layer, and at least one of the HIL, the HTL, and the H-functional layer may include the condensed-cyclic compound.

The condensed-cyclic compound contained in the EML may be used as a fluorescent dopant. In this regard, the condensed-cyclic compound contained in the EML may be represented by Formula 1D or 1E, and the EML including the condensed-cyclic compound represented by Formula 1D or 1E may emit blue light.

The condensed-cyclic compound contained in the EML may be used as a phosphorescent dopant. In this regard, the condensed-cyclic compound contained in the EML may be represented by one of Formulae 1A to 1C, and the EML including the condensed-cyclic compound represented by one of Formulae 1A to 1C may emit green light.

FIG. 1 is a schematic sectional view of an organic light-emitting diode 10 according to an embodiment of the present invention. Hereinafter, the organic light-emitting diode 10 and a method of fabricating the organic light-emitting diode 10 will be described with reference to FIG. 1.

A substrate 11 may be any substrate commonly used in organic light-emitting diodes, and may be a glass substrate or a transparent plastic substrate with good mechanical strength, thermal stability, transparency, surface smoothness, ease of handling, and waterproofness.

A first electrode 13 may be formed on the substrate 11 by depositing or sputtering a material used to form the first electrode 13. When the first electrode 13 is an anode, the material used to form the first electrode 13 may be a material having a high work function so as to facilitate hole injection. The first electrode 13 may be a reflective electrode or a transmissive (i.e., transparent) electrode. Transparent and conductive materials such as indium tin oxide (ITO), indium zinc oxide (IZO), tin oxide ($SnO_2$), and zinc oxide (ZnO) may be used to form the first electrode 13. The first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode 13 may have a single-layered or a multi-layered structure. For example, the first electrode 13 may have a triple-layered structure of ITO/Ag/ITO, but the first electrode is not limited thereto.

The organic emission layer 15 is formed on the first electrode 13.

The organic layer 15 may include an HIL, an HTL, a buffer layer, an EML, an ETL, and an EIL.

The HIL may be formed on the first electrode 13 by vacuum deposition, spin coating, casting, Langmuir-Blodgett (LB) deposition, or the like.

When the HIL is formed using vacuum deposition, the deposition conditions may vary according to the compound used to form the HIL, and the structure and thermal characteristics of the HIL to be formed. For example, the deposition conditions may include a deposition temperature of 100 to 500° C., a vacuum pressure of $10^{-8}$ to $10^{-3}$ torr, and a deposition rate of about 0.01 to about 100 Å/sec, but the deposition conditions are not limited thereto.

When the HIL is formed using spin coating, the coating conditions may vary according to the compound used to form the HIL, and the structure and thermal characteristics of the HIL to be formed. For example, the coating conditions may include a coating speed of about 2000 rpm to about 5000 rpm, and a thermal treatment temperature of about 80° C. to about 200° C., where the thermal treatment removes the solvent after coating. However, the coating conditions are not limited thereto.

Any known hole injecting materials may be used to form the HIL. Nonlimiting examples of hole injecting materials include N,N'-diphenyl-N,N'-bis-[4-(phenyl-m-tolyl-amino)-phenyl]-biphenyl-4,4'-diamine (DNTPD), phthalocyanine compounds such as copperphthalocyanine, 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly (4-styrenesulfonate) (PEDOT/PSS), polyaniline/camphor sulfonic acid (Pani/CSA), and (polyaniline)/poly(4-styrene-sulfonate) (PANI/PSS).

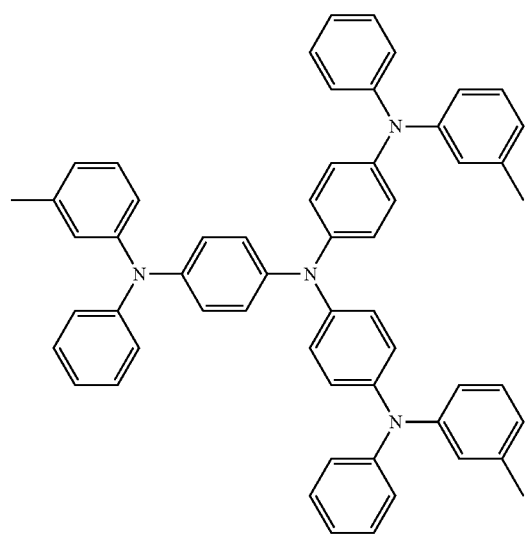

m-MTDATA

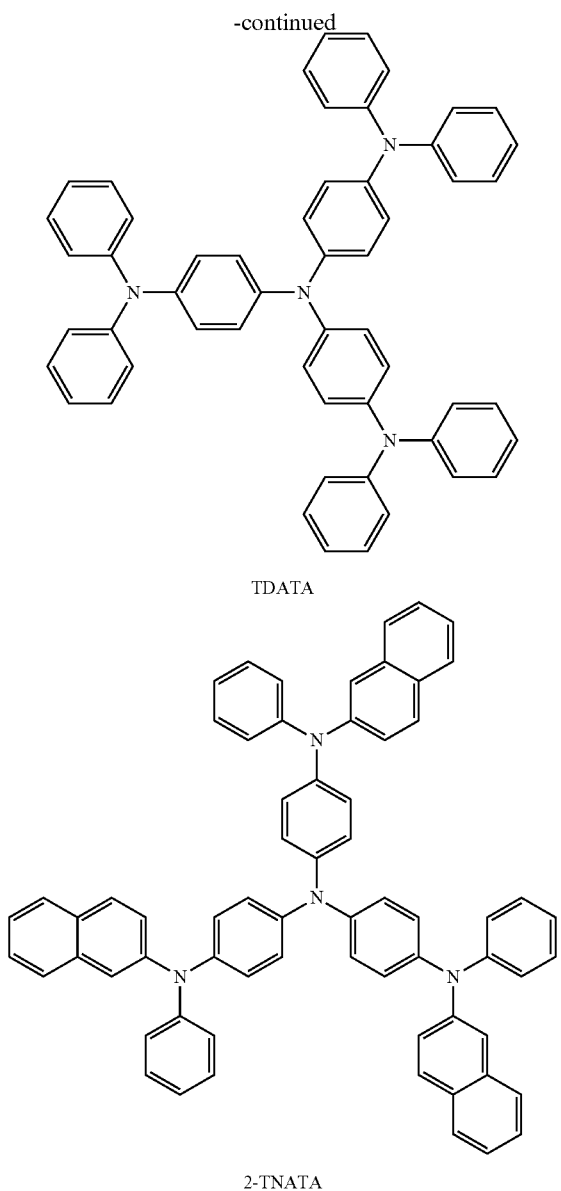

TDATA

2-TNATA

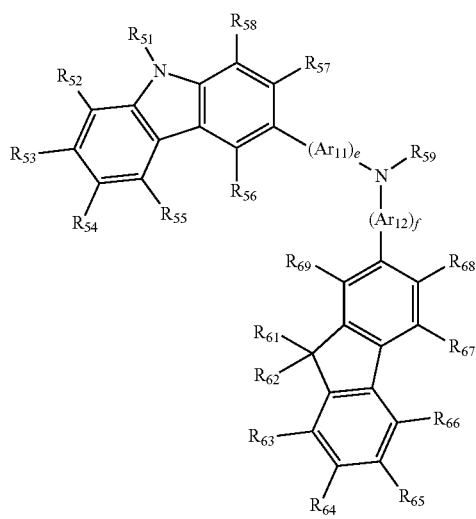

TPD

NPB

The thickness of the HTL may be about 50 to about 2,000 Å, for example, about 100 to about 1,500 Å. When the thickness of the HTL is within these ranges, the HTL may have good hole transporting ability without a substantial increase in driving voltage.

The H-functional layer may include at least one of the hole injecting materials and at least one of the hole transporting materials described above, and the thickness of the H-functional layer may be about 500 Å to about 10,000 Å, for example, about 100 Å to about 1,000 Å. When the thickness of the H-functional layer is within these ranges, the H-functional layer may have good hole injecting and transporting abilities without a substantial increase in driving voltage.

Also, at least one of the HIL, HTL, and the H-functional layer may include at least one of the compounds represented by Formulae 300 and 350 below.

Formula 300

The thickness of the HIL may be about 100 to about 10,000 Å, and for example, about 100 to about 1,000 Å. When the thickness of the HIL is within these ranges, the HIL may have good hole injecting ability without a substantial increase in driving voltage.

Then, the HTL may be formed on the HIL by vacuum deposition, spin coating, casting, LB deposition, or the like. When the HTL is formed by vacuum deposition or spin coating, the conditions for deposition and coating may be similar to those for the formation of the HIL, although the conditions for the deposition and coating may vary according to the material that is used to form the HTL.

Any known hole transporting materials may be used to form the HTL. Nonlimiting examples of hole transporting materials include carbazole derivatives such as N-phenylcarbazole and polyvinyl carbazole, N,N'-bis(3-methylphenyl)-N,N'-diphenyl-[1,1-biphenyl]-4,4'-diamine (TPD), 4,4',4''-tris(N-carbazolyl)triphenylamine (TCTA), and N,N'-di(1-naphthyl)-N,N'-diphenylbenzidine (NPB).

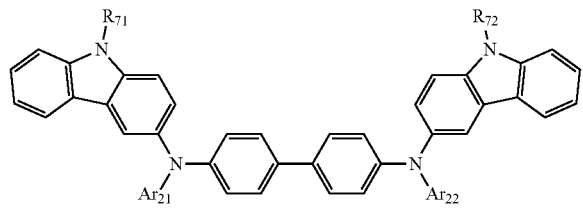

Formula 350

In Formula 300, each of $Ar_{11}$ and $Ar_{12}$ may be independently a substituted or unsubstituted $C_6$-$C_{60}$ arylene group or a substituted or unsubstituted $C_2$-$C_{60}$ heteroarylene group. For example, each of $Ar_{11}$ and $Ar_{12}$ may be independently a substituted or unsubstituted phenylene group, a substituted or unsubstituted naphthylene group, a substituted or unsubstituted phenanthrenylene group, a substituted or unsubstituted anthrylene group, a substituted or unsubstituted pyrenylene group, a substituted or unsubstituted chrysenylene group, a substituted or unsubstituted fluorenylene group, a substituted or unsubstituted carbazolylene group, a substituted or unsubstituted dibenzofuranylene group, or a substituted or unsubstituted dibenzothiophenylene group. In this regard, at least one substituent of the substituted phenylene group, the substituted naphthalene group, the substituted phenanthrenylene group, the substituted anthrylene group, the substituted pyrenylene group, the substituted chrysenylene group, the substituted fluorenylene group, the substituted carbazolylene group, the substituted dibenzofuranylene group, or the substituted dibenzothiophenylene group may be a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group; a $C_1$-$C_{10}$ alkoxy group; a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, or an indolyl group; or a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, or an indolyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, or a $C_1$-$C_{10}$ alkoxy group.

In Formula 350, each of $Ar_{21}$ and $Ar_{22}$ may be independently a substituted or unsubstituted $C_6$-$C_{60}$ aryl group or a substituted or unsubstituted $C_2$-$C_{60}$ heteroaryl group. For example, each of $Ar_{21}$ and $Ar_{22}$ may be independently a substituted or unsubstituted phenyl group, a substituted or unsubstituted naphthyl group, a substituted or unsubstituted phenanthrenyl group, a substituted or unsubstituted anthryl group, a substituted or unsubstituted pyrenyl group, a substituted or unsubstituted chrysenyl group, a substituted or unsubstituted fluorenyl group, a substituted or unsubstituted carbazolyl group, a substituted or unsubstituted dibenzofuranyl group, or a substituted or unsubstituted dibenzothiophenyl group. In this regard, at least one substituent of the substituted phenyl group, the substituted naphthyl group, the substituted phenanthrenyl group, the substituted anthryl group, the substituted pyrenyl group, the substituted chrysenyl group, the substituted fluorenyl group, the substituted carbazolyl group, the substituted dibenzofuranyl group, or the substituted dibenzothiophenyl group may be a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group; a $C_1$-$C_{10}$ alkoxy group; a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, or an indolyl group; or a phenyl group, a naphthyl group, a fluorenyl group, a phenanthrenyl group, an anthryl group, a triphenylenyl group, pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, or an indolyl group substituted with at least one selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, or a $C_1$-$C_{10}$ alkoxy group.

In Formula 300, each of e and f is independently an integer from 0 to 5, or 0, 1, or 2. For example, e may be 1, and f may be 0.

In Formulae 300 and 350, each of $R_{51}$ to $R_{58}$, $R_{61}$ to $R_{69}$, $R_{71}$, and $R_{72}$ may be independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_8$-$C_{80}$ aryl group, a substituted or unsubstituted $C_6$-$C_{60}$ aryloxy group, or a substituted or unsubstituted $C_6$-$C_{60}$ arylthio group. For example, each of $R_{51}$ to $R_{58}$, $R_{61}$ to $R_{69}$, $R_{71}$, and $R_{72}$ may be independently a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (e.g., a methyl group, an ethyl group, a propyl group, a butyl group, a pentyl group, or a hexyl group); a $C_1$-$C_{10}$ alkoxy group (e.g., a methoxy group, an ethoxy group, a propoxy group, a butoxy group, or a pentoxy group); a $C_1$-$C_{10}$ alkyl group or a $C_1$-$C_{10}$ alkoxy group substituted with at least one of a deuterium atom, a halogen atom, a hydroxyl group, a cyano group, a nitro group, an amino group, an amidino group, a hydrazine, a hydrazone, a carboxyl group or a salt thereof, sulfonic acid group or a salt thereof, and a phosphoric acid group or a salt thereof; a phenyl group; a naphthyl group; an anthryl group; a fluorenyl group; a pyrenyl group; a phenyl group, a naphthyl group, an anthryl group, a fluorenyl group, or a pyrenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, or a $C_1$-$C_{10}$ alkoxy group, but are not limited thereto.

In Formula 300, $R_{59}$ may be a phenyl group; a naphthyl group; an anthryl group; a biphenyl group; a pyridyl group; or a phenyl group, a naphthyl group, an anthryl group, a biphenyl group, or a pyridyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, or a substituted or unsubstituted $C_1$-$C_{20}$ alkoxy group.

According to an embodiment of the present invention, the compound of Formula 300 may be represented by Formula 300A below, but is not limited thereto.

Formula300A

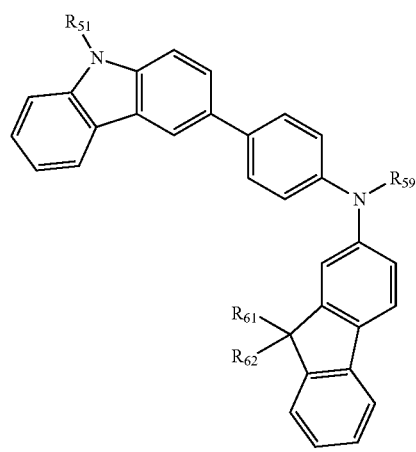

In Formula 300A, each of $R_{51}$, $R_{60}$, $R_{61}$ and $R_{59}$ are as defined above.

For example, at least one of the HIL, the HTL, and the H-functional layer may include at least one of Compounds 301 to 320 below, but the HIL, the HTL, and the H-functional layer are not limited thereto:

301

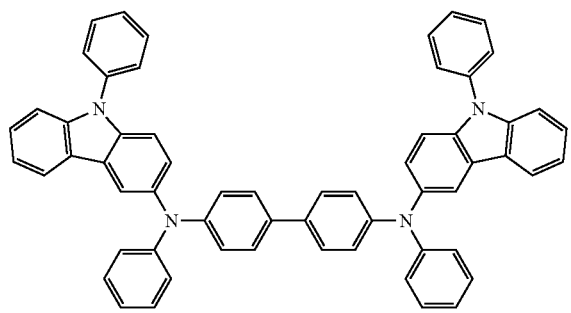

302

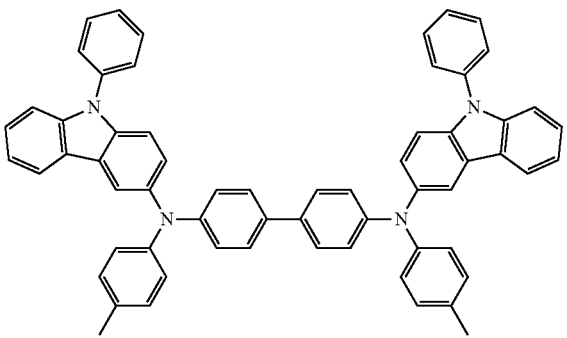

303

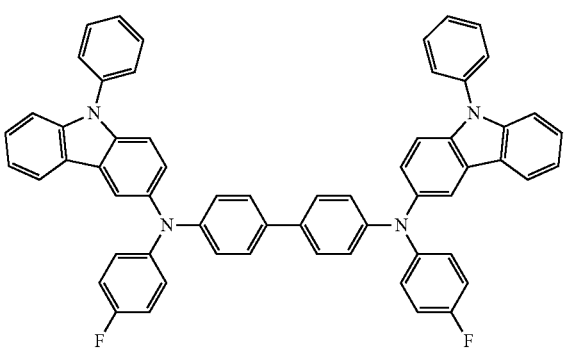

304

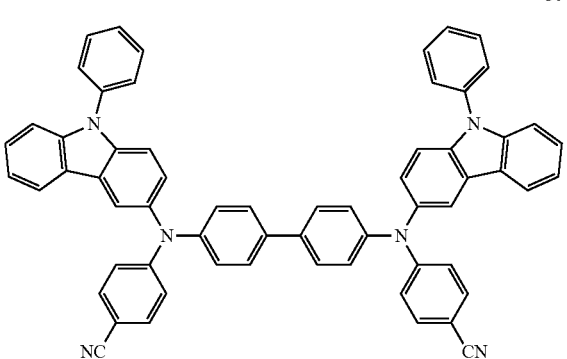

305

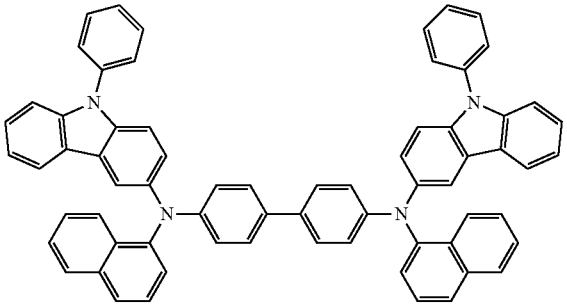

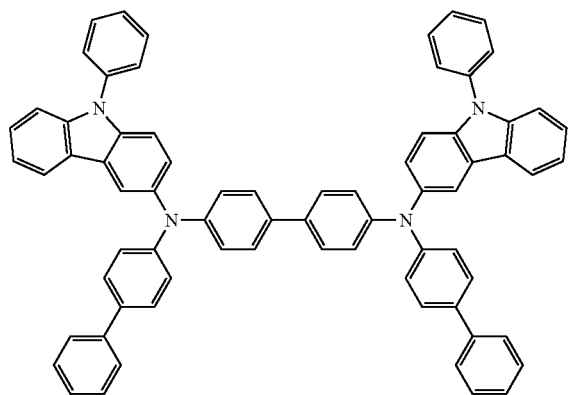
306
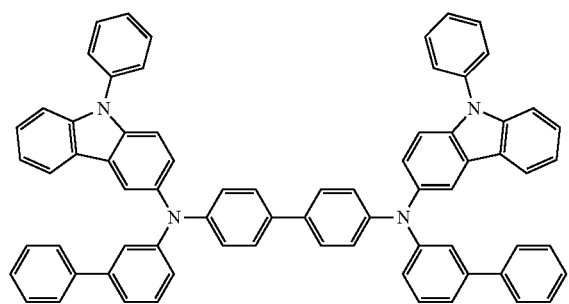
307
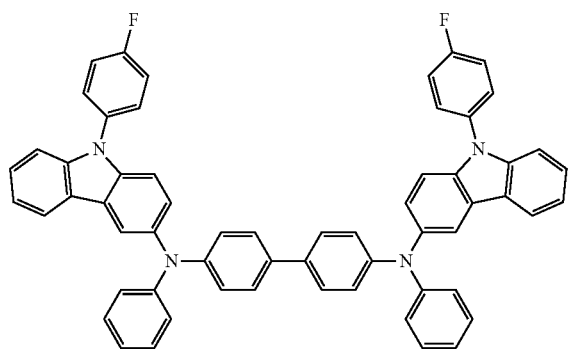
308
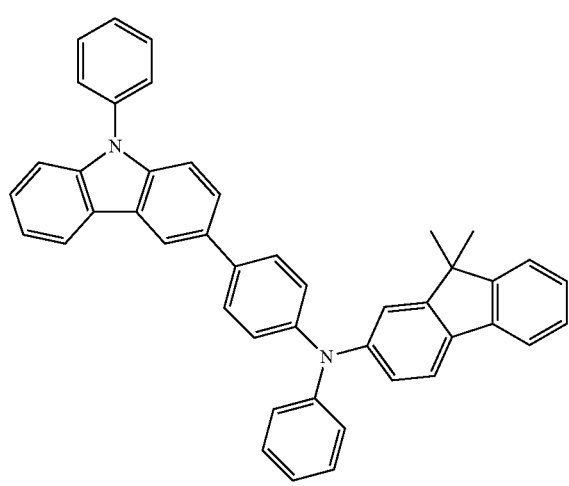
309
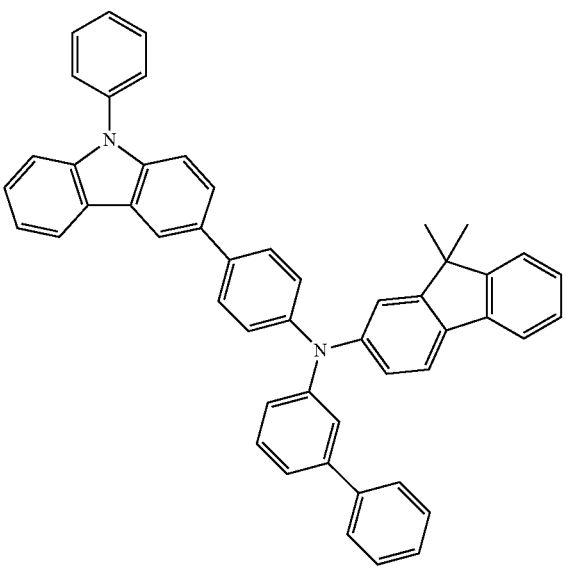
310
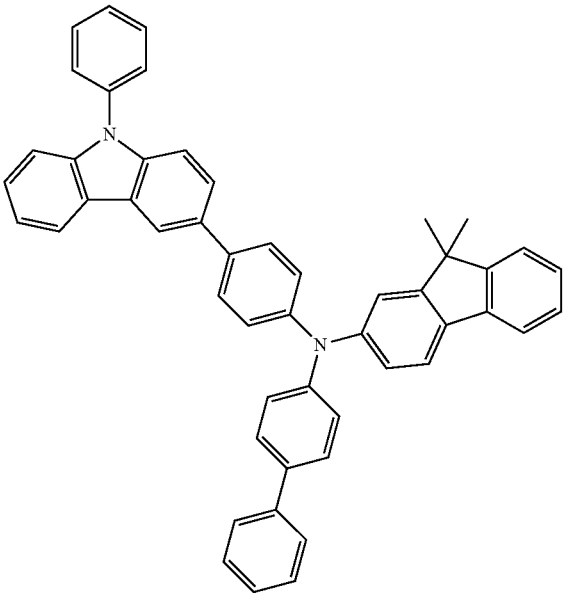
311

-continued
312
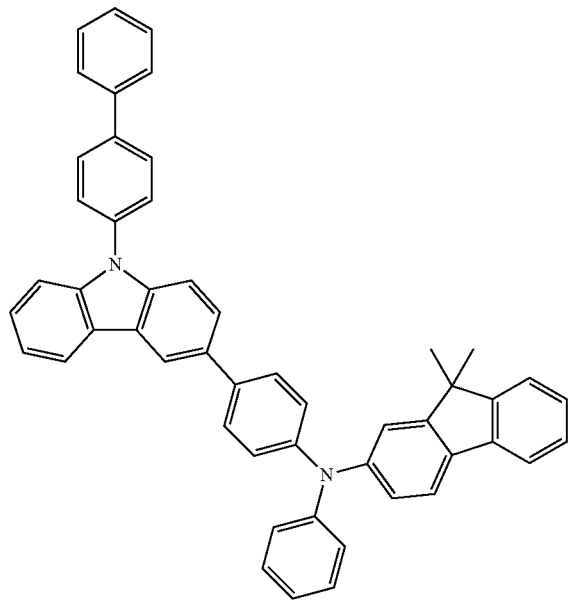
313
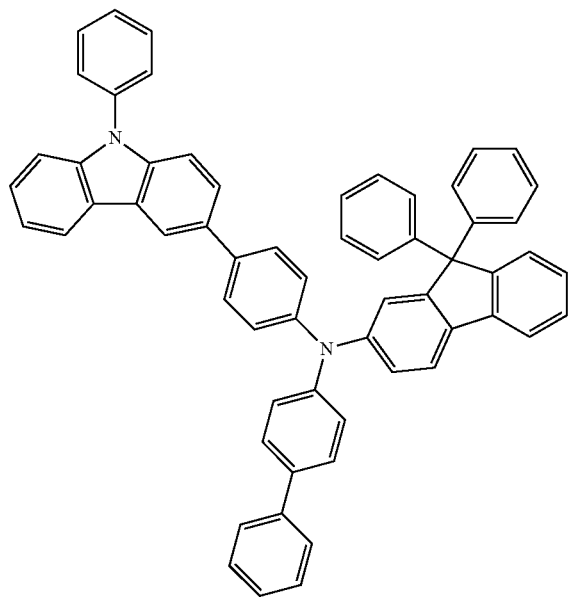
-continued
314
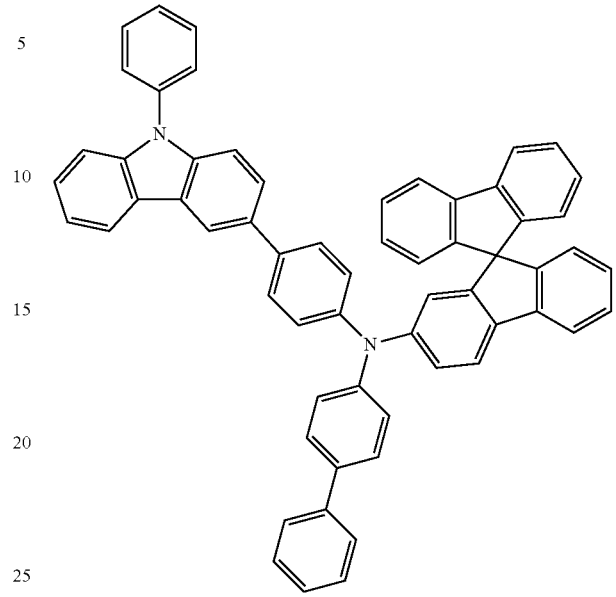
315
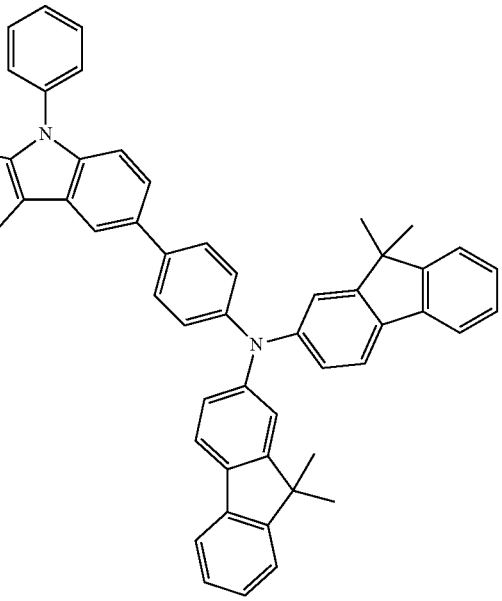

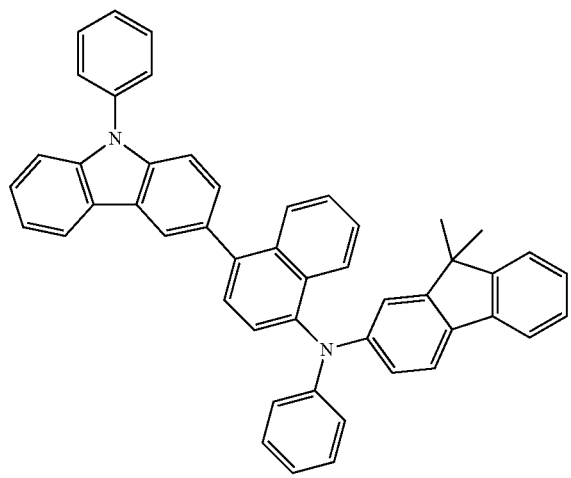

316

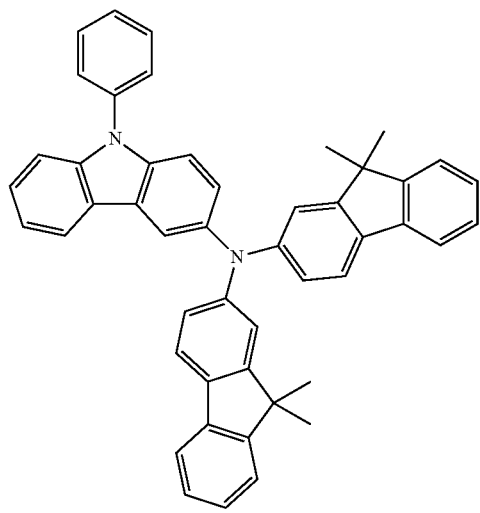

317

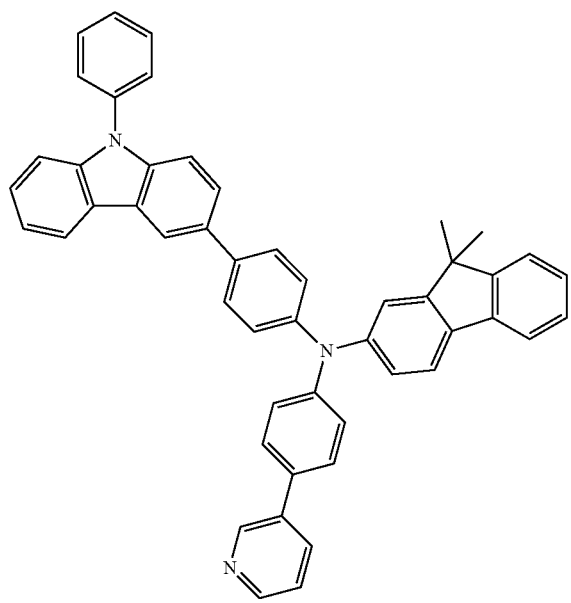

318

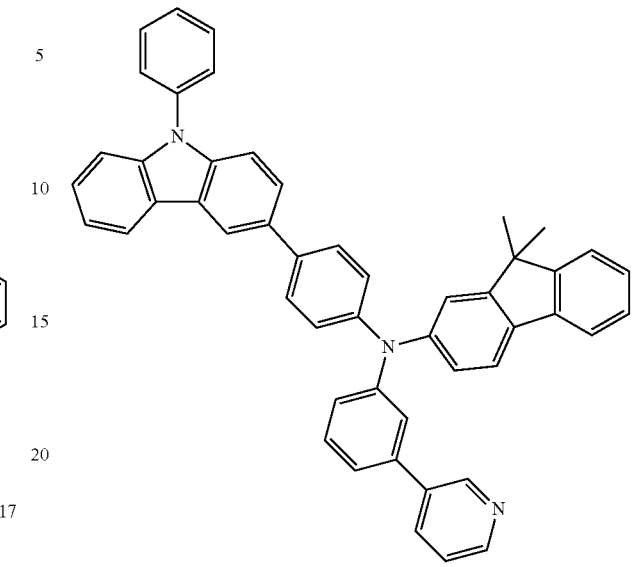

319

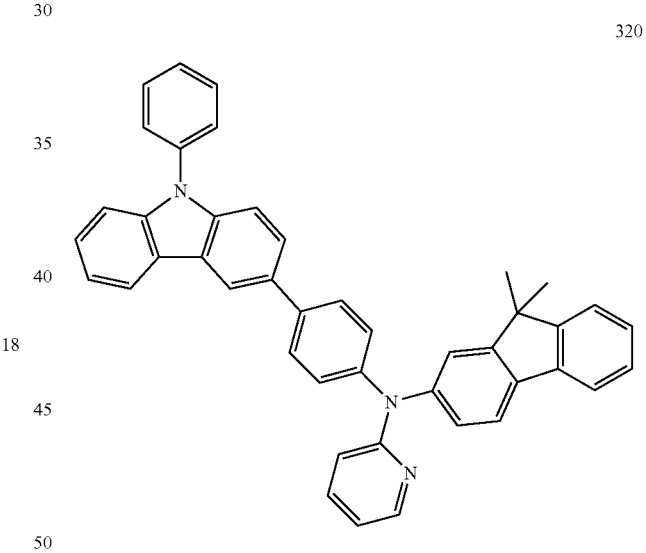

320

In order to improve layer conductivity, at least one of the HIL, the HTL, and the H-functional layer may further include a charge-generating material in addition to the hole injecting material, hole transporting material, and/or the material having both hole injecting and hole transporting capabilities.

The charge-generating material may be a p-dopant. The p-dopant may be a quinone derivative, a metal oxide, or a cyano group-containing compound, but is not limited thereto. Nonlimiting examples of the p-dopant include quinone derivatives such as tetracyanoquinonedimethane (TCNQ) and 2,3,5,6-tetrafluoro-tetracyano-1,4-benzoquinonedimethane (F4-TCNQ); metal oxides such as tungsten oxide and molybdenum oxide; and cyano group-containing compounds such as Compound 200 below.

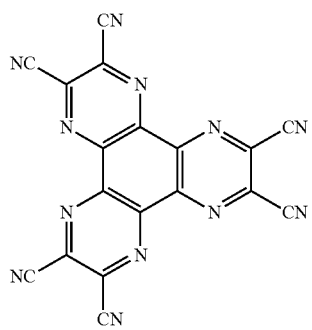

Compound 200

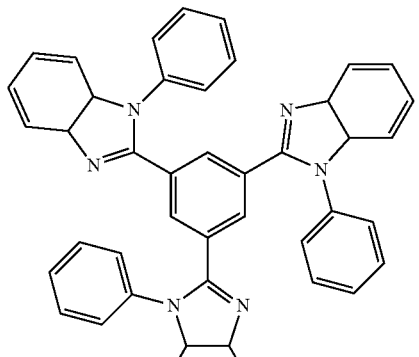

TPBI

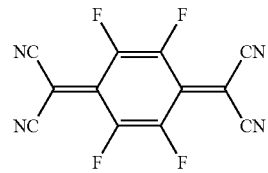

F4-TCNQ

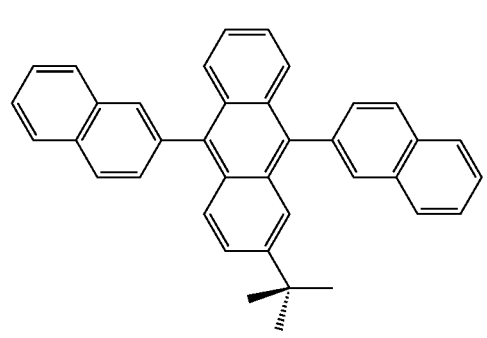

TBADN

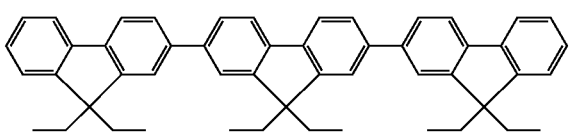

E3

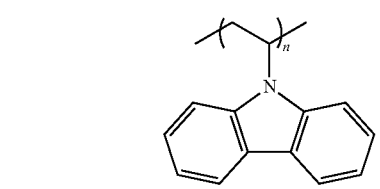

PVK

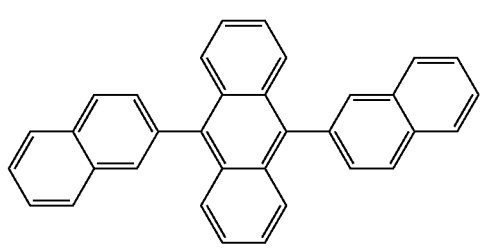

ADN

If the HIL, the HTL, or the H-functional layer further includes the charge-generating material, the charge-generating material may be homogeneously or non-homogeneously dispersed in the HIL, the HTL, or the H-functional layer, or a variety of modifications may be possible.

A buffer layer may be positioned between the EML and at least one of the HIL, the HTL, and the H-functional layer. The buffer layer may increase efficiency by compensating an optical resonant distance according to a wavelength of light emitted from the EML. The buffer layer may include known hole injecting materials and known hole transporting materials. The buffer layer may also include a material that is the same as one of the materials contained in the HIL, the HTL, and the H-functional layer disposed under the buffer layer.

The EML may be formed on the HTL, the H-functional layer, or the buffer layer by vacuum deposition, spin coating, casting, LB deposition, or the like. When the EML is formed by vacuum deposition or spin coating, the deposition or coating conditions may be similar to those used to form the HIL, although the deposition or coating conditions may vary according to the compound used to form the EML.

The EML may include at least one condensed-cyclic compound.

The EML may further include a host in addition to the condensed-cyclic compound. Nonlimiting examples of the host material include Alq$_3$, 4,4'-biscarbazolylbiphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl)anthracene (TBADN), E3, distyrylarylene (DSA), dmCBP (refer to the following formula), and Compounds 501 to 509 below.

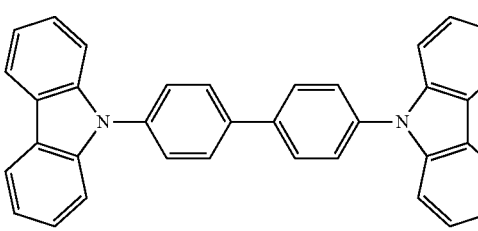

CBP dmCBP
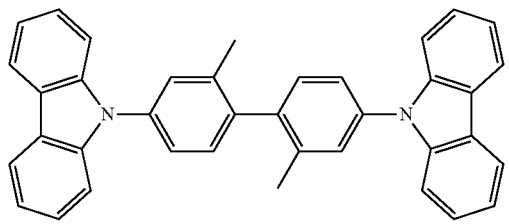
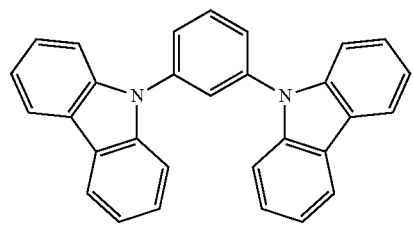
501
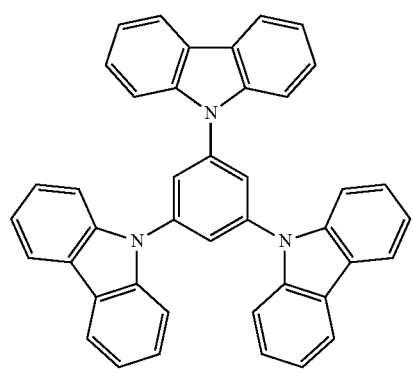
502
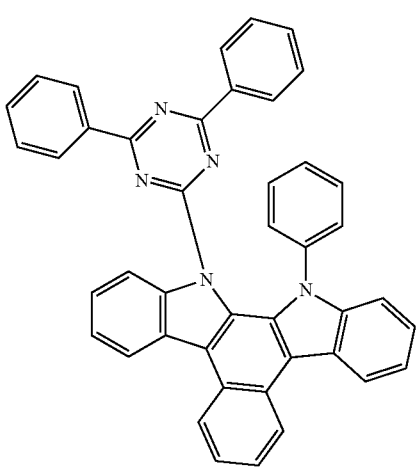
503
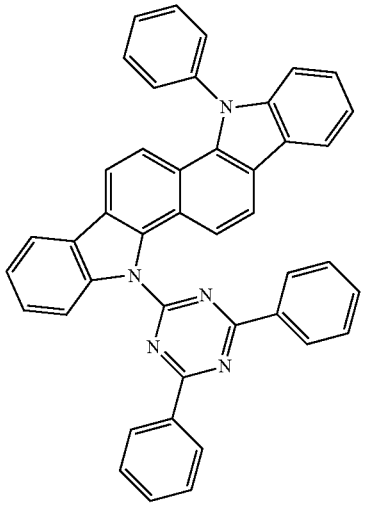
504
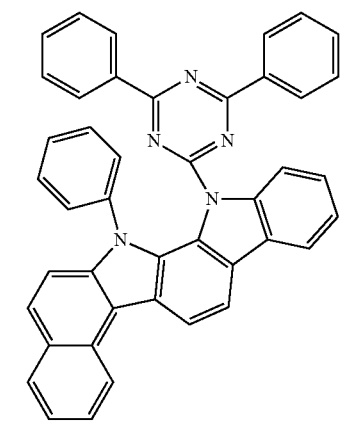
505
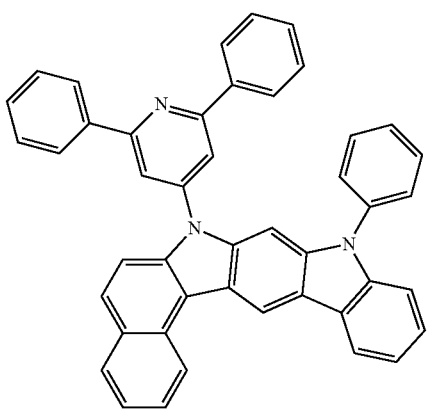
506

-continued

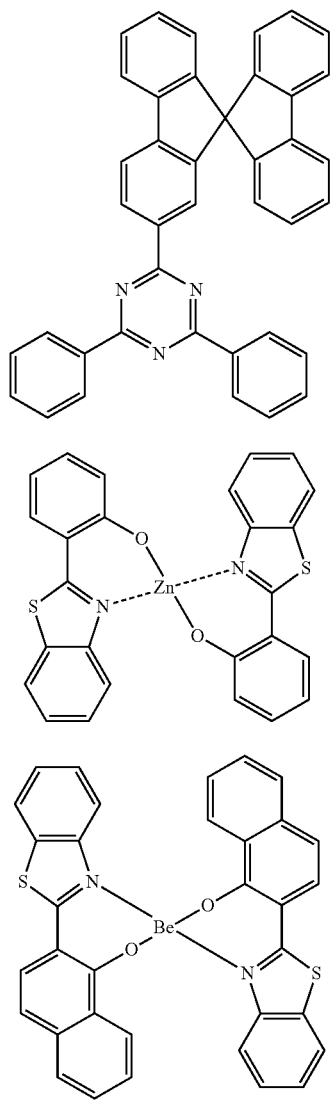

507

508

509

Alternatively, the host may be an anthracene-based compound represented by Formula 400 below.

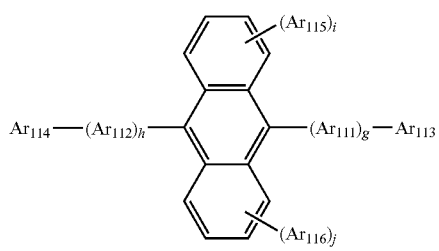

Formula 400

In Formula 400, each of $Ar_{111}$ and $Ar_{112}$ is independently a substituted or unsubstituted $C_6$-$C_{60}$ arylene group. Also, each of $Ar_{113}$ to $Ar_{116}$ is independently a substituted or unsubstituted $C_1$-$C_{10}$ alkyl group or a substituted or unsubstituted $C_6$-$C_{60}$ aryl group. In addition, each of g, h, i, and j is independently an integer from 0 to 4.

For example, in Formula 400, each of $Ar_{111}$ and $Ar_{112}$ may be independently a phenylene group, a naphthylene group, a phenanthrenylene group, or a pyrenylene group; or a phenylene group, a naphthylene group, a phenathrenylene group, a fluorenyl group, or a pyrenylene group substituted with at least one of a phenyl group, a naphthyl group, or an anthryl group, but $Ar_{111}$ and $Ar_{112}$ are not limited thereto.

In Formula 400, each of g, h, i, and j may be independently 0, 1, or 2.

In Formula 400, each of $Ar_{113}$ to $Ar_{116}$ may be independently a $C_1$-$C_{10}$ alkyl group substituted with at least one of a phenyl group, a naphthyl group, or an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, or a fluorenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, a fluorenyl group, or

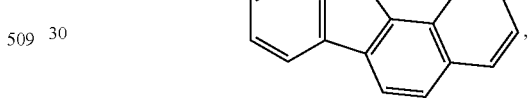

but $Ar_{113}$ to $Ar_{116}$ are not limited thereto.

For example, the anthracene-based compound represented by Formula 400 may be one of the following compounds, but is not limited thereto.

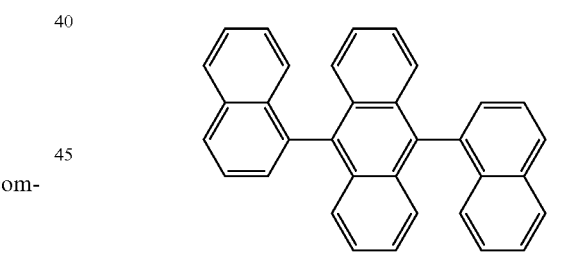

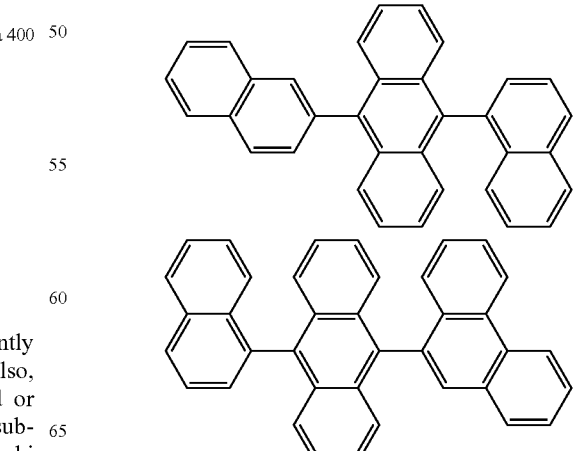

-continued
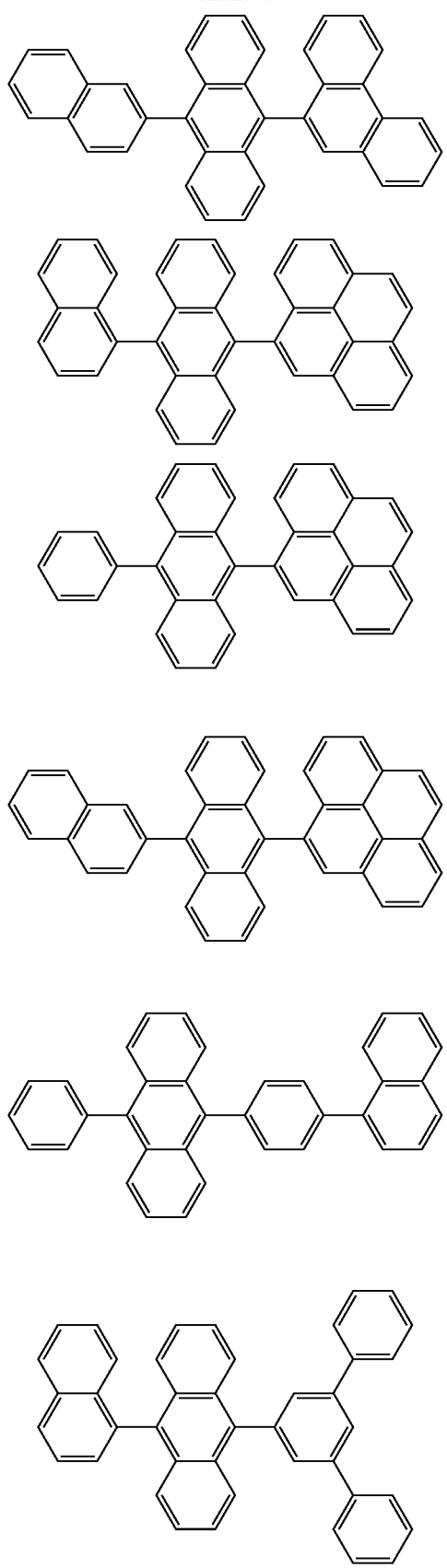
-continued
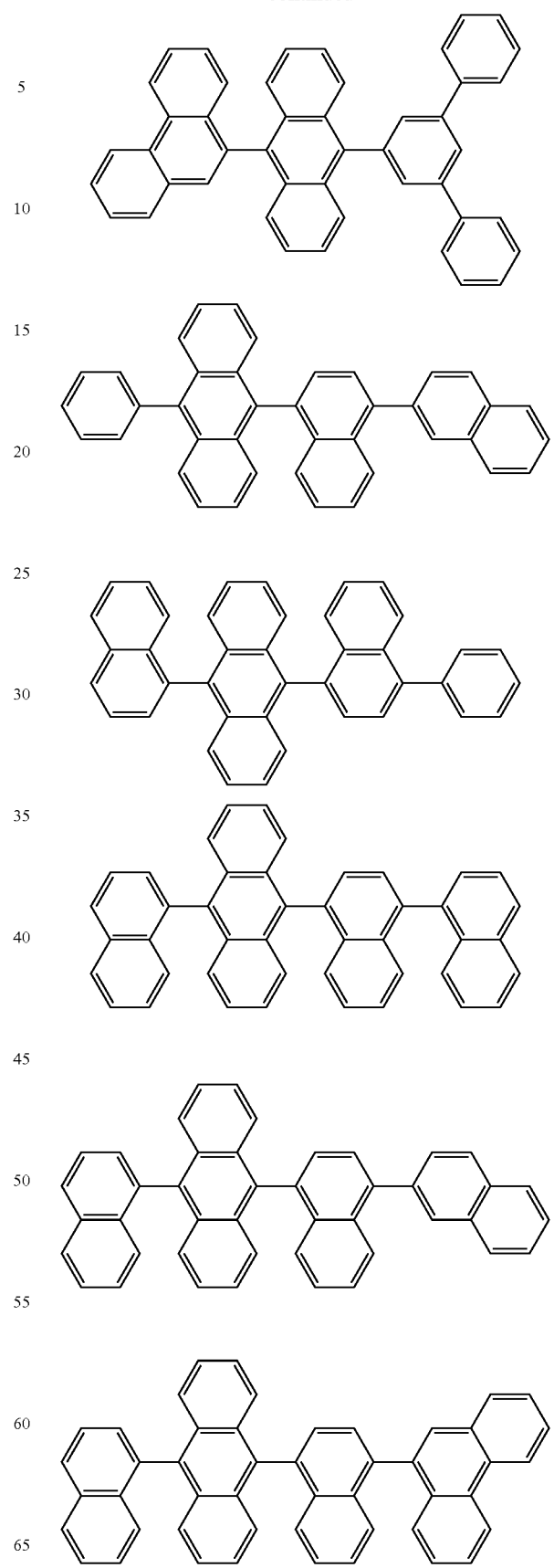

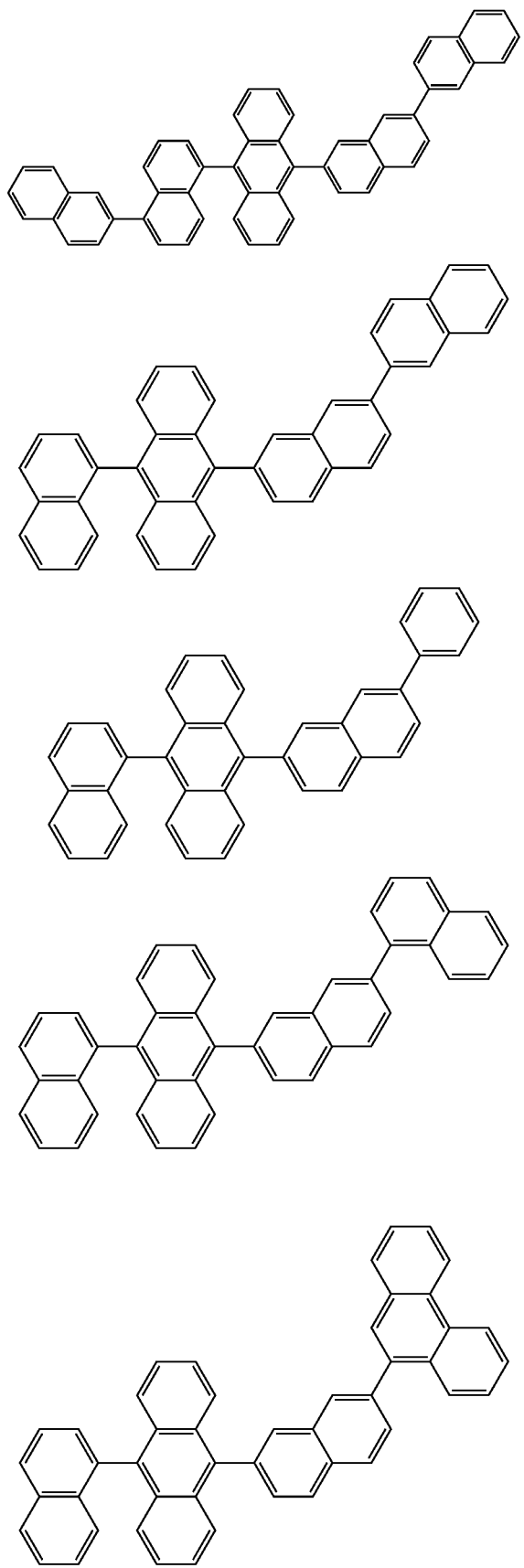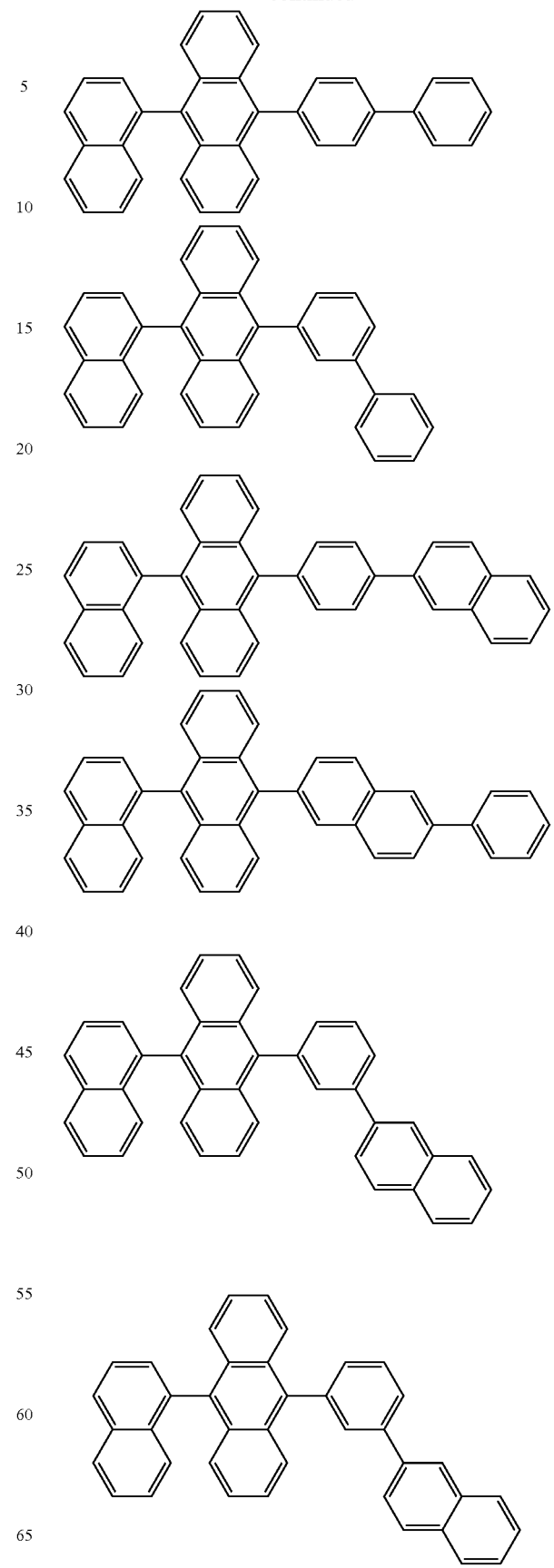

-continued
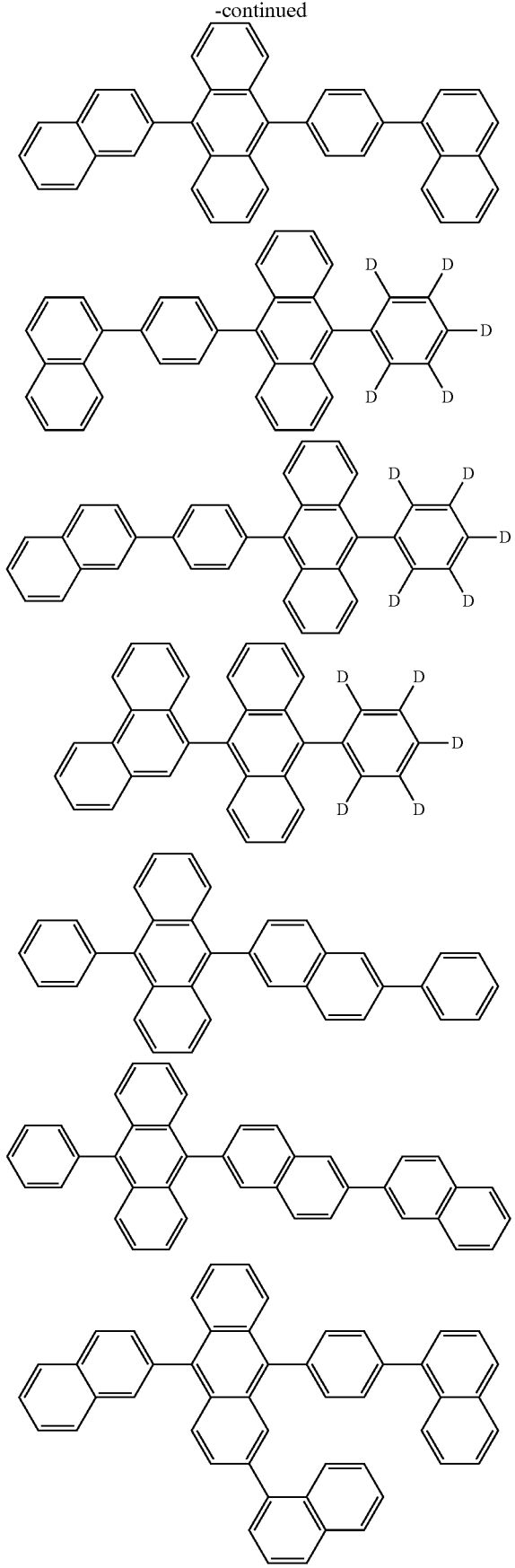
-continued
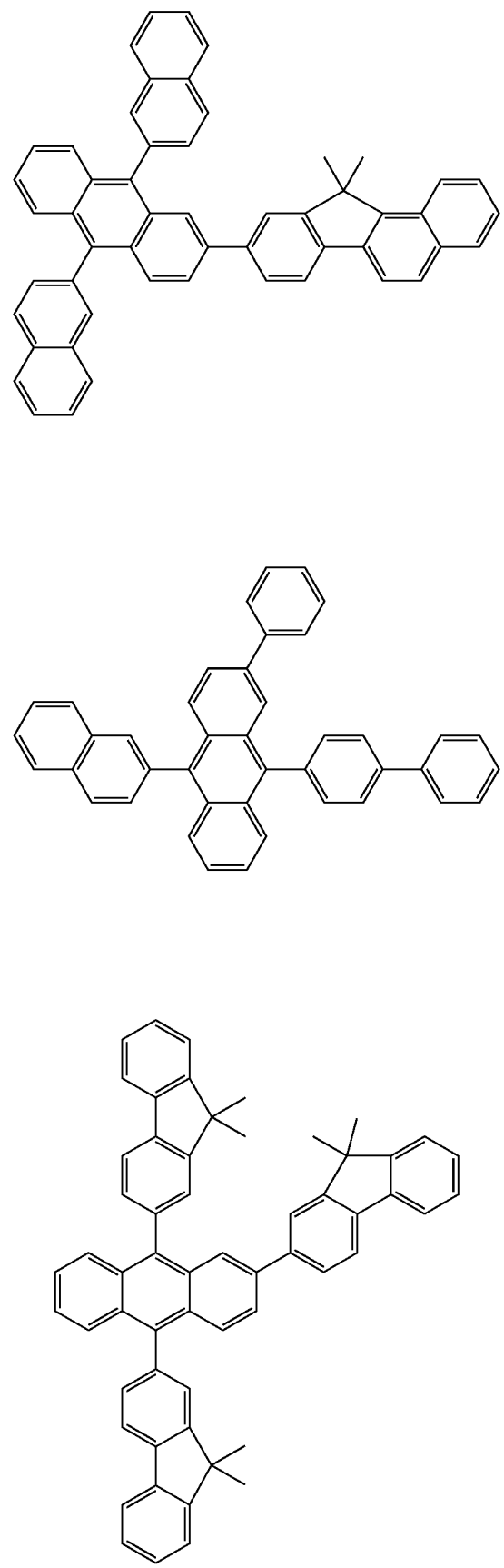

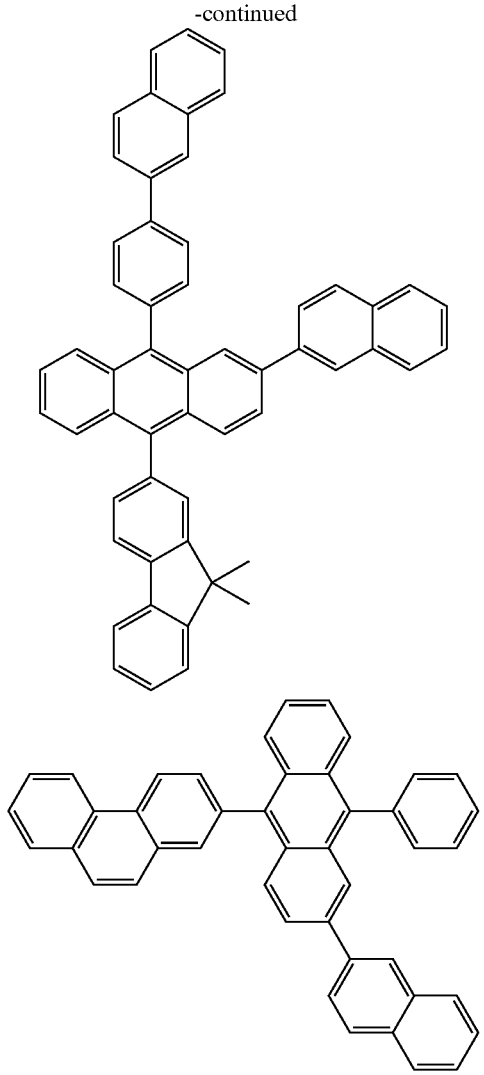

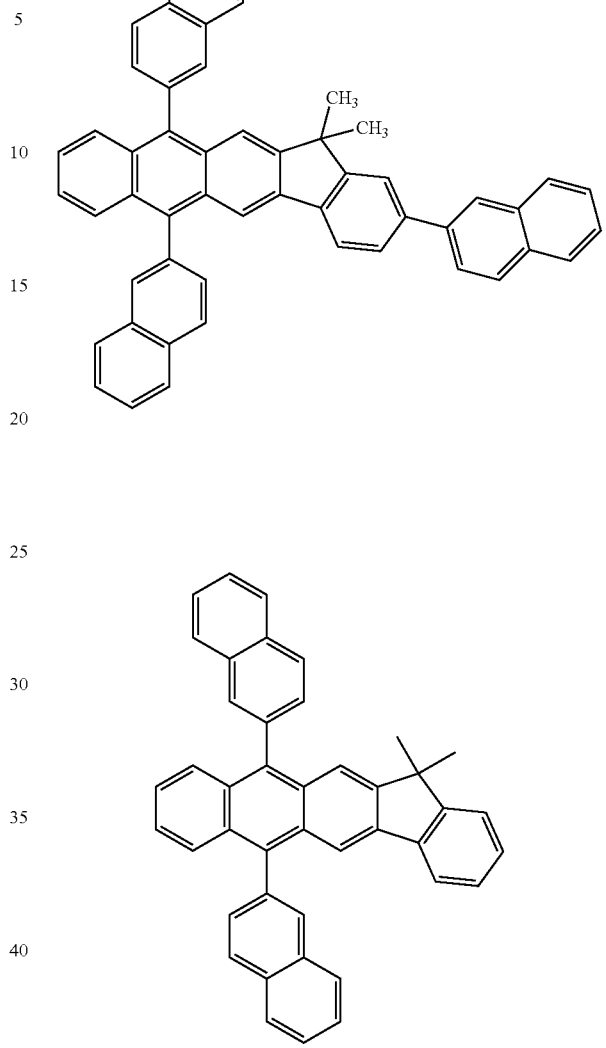

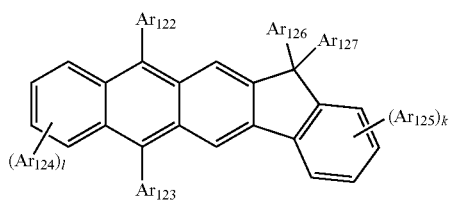

Alternatively, as the host, an anthracene-based compound represented by Formula 401 may be used.

Formula 401

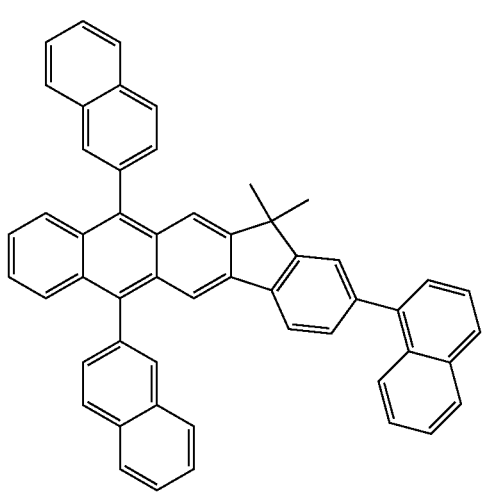

In Formula 401, $Ar_{122}$ to $Ar_{125}$ are as defined above with reference to $Ar_{113}$ of Formula 400.

In Formula 401, each of $Ar_{126}$ and $Ar_{127}$ may be independently a $C_1$-$C_{10}$ alkyl group, such as a methyl group, an ethyl group, or a propyl group.

In Formula 401, each of k and l may be independently an integer from 0 to 4. For example, each of k and l may be independently 0, 1, or 2.

For example, the anthracene-based compound represented by Formula 401 may be one of the following compounds, but is not limited thereto.

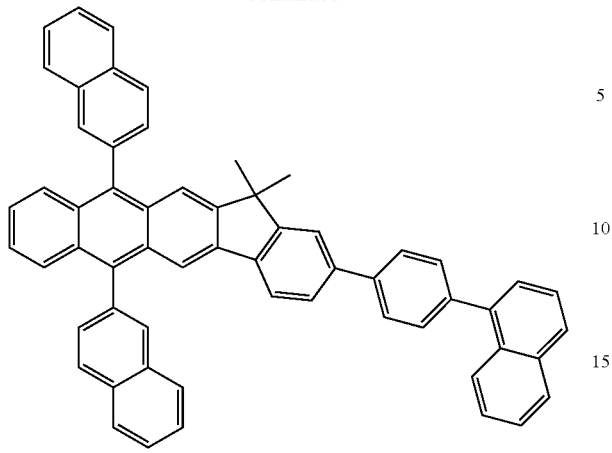

If the organic light-emitting diode is a full-color organic light-emitting diode, the EML may be patterned into a red EML, a green EML, and a blue EML. In this regard, the blue EML or the green EML may include the condensed-cyclic compound described above as a dopant or a host.

Also, at least one of the red, green, and blue EMLs may include at least one of the following dopants (in the below list and depictions, ppy=phenylpyridine).

For example, the following compounds may be used as a blue dopant, but the blue dopant is not limited thereto.

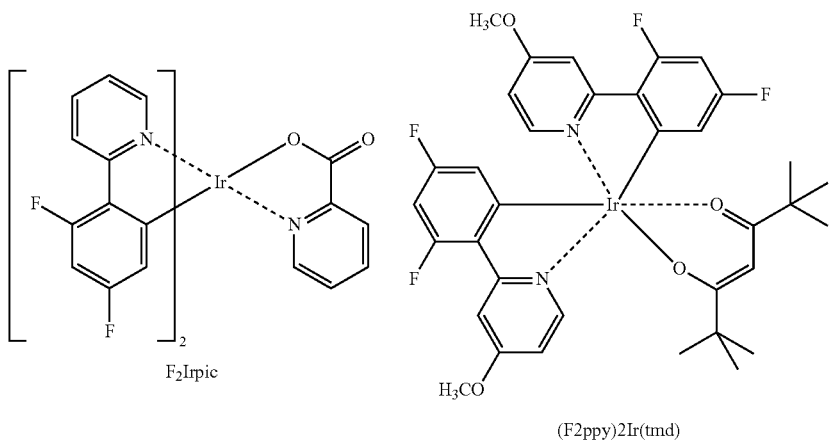

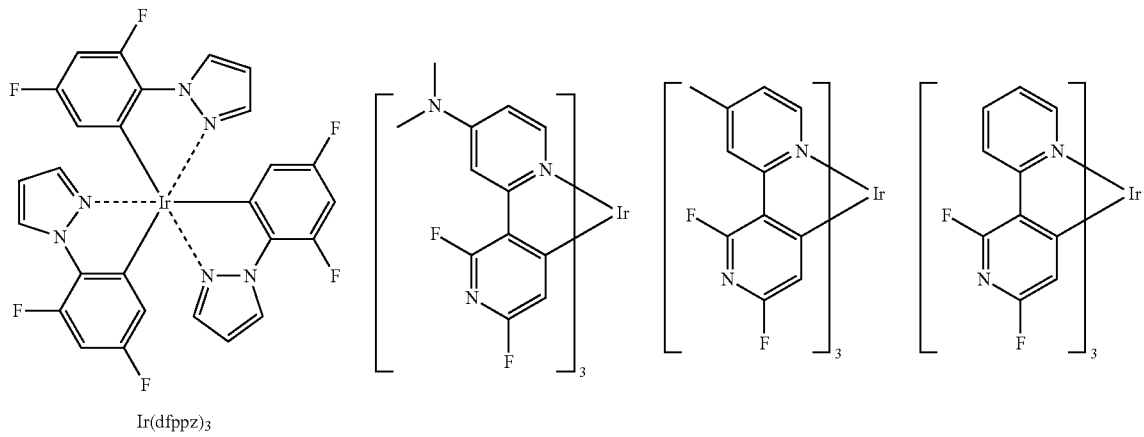

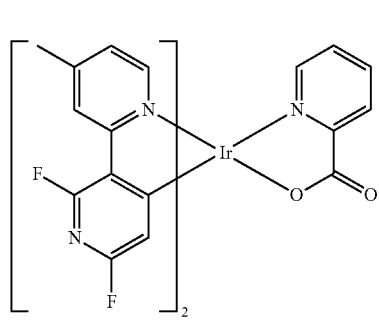
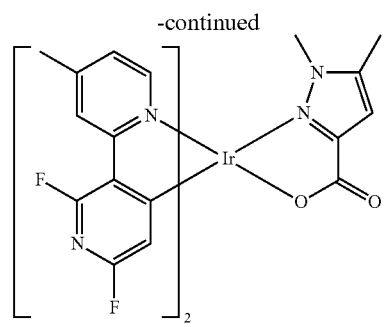
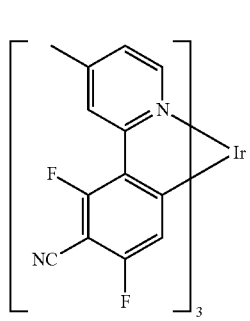
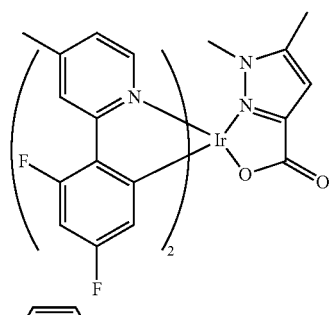
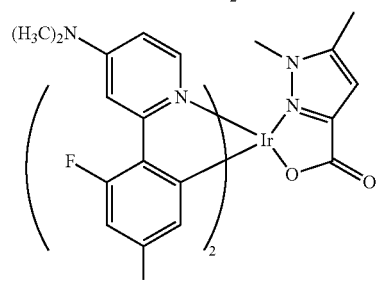
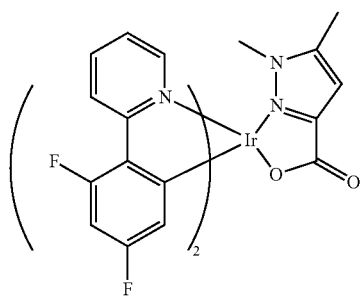
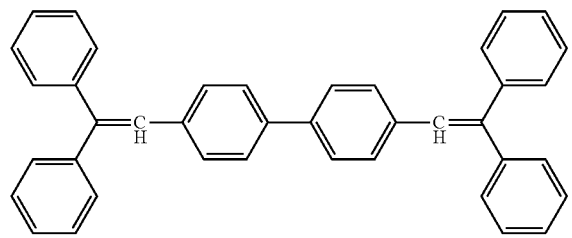
DPVBi
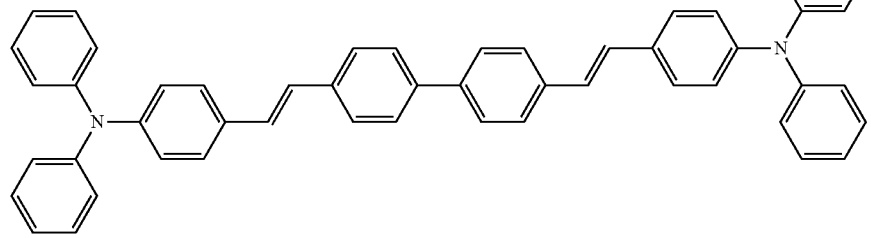
DPAVBi
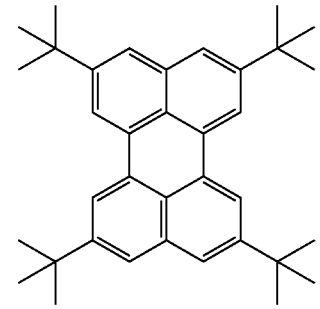
TBPe
For example, the following compounds may be used as a red dopant, but the red dopant is not limited thereto.
-continued
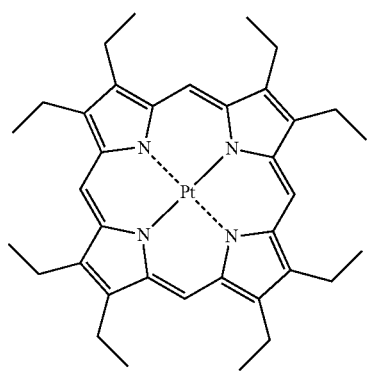
PtOEP
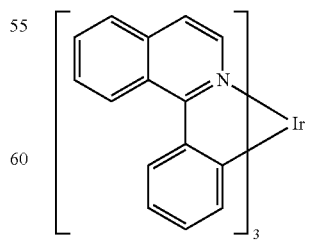
Ir(piq)₃
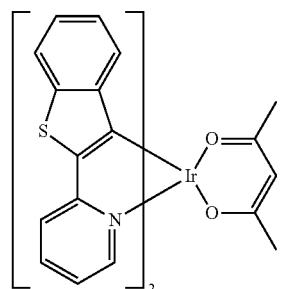
Btp₂Ir(acac)

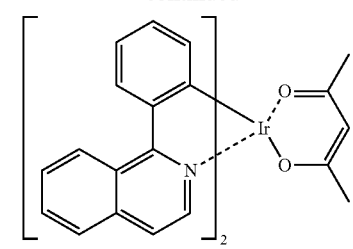
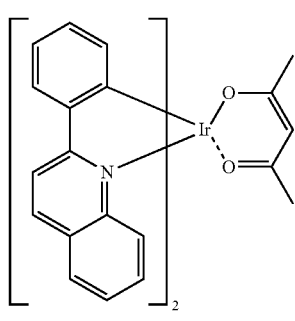
Ir(pq)₂(acac)
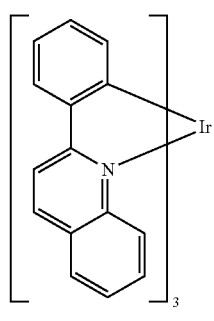
Ir(2-phq)₃
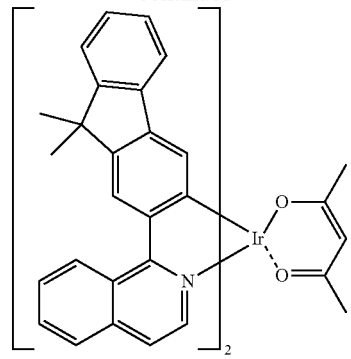
Ir(fliq)₂(acac)
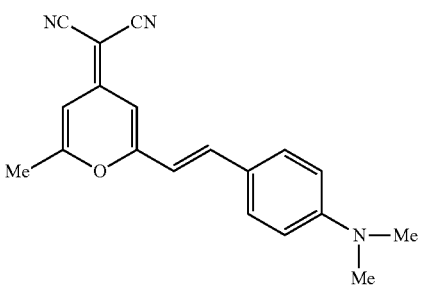
DCM
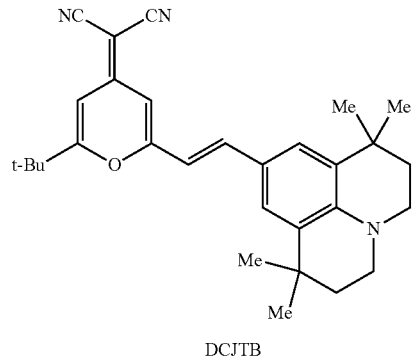
DCJTB
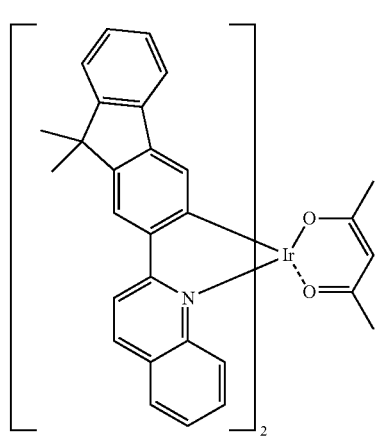
Ir(flq)₂(acac)
For example, the following compounds may be used as a green dopant, but the green dopant is not limited thereto.
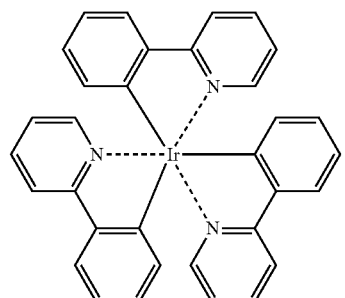
Ir(ppy)₃

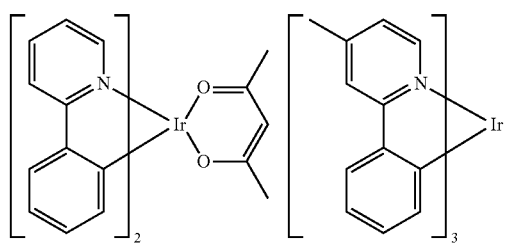
Ir(ppy)₂(acac)
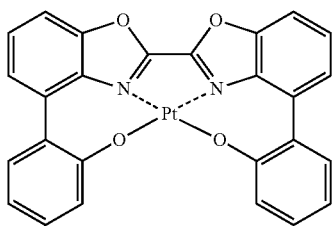
Ir(mpyp)₃
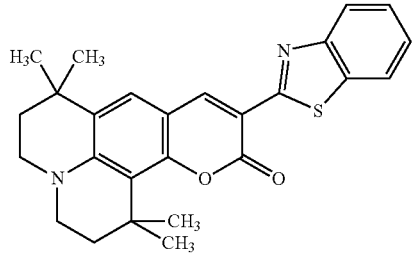
C545T
Additionally, the dopant used in the EML may be at least one of the following Pt-complexes, but the dopant is not limited thereto.
D1
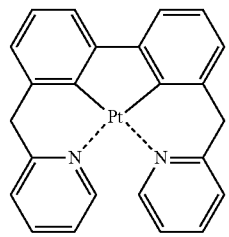
D2
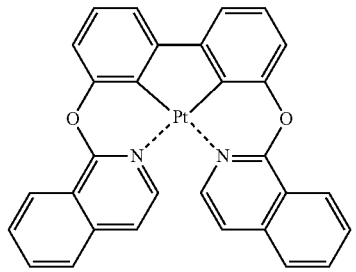
D3
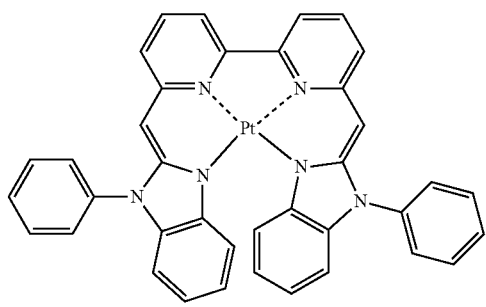
D4
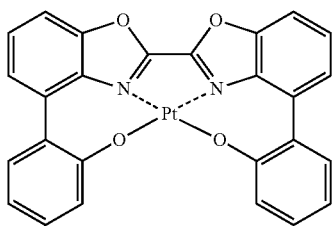
D5
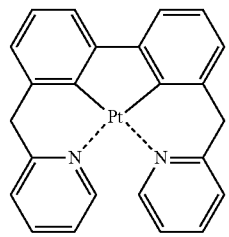
D6
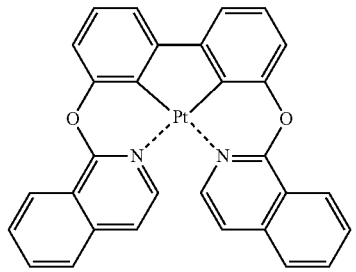
D7
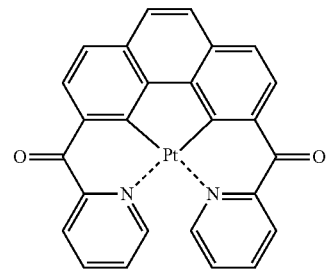
D8
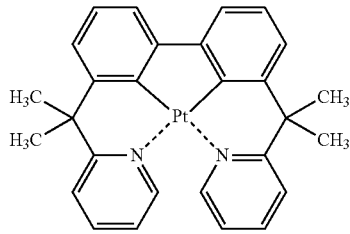
D9
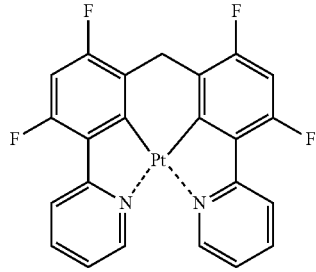

D10 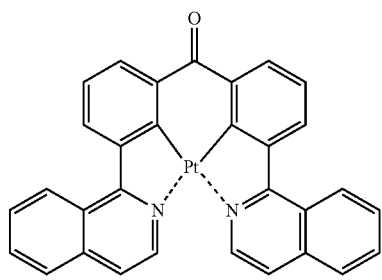
D11 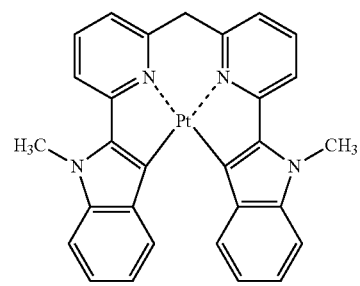
D12 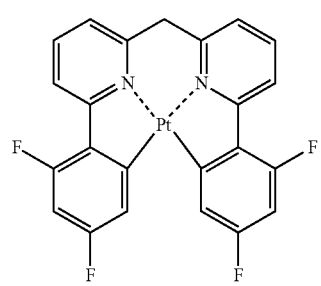
D13 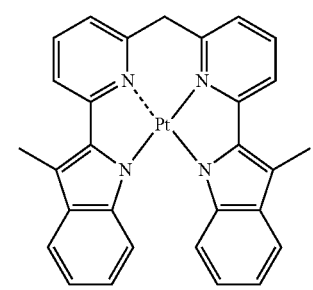
D14 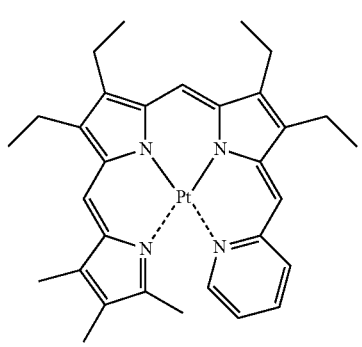
D15 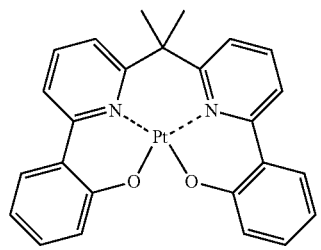
D16 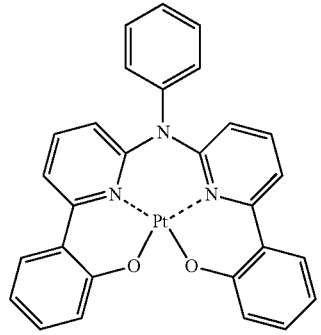
D17 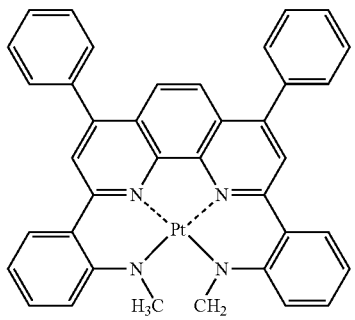
D18 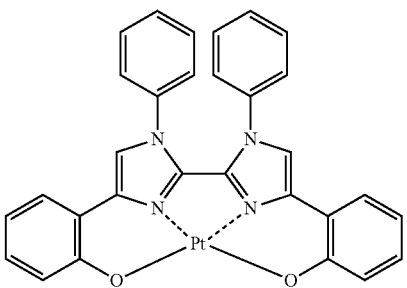
D19 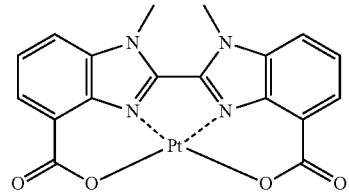
D20 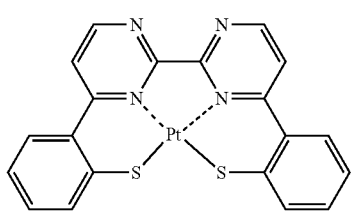

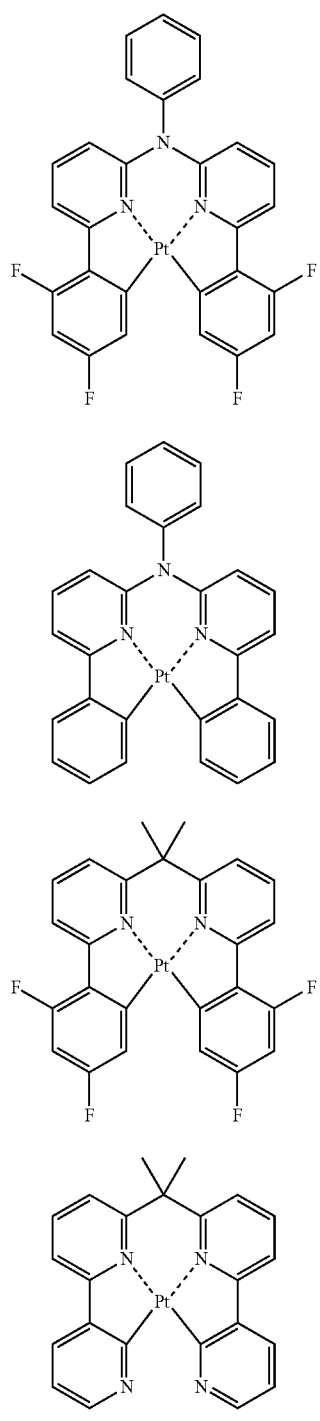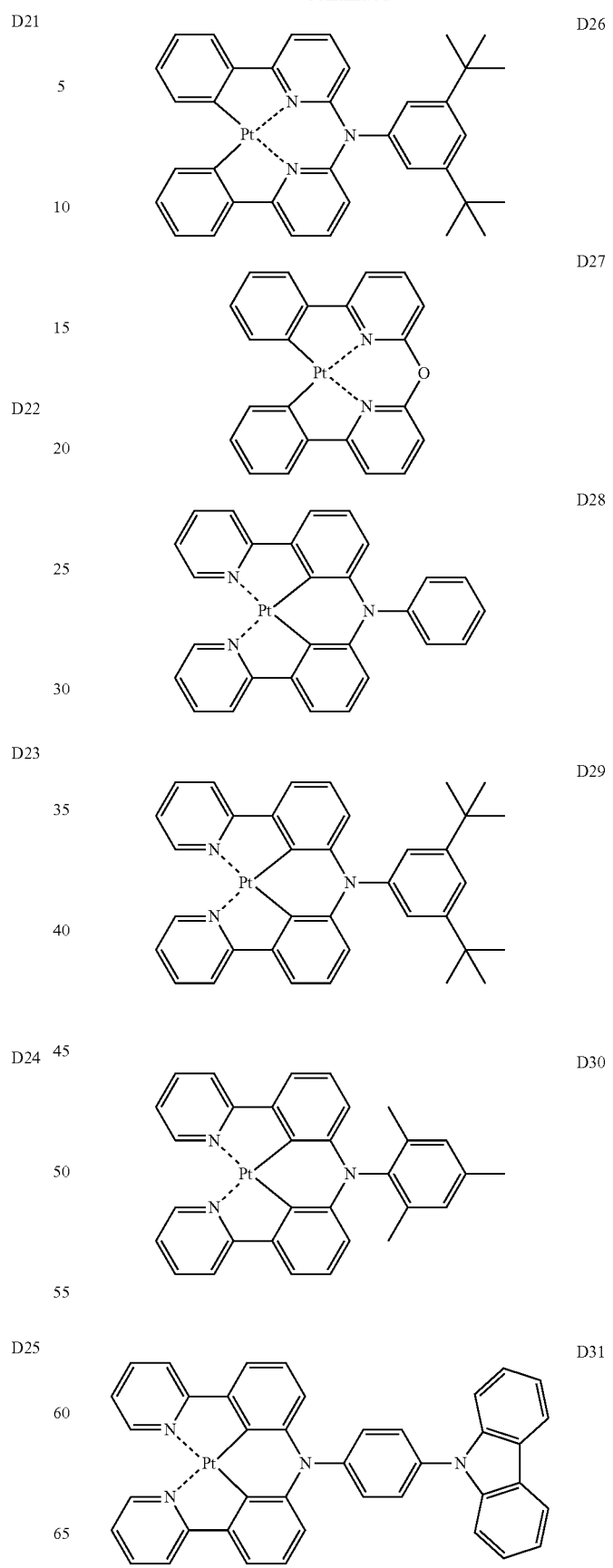

D32 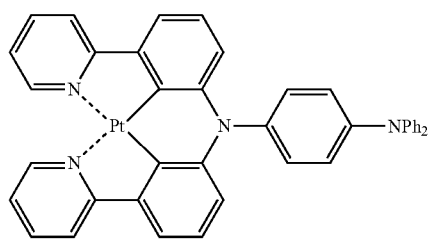
D33 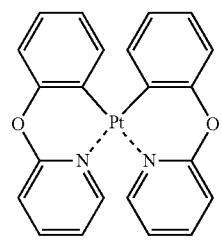
D34 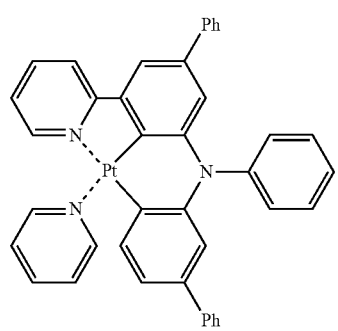
D35 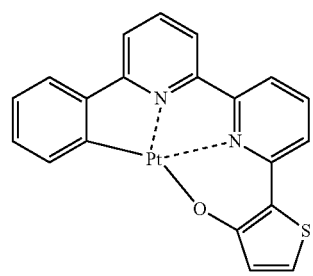
D36 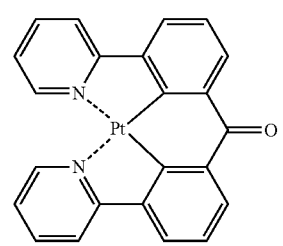
D37 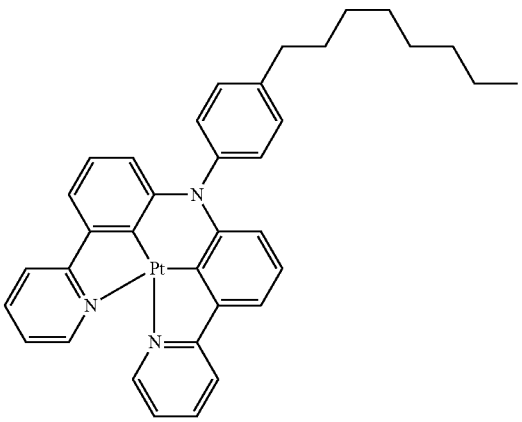
D38 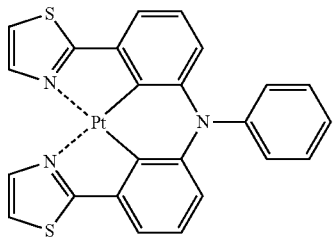
D39 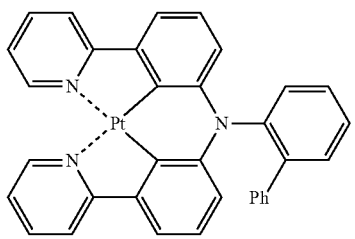
D40 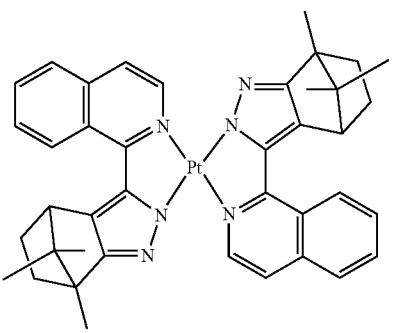
D41 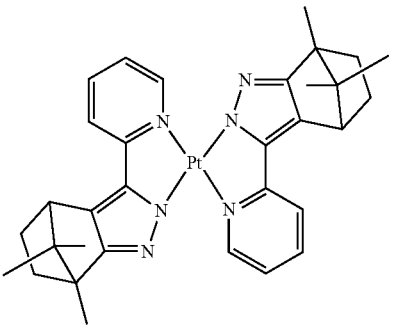

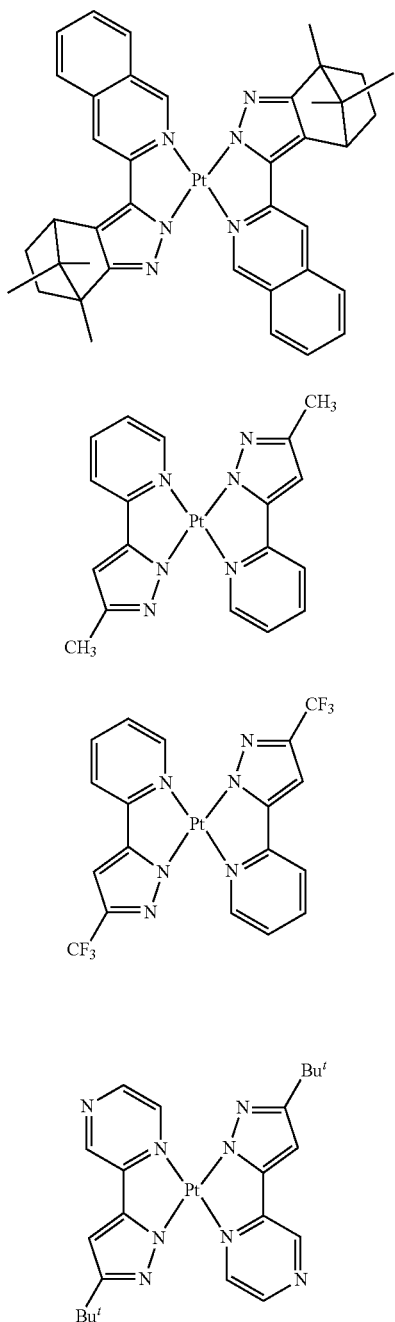
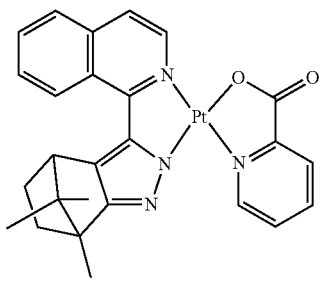
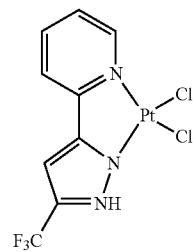
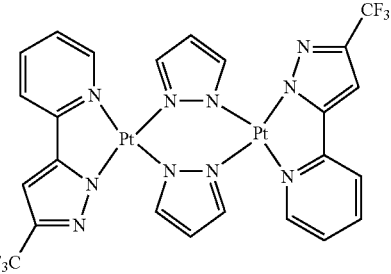
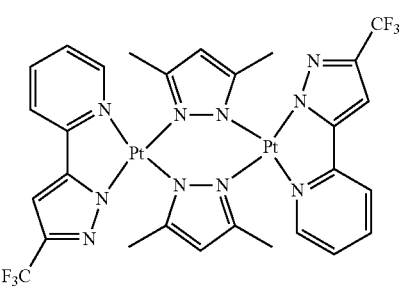
In addition, the dopant used in the EML may be one of the following Os-complexes, but the dopant is not limited thereto.
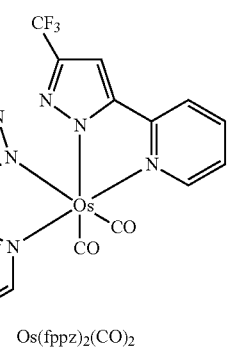
Os(fppz)$_2$(CO)$_2$ -continued

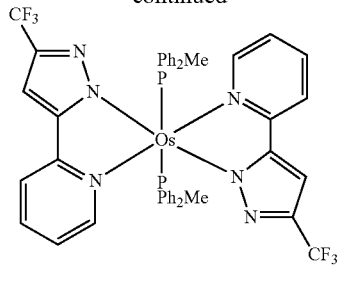
Os(fppz)₂(PPh₂Me)₂

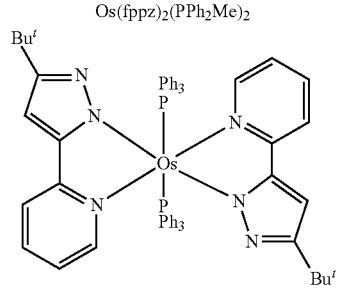
Os(bppz)₂(PPh₃)₂

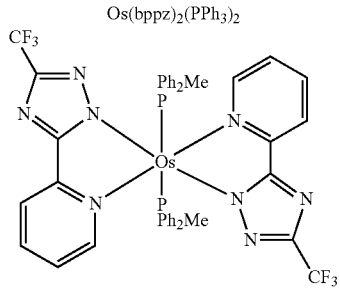
Os(fptz)₂(PPh₂Me)₂

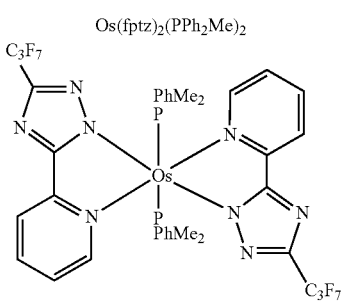
Os(hptz)₂(PPhMe₂)₂ hydroxyquinoline) aluminum (Alq₃), TAZ, Balq, beryllium bis(benzoquinoline-10-olate) (Bebq₂), ADN, Compound 201, and Compound 202.

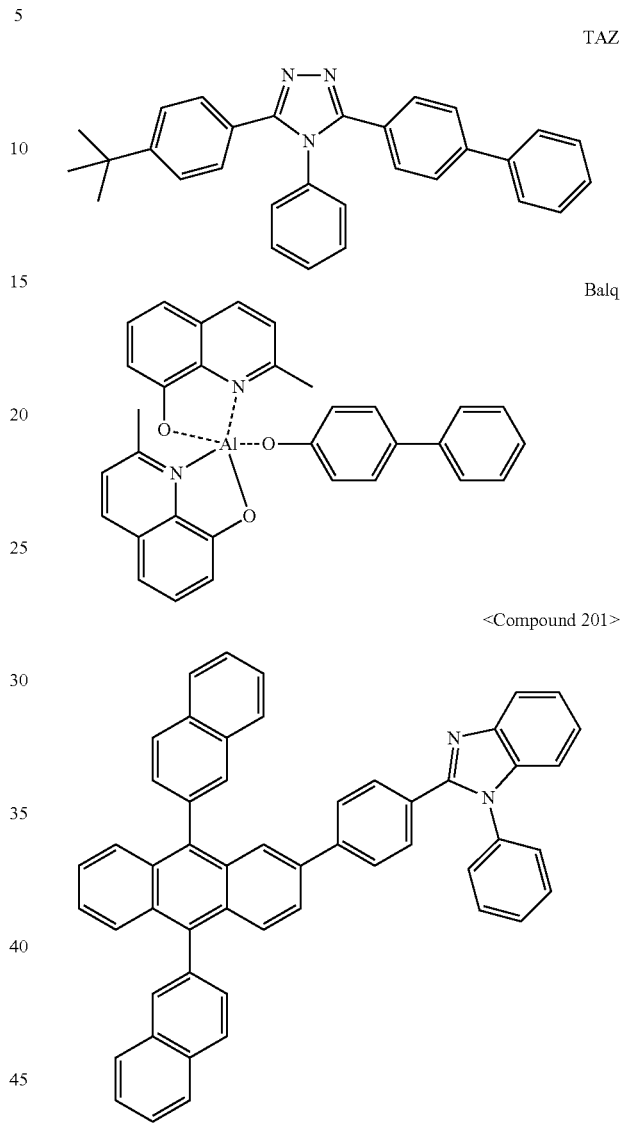

<Compound 202>

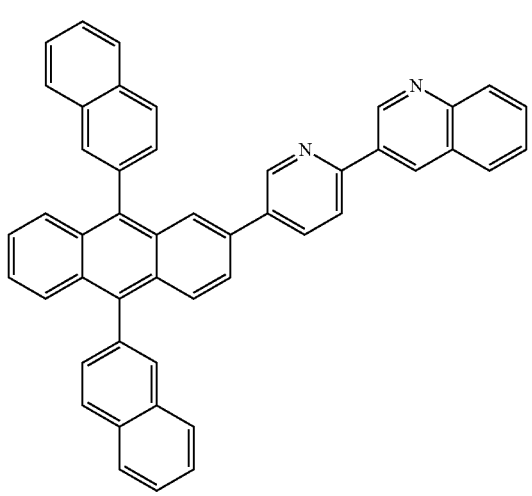

If the EML includes a host and a dopant, the amount of the dopant may be about 0.01 to about 15 parts by weight based on 100 parts by weight of the host, but the amount of the dopant is not limited thereto.

The thickness of the EML may be about 100 Å to about 1000 Å, for example, about 200 Å to about 600 Å. When the thickness of the EML is within these ranges, the EML may have good light emitting ability without a substantial increase in driving voltage.

Then, the ETL may be formed on the EML by vacuum deposition, spin coating, casting, or the like. When the ETL is formed using vacuum deposition or spin coating, the deposition or coating conditions may be similar to those described above with respect to formation of the HIL, although the deposition or coating conditions may vary according to the compound used to form the ETL. The material used to form the ETL may be any material capable of stably transporting electrons injected from the electron injecting electrode (cathode), and any known material may be used. Nonlimiting examples of electron transporting materials include quinoline derivatives, such as tris-(8-

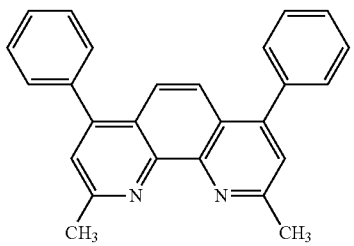

BCP

The thickness of the ETL may be about 100 Å to about 1,000 Å, for example, about 150 Å to about 500 Å. When the thickness of the ETL is within these ranges, the ETL may have good electron transporting ability without a substantial increase in driving voltage.

The ETL may further include a metal-containing material in addition to the electron transporting organic compound(s).

The metal-containing material may include a Li complex. Nonlimiting examples of the Li complex include lithium quinolate (LiQ) or Compound 203 below.

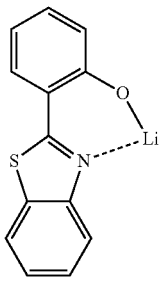

Compound 203

In addition, the EIL may be formed on the ETL using any material that allows electrons to be easily injected from the cathode.

Nonlimiting examples of electron injecting materials include LiF, NaCl, CsF, Li$_2$O, and BaO, which are known in the art. The conditions for deposition of the EIL are similar to those described above with respect to formation of the HIL, although the deposition conditions may vary according to the material used to form the EIL.

The thickness of the EIL may be about 1 to about 100 Å, for example, about 3 to about 90 Å. When the thickness of the EIL is within these ranges, the EIL may have good electron injecting ability without a substantial increase in driving voltage.

A second electrode 17 is disposed on the organic layer 15. The second electrode 17 may be a cathode, which is an electron injecting electrode. The metal used to form the second electrode 17 may be a material having a low work function, such as a metal, an alloy, an electrically conductive compound, or a mixture thereof. For example, the second electrode 17 may be a reflective electrode formed of lithium (Li), magnesium (Mg), aluminum (Al), an Al:Li alloy, calcium (Ca), a Mg:In alloy, or a Mg:Ag in a thin film. In order to manufacture a top-emission type organic light-emitting device, a transmissive (i.e., transparent) electrode formed of ITO or IZO may be used, and various modifications may be made thereto.

The organic light-emitting diode is described with reference to FIG. 1, but is not limited thereto.

In addition, when a phosphorescent dopant is used to form the EML, in order to prevent diffusion of triplet excitons or holes into the ETL, an HBL may be formed between the HTL and the EML or between the H-functional layer and the EML by vacuum deposition, spin coating, casting, LB deposition, or the like. When the HBL is formed using vacuum deposition or spin coating, the conditions for deposition or coating may be similar to those described above with respect to formation of the HIL, although the conditions for deposition or coating may vary according to the material used to form the HBL. Any known hole blocking material commonly used in the art may be used. Nonlimiting examples of hole blocking materials include oxadiazole derivatives, triazole derivatives, and phenanthroline derivatives. For example, BCP may be used as the hole blocking material.

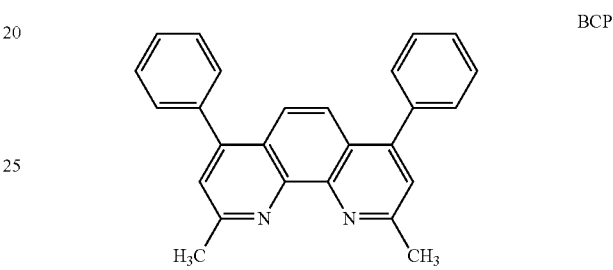

BCP

The thickness of the HBL may be about 20 to about 1,000 Å, for example, about 30 to about 300 Å. When the thickness of the HBL is within these ranges, the HBL may have good hole blocking ability without a substantial increase in driving voltage.

Examples of the unsubstituted $C_1$-$C_{60}$ alkyl group (or the $C_1$-$C_{60}$ alkyl group) discussed herein include linear or branched alkyl groups such as methyl, ethyl, propyl, isobutyl, sec-butyl, pentyl, iso-amyl, and hexyl. The substituted $C_1$-$C_{60}$ alkyl group is obtained by substituting at least one hydrogen atom of the unsubstituted $C_1$-$C_{60}$ alkyl group with a deuterium atom, a halogen atom, a hydroxyl group, a nitro group, a cyano group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_6$-$C_{60}$ aryl group, a $C_2$-$C_{60}$ heteroaryl group, —N($Q_{11}$)($Q_{12}$), or Si($Q_{13}$)($Q_{14}$) ($Q_{15}$)($Q_{11}$)-, where each of $Q_{11}$ to $Q_{15}$ is independently a hydrogen atom, a $C_1$-$C_{60}$ alkyl group, a $C_2$-$C_{60}$ alkenyl group, a $C_2$-$C_{60}$ alkynyl group, a $C_6$-$C_{60}$ aryl group, or a $C_2$-$C_{60}$ heteroaryl group.

The unsubstituted $C_1$-$C_{60}$ alkoxy group (or the $C_1$-$C_{60}$ alkoxy group) discussed herein may be represented by —OA, where A is an unsubstituted $C_1$-$C_{60}$ alkyl group. Examples of the $C_1$-$C_{60}$ alkoxy group include methoxy, ethoxy, and isopropyloxy. The substituted $C_1$-$C_{60}$ alkoxy group may be obtained by substituting at least one hydrogen atom of the $C_1$-$C_{60}$ alkoxy group with the substituent groups described above with respect to the $C_1$-$C_{60}$ alkyl group.

The unsubstituted $C_2$-$C_{60}$ alkenyl group (or the $C_2$-$C_{60}$ alkenyl group) discussed herein refers to a hydrocarbon chain having at least one carbon-carbon double bond within or at a terminal end of the unsubstituted $C_2$-$C_{60}$ alkyl group. Examples of the $C_2$-$C_{60}$ alkenyl group include ethenyl, propenyl, and butenyl. The substituted $C_2$-$C_{60}$ alkenyl group may be obtained by substituting at least one hydrogen atom of the unsubstituted $C_2$-$C_{60}$ alkenyl group with the substituent groups described above with respect to the $C_1$-$C_{60}$ alkyl group.

The unsubstituted $C_2$-$C_{60}$ alkynyl group (or the $C_2$-$C_{60}$ alkynyl group) used herein refers to a hydrocarbon chain having at least one carbon-carbon triple bond within or at a terminal end of the unsubstituted $C_2$-$C_{60}$ alkyl group. Examples of the $C_2$-$C_{60}$ alkenyl group include ethynyl and propynyl. The substituted $C_2$-$C_{60}$ alkynyl group may be obtained by substituting at least one hydrogen atom of the unsubstituted $C_2$-$C_{60}$ alkynyl group with the substituent groups described above with respect to the $C_1$-$C_{60}$ alkyl group.

The unsubstituted $C_6$-$C_{60}$ aryl group discussed herein refers to a monovalent group having a $C_6$-$C_{60}$ carbocyclic aromatic system including at least one aromatic ring. The unsubstituted $C_6$-$C_{60}$ arylene group discussed herein refers to a divalent group having a $C_6$-$C_{60}$ carbocyclic aromatic system including at least one aromatic ring. If the aryl group and arylene group include at least two rings, the rings may be fused to each other or connected to each other by a bond. The substituted $C_6$-$C_{60}$ aryl group and substituted $C_6$-$C_{60}$ arylene group may be obtained by substituting at least one hydrogen atom of the unsubstituted $C_6$-$C_{60}$ aryl group or unsubstituted $C_6$-$C_{60}$ arylene group (respectively) with the substituent groups described above with respect to the $C_1$-$C_{60}$ alkyl group.

Examples of the substituted or unsubstituted $C_6$-$C_{60}$ aryl group include a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m-, or p-fluorophenyl group and a dichlorophenyl group), a dicyanophenyl group, a trifluoromethoxyphenyl group, an o-, m-, or p-tolyl group, an o-, m-, or p-cumenyl group, a mesityl group, a phenoxyphenyl group, an (α,α-dimethylbenzene)phenyl group, an (N,N'-dimethyl)aminophenyl group, an (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentacenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, and an ovalenyl group. Examples of the substituted $C_6$-$C_{60}$ aryl group may be easily derived from the examples of the unsubstituted $C_6$-$C_{60}$ aryl group and the substituents of the substituted $C_1$-$C_{60}$ alkyl group described above. Examples of the substituted or unsubstituted $C_6$-$C_{60}$ arylene group may be easily derived from the examples of the substituted or unsubstituted $C_6$-$C_{60}$ aryl group and the substituents of the substituted $C_1$-$C_{60}$ alkyl group described above.

The unsubstituted $C_2$-$C_{60}$ heteroaryl group is a monovalent group having at least one aromatic ring with at least one heteroatom selected from N, O, P, and S. The unsubstituted $C_2$-$C_{60}$ heteroarylene group is a divalent group having at least one aromatic ring having at least one heteroatom selected from N, O, P, and S. In this regard, when the heteroaryl group and the heteroarylene group have at least two rings, they may be fused to each other or connected by a bond. The substituted $C_2$-$C_{60}$ heteroaryl group and substituted $C_2$-$C_{60}$ heteroarylene group may be obtained by substituting at least one hydrogen atom of the unsubstituted $C_2$-$C_{60}$ heteroaryl group or unsubstituted $C_2$-$C_{60}$ heteroarylene group (respectively) with the substituent groups described above with respect to the $C_1$-$C_{60}$ alkyl group.

Examples of the unsubstituted $C_2$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, and an imidazopyrimidinyl group. Examples of the unsubstituted $C_2$-$C_{60}$ heteroarylene group may be easily derived from the examples of the substituted or unsubstituted $C_2$-$C_{60}$ arylene group.

The substituted or unsubstituted $C_6$-$C_{60}$ aryloxy group is represented by —$OA_2$, where $A_2$ is a substituted or unsubstituted $C_6$-$C_{60}$ aryl group. The substituted or unsubstituted $C_6$-$C_{60}$ arylthio group is represented by —$SA_3$, where $A_3$ is a substituted or unsubstituted $C_6$-$C_{60}$ aryl group.

For example, at least one of the substituents of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{60}$ cycloalkyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted $C_6$-$C_{60}$ arylene group, the substituted $C_6$-$C_{60}$ heteroarylene group, the substituted benzene, the substituted naphthalene, the substituted pyridine, the substituted pyridazine, the substituted pyrimidine, the substituted pyrazine, the substituted triazine, the substituted quinoline, the substituted phthalazine, the substituted naphthyridine, the substituted quinoxaline, the substituted quinazoline, the substituted cinnoline, the substituted benzothiophene, the substituted benzofuran, the substituted dibenzothiophene, and the substituted dibenzofuran is a deuterium atom; a halogen atom; a hydroxyl group; a nitro group; a cyano group; an amino group; an amidino group; a hydrazine; a hydrazone; a carboxyl group or a salt thereof; a sulfonic acid group or a salt thereof; a phosphoric acid group or a salt thereof; a $C_1$-$C_{60}$ alkyl group; a $C_2$-$C_{60}$ alkenyl group; a $C_2$-$C_{60}$ alkynyl group; a $C_6$-$C_{60}$ aryl group; a $C_2$-$C_{60}$ heteroaryl group; or a $C_1$-$C_{60}$ alkyl group, a $C_2$-$C_{60}$ alkenyl group, a $C_2$-$C_{60}$ alkynyl group, a $C_6$-$C_{60}$ aryl group, or a $C_2$-$C_{60}$ heteroaryl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, or a naphthyl group; —$N(Q_{11})(Q_{12})$; or —$Si(Q_{13})(Q_{14})(Q_{15})$, where each of $Q_{11}$ to $Q_{15}$ is independently a hydrogen atom; a $C_1$-$C_{60}$ alkyl group; a $C_6$-$C_{60}$ aryl group; a $C_6$-$C_{60}$ aryl group substituted with a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, or a phosphoric acid group or a salt thereof, a $C_1$-$C_{60}$ alkyl group, or a $C_1$-$C_{60}$ alkoxy group; a $C_2$-$C_{60}$ heteroaryl group; or a $C_2$-$C_{60}$ heteroaryl group substituted with a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, or a phosphoric acid group or a salt thereof, a $C_1$-$C_{60}$ alkyl group, or a $C_1$-$C_{60}$ alkoxy group.

Hereinafter, one or more embodiments will be described with reference to the following examples. These examples are not intended to limit the purpose and/or scope of the one or more embodiments of the present invention.

Synthesis Example 1: Synthesis of Compound 6

Compound 6 was synthesized via Reaction Scheme 2 below:

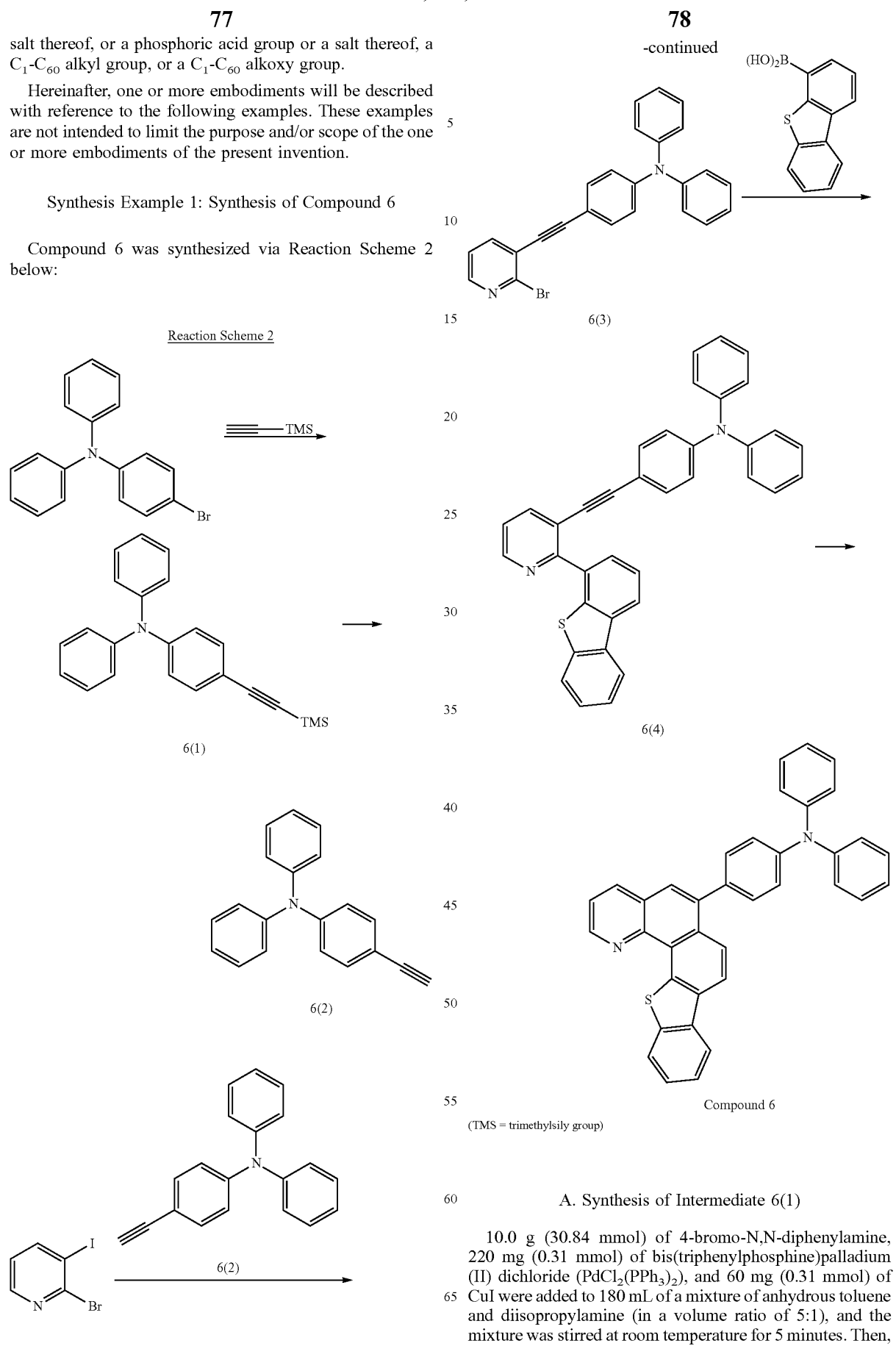

(TMS = trimethylsily group)

A. Synthesis of Intermediate 6(1)

10.0 g (30.84 mmol) of 4-bromo-N,N-diphenylamine, 220 mg (0.31 mmol) of bis(triphenylphosphine)palladium (II) dichloride ($PdCl_2(PPh_3)_2$), and 60 mg (0.31 mmol) of CuI were added to 180 mL of a mixture of anhydrous toluene and diisopropylamine (in a volume ratio of 5:1), and the mixture was stirred at room temperature for 5 minutes. Then, 6.6 ml (46.27 mmol) of ethynyltrimethylsilane was gradually added thereto, and the mixture was stirred at 80° C. for 18 hours. After the reaction was terminated, 50 mL of distilled water was added thereto, and the resultant was subjected to extraction three times with 50 mL of methylene chloride to obtain an organic layer. The organic layer was collected and dried with magnesium sulfate to evaporate the solvent. The residue was separately purified using silica gel column chromatography to obtain 7.9 g (23.13 mmol) of Intermediate 6(1) (Yield: 75%). The produced compound was identified using LC-MS and NMR.

$C_{23}H_{23}NSi$: M+ 342.16.

B. Synthesis of Intermediate 6(2)

1.0 g (2.93 mmol) of Intermediate 6(1) was dissolved in 10.0 mL of THF, and 14.64 mL (14.64 mmol) of a 1.0 M tetrabutylammonium fluoride solution in THF was gradually added thereto at room temperature, and then the mixture was stirred at room temperature for 5 hours. After the reaction was terminated, 50 mL of distilled water was added thereto, and the resultant was subjected to extraction three times with 50 mL of methylene chloride to obtain an organic layer. The organic layer was collected and dried with magnesium sulfate to evaporate the solvent. The residue was separately purified using silica gel column chromatography to obtain 730 mg (2.78 mmol) of Intermediate 6(2) (Yield: 93%). The produced compound was identified using LC-MS.

$C_{20}H_{15}N$: M+ 270.12.

C. Synthesis of Intermediate 6(3)

1.0 g (3.52 mmol) of 2-bromo-3-iodopyridine was dissolved in 10.0 mL of THF, and 1.1 g (3.87 mmol) of Intermediate 6(2), 200 mg (0.18 mmol) of tetrakis(triphenylphosphine)palladium(0) (Pd(PPh$_3$)$_4$), 20 mg (0.18 mmol) of copper iodide (CuI), and 1.47 mL (10.57 mmol) of triethylamine (TEA) were added thereto, and then the mixture was stirred at room temperature for 20 hours. After the reaction was terminated, 20 mL of distilled water was added thereto, and the resultant was subjected to extraction three times with 30 mL of methylene chloride to obtain an organic layer. The organic layer was collected and dried with magnesium sulfate to evaporate the solvent. The residue was separately purified using silica gel column chromatography to obtain 1.47 g (3.46 mmol) of Intermediate 6(3) (Yield: 98%). The produced compound was identified using LC-MS.

$C_{25}H_{17}BrN_2$: M+ 425.06.

D. Synthesis of Intermediate 6(4)

2.0 g (4.70 mmol) of Intermediate 6(3) and 1.6 g (7.05 mmol) of dibenzothiophene-1-yl boronic acid were dissolved in 35.0 mL of tetrahydrofuran, and 270 mg (0.24 mmol) of Pd(PPh$_3$)$_4$ and 2.0 mL of a 5 wt % K$_2$CO$_3$ aqueous solution were added thereto to stop the reaction, and then the mixture was refluxed while stirring at 120° C. for 24 hours. After the reaction was terminated, 20.0 mL of distilled water was added thereto, and the resultant was subjected to extraction three times with 70.0 mL of ethyl acetate to obtain an organic layer. The organic layer was collected and dried with magnesium sulfate to evaporate the solvent. The residue was separately purified using silica gel column chromatography to obtain 1.10 g (2.08 mmol) of Intermediate 6(4) (Yield: 44%). The produced compound was identified using LC-MS.

$C_{37}H_{24}N_2S$: M+ 529.17.

E. Synthesis of Compound 6

At room temperature, 1.0 g (1.89 mmol) of Intermediate 6(4) was dissolved in 10 mL of methylene chloride, and then 5.2 mL (68.10 mmol) of trifluoroacetic acid was added thereto. 30 minutes later, termination of the reaction was determined using $^1$H NMR and HPLC, and the mixture was washed twice with 10 mL of a 10% NaHCO$_3$ solution and washed with 15 mL of water. The organic layer was dried using sodium sulfate to evaporate the solvent. The residue was separately purified using silica gel column chromatography to obtain 960 mg (1.82 mmol) of Compound 6 (Yield: 96%). The produced compound was identified using LC-MS and NMR.

$C_{37}H_{24}N_2S$: M+ 529.18.

1H NMR (CDCl$_3$, 400 MHz) δ (ppm) 7.20 (tt, 2H, J=7.82, J=1.50), 7.21~7.26 (m, 4H), 7.30~7.32 (m, 2H), 7.42~7.47 (m, 2H), 7.57~7.63 (m, 2H), 7.79~7.82 (m, 2H), 7.94~8.04 (m, 2H), 8.20~8.24 (m, 1H), 8.41~8.45 (m, 1H), 8.55~8.65 (m, 3H), 8.74 (dd, 1H, J=6.56, J=4.96), 9.10~9.13 (m, 1H), 9.18 (dd, 1H, J=5.07, J=1.72)

Synthesis Example 2: Synthesis of Compound 12

Compound 12 was synthesized via Reaction Scheme 3 below:

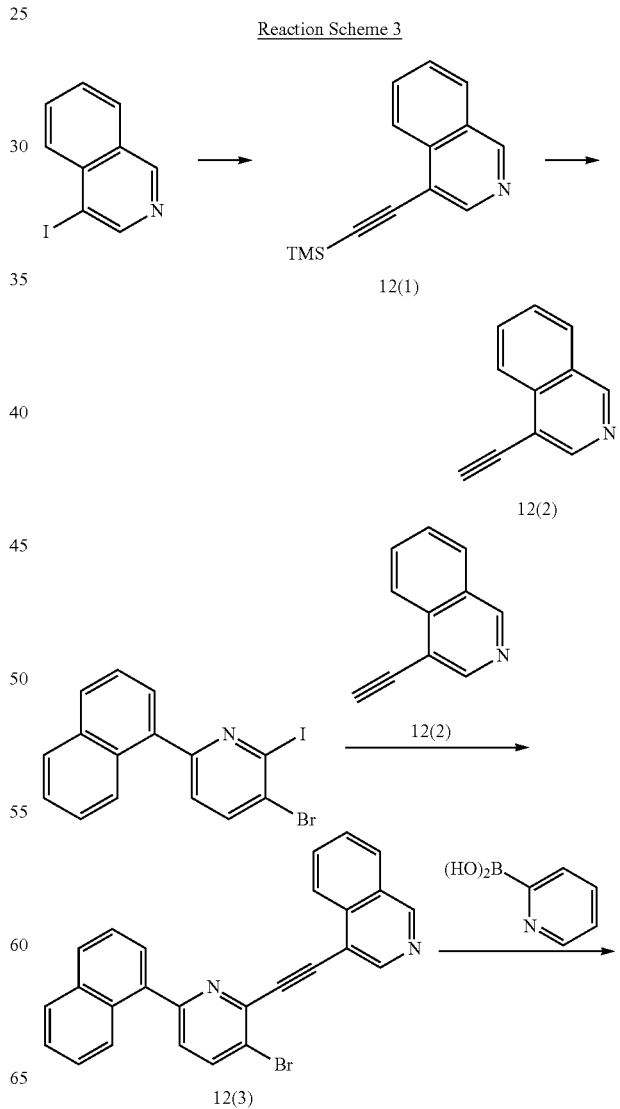

Reaction Scheme 3

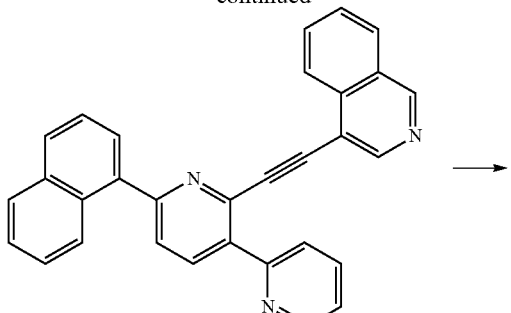

12(4)

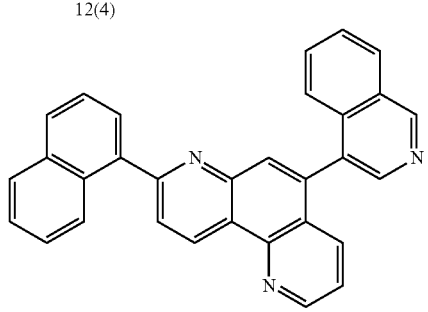

Compound 12

A. Synthesis of Intermediate 12(1)

10.0 g (39.21 mmol) of 4-iodo-isoquinoline, 280 mg (0.39 mmol) of PdCl$_2$(PPh$_3$)$_2$, and 75 mg (0.39 mmol) of CuI were added to 180 mL of a mixture of anhydrous toluene and diisopropylamine (in a volume ratio of 5:1), and the mixture was stirred at room temperature for 5 minutes. Then, 8.4 mL (58.81 mmol) of ethynyltrimethylsilane was gradually added thereto, and the mixture was stirred at 80° C. for 18 hours. After the reaction was terminated, 50 mL of distilled water was added thereto, and the resultant was subjected to extraction three times with 50 mL of methylene chloride to obtain an organic layer. The organic layer was collected and dried with magnesium sulfate to evaporate the solvent. The residue was separately purified using silica gel column chromatography to obtain 6.9 g (30.62 mmol) of Intermediate 12(1) (Yield: 78%). The produced compound was identified using LC-MS.

C$_{14}$H$_{15}$NSi: M+ 226.10.

B. Synthesis of Intermediate 12(2)

1.0 g (4.44 mmol) of Intermediate 12(1) was dissolved in 10.0 mL of THF, and 22.19 mL (22.19 mmol) of a 1.0 M tetrabutylammonium fluoride solution in THF was gradually added thereto at room temperature, and then the mixture was stirred at room temperature for 5 hours. After the reaction was terminated, 50 mL of distilled water was added thereto, and the resultant was subjected to extraction three times with 50 mL of methylene chloride to obtain an organic layer. The organic layer was collected and dried with magnesium sulfate to evaporate the solvent. The residue was separately purified using silica gel column chromatography to obtain 650 mg (4.24 mmol) of Intermediate 12(2) (Yield: 96%). The produced compound was identified using LC-MS.

C$_{11}$H$_7$N: M+ 154.06

C. Synthesis of Intermediate 12(3)

1.0 g (2.44 mmol) of 3-bromo-2-iode-6-naphthalene-1-yl-pyridine was dissolved in 10.0 mL of THF, and 410 mg (2.68 mmol) of Intermediate 12(2), 140 mg (0.12 mmol) of (Pd(PPh$_3$)$_4$), 20 mg (0.12 mmol) of copper iodide (CuI), and 1.02 mL (7.32 mmol) of triethylamine (TEA) were added thereto, and then the mixture was stirred at room temperature for 20 hours. After the reaction was terminated, 20 mL of distilled water was added thereto, and the resultant was subjected to extraction three times with 30 mL of methylene chloride to obtain an organic layer. The organic layer was collected and dried with magnesium sulfate to evaporate the solvent. The residue was separately purified using silica gel column chromatography to obtain 1.0 g (2.30 mmol) of Intermediate 12(3) (Yield: 94%). The produced compound was identified using LC-MS.

C$_{26}$H$_{15}$BrN$_2$: M+ 435.06.

D. Synthesis of Intermediate 12(4)

2.0 g (4.59 mmol) of Intermediate 12(3) and 850 mg (6.89 mmol) of pyridin-2-yl boronic acid were dissolved in 35.0 mL of tetrahydrofuran, and 270 mg (0.23 mmol) of Pd(PPh$_3$)$_4$ and 2.0 mL of a 5 wt % K$_2$CO$_3$ aqueous solution were added thereto, and then the mixture was refluxed while stirring at 120° C. for 24 hours. After the reaction was terminated, the mixture was cooled to room temperature, and 20.0 mL of distilled water was added thereto to stop the reaction. The resultant was subjected to extraction three times with 70.0 mL of ethyl acetate to obtain an organic layer. The organic layer was collected and dried with magnesium sulfate to evaporate the solvent. The residue was separately purified using silica gel column chromatography to obtain 840 mg (1.94 mmol) of Intermediate 12(4) (Yield: 42%). The produced compound was identified using LC-MS.

C$_{31}$H$_{19}$N$_3$: M+ 434.16

E. Synthesis of Compound 12

At room temperature, 1.0 g (1.89 mmol) of Intermediate 12(4) was dissolved in 10 mL of methylene chloride, and then 6.4 mL (84.04 mmol) of trifluoroacetic acid was added thereto. 30 minutes later, termination of the reaction was determined using 1H NMR and HPLC, and the mixture was washed twice with 10 mL of a 10% NaHCO$_3$ solution and washed with 15 mL of water. The organic layer was dried using sodium sulfate to evaporate the solvent. The residue was separately purified using silica gel column chromatography to obtain 920 mg (1.82 mmol) of Compound 12 (Yield: 92%). The produced compound was identified using LC-MS and NMR.

C$_{31}$H$_9$N$_3$: M+ 434.12.

1H NMR (CDCl$_3$, 400 MHz) δ (ppm) 7.68~7.72 (m, 1H), 7.79~7.83 (m, 1H), 7.92~8.09 (m, 5H), 8.28~8.33 (m, 2H), 8.39~8.41 (m, 2H), 8.52~8.62 (m, 2H), 8.66~8.69 (m, 1H), 8.76~8.80 (m, 1H), 8.83 (dd, 1H, J=6.64, J=4.65), 9.40~9.44 (m, 1H), 9.63 (dd, 1H, J=5.09, J=1.83), 9.77 (dd, 1H, J=5.31, J=1.99)

Synthesis Example 3: Synthesis of Compound 24

Compound 24 was synthesized via Reaction Scheme 4 below:

Reaction Scheme 4
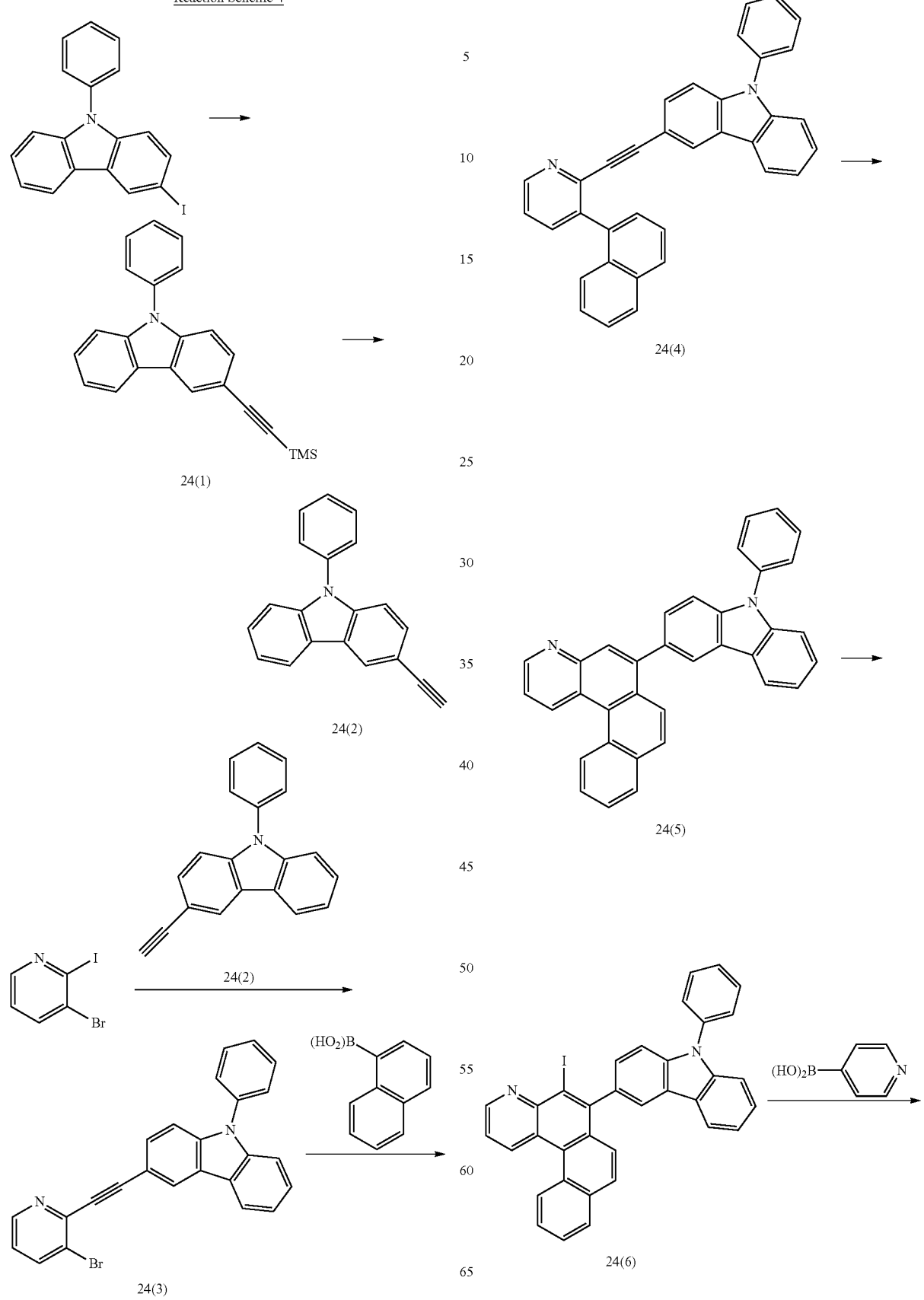

-continued

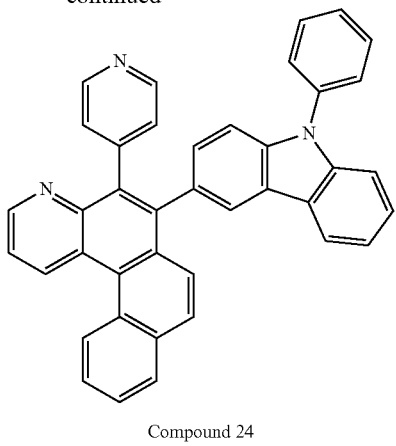

Compound 24

A. Synthesis of Intermediate 24(1)

10.0 g (27.09 mmol) of 3-iodo-9-phenyl-9H-carbazole was dissolved in 100 mL of THF, and 5.8 mL (40.63 mmol) of ethynyltrimethylsilane, 310 mg (0.27 mmol) of tetrakis-triphenylphosphine (Pd(PPh$_3$)$_4$), 52 mg (0.27 mmol) of CuI, and 3.78 mL (27.09 mmol) of triethylamine (TEA) were added thereto, and then the mixture was stirred at room temperature for 5 hours. After the reaction was terminated, 50 mL of distilled water was added thereto, and the resultant was subjected to extraction three times with 50 mL of methylene chloride to obtain an organic layer. The organic layer was collected and dried with magnesium sulfate to evaporate the solvent. The residue was separately purified using silica gel column chromatography to obtain 7.6 g (22.24 mmol) of Intermediate 24(1) (Yield: 82%). The produced compound was identified using LC-MS.

C$_{23}$H$_{21}$NSi: M+ 340.13

B. Synthesis of Intermediate 24(2)

1.0 g (2.95 mmol) of Intermediate 24(1) was dissolved in 10.0 mL of THF, and 14.73 mL (14.73 mmol) of a 1.0 M tetrabutylammonium fluoride solution in THF was gradually added thereto at room temperature, and then the mixture was stirred at room temperature for 5 hours. After the reaction was terminated, 50 mL of distilled water was added thereto, and the resultant was subjected to extraction three times with 50 mL of methylene chloride to obtain an organic layer. The organic layer was collected and dried with magnesium sulfate to evaporate the solvent. The residue was separately purified using silica gel column chromatography to obtain 650 mg (4.24 mmol) of Intermediate 24(2) (Yield: 96%). The produced compound was identified using LC-MS.

C$_{20}$H$_{13}$N: M+ 268.10.

C. Synthesis of Intermediate 24(3)

1.0 g (3.52 mmol) of 2-iodo-3-bromopyridine was dissolved in 10.0 mL of THF, and 590 mg (3.87 mmol) of Intermediate 24(2), 200 mg (0.18 mmol) of (Pd(PPh$_3$)$_4$), 20 mg (0.18 mmol) of copper iodide (CuI), and 1.47 mL (10.57 mmol) of triethylamine (TEA) were added thereto, and then the mixture was stirred at room temperature for 20 hours. After the reaction was terminated, 20 mL of distilled water was added thereto, and the resultant was subjected to extraction three times with 30 mL of methylene chloride to obtain an organic layer. The organic layer was collected and dried with magnesium sulfate to evaporate the solvent. The residue was separately purified using silica gel column chromatography to obtain 1.42 g (3.35 mmol) of Intermediate 24(3) (Yield: 95%). The produced compound was identified using LC-MS.

C$_{25}$H$_{15}$BrN$_2$: M+ 424.02

D. Synthesis of Intermediate 24(4)

2.0 g (4.59 mmol) of Intermediate 24(3) and 1.2 g (7.09 mmol) of naphthalen-1-yl boronic acid were dissolved in 35.0 mL of tetrahydrofuran, and 270 mg (0.24 mmol) of Pd(PPh$_3$)$_4$ and 2.0 mL of a 5 wt % K$_2$CO$_3$ aqueous solution were added thereto, and then the mixture was refluxed while stirring at 120° C. for 24 hours. After the reaction was terminated, the mixture was cooled to room temperature, and then 20.0 mL of distilled water was added thereto to stop the reaction. The resultant was subjected to extraction three times with 70 mL of ethyl acetate to obtain an organic layer. The organic layer was collected and dried with magnesium sulfate to evaporate the solvent. The residue was separately purified using silica gel column chromatography to obtain 860 mg (1.83 mmol) of Intermediate 24(4) (Yield: 39%). The produced compound was identified using LC-MS.

C$_{35}$H$_{22}$N$_2$: M+ 471.19.

E. Synthesis of Compound 24(5)

At room temperature, 1.0 g (2.13 mmol) of Intermediate 24(4) was dissolved in 10 mL of methylene chloride, and then 5.9 mL (76.50 mmol) of trifluoroacetic acid was added thereto. 30 minutes later, termination of the reaction was determined using 1H NMR and HPLC, and the mixture was washed twice with 10 mL of a 10% NaHCO$_3$ solution and washed with 15 mL of water. The organic layer was dried using sodium sulfate to evaporate the solvent. The residue was separately purified using silica gel column chromatography to obtain 920 mg (1.96 mmol) of Compound 24(5) (Yield: 92%). The produced compound was identified using LC-MS.

C$_{35}$H$_{22}$N$_2$: M+ 471.16

F. Synthesis of Compound 24(6)

250 mg (0.67 mmol) of bis(pyridine)iodonium tetrafluoroborate was dissolved in 25 mL of dichloromethane in a flask wrapped with aluminum foil, and 6.4 uL (6.78×10$^{-4}$ mmol) of trifluoromethanesulfonic acid was added thereto. The solution was stirred at room temperature for 15 minutes and cooled to −40° C. 300 mg (0.64 mmol) of Intermediate 24(5) dissolved in 10 mL of dichloromethane was added thereto in a single addition, and the mixture was gradually heated from −40° C. to −30° C. for 30 minutes and heated from −30° C. to 10° C. for 1.5 hours. After the reaction was terminated, 50 mL of a saturated thiosulfate aqueous solution was added thereto, and 50 mL of chloroform was added thereto to separate an organic layer. Then, the organic layer was washed once with 50 ml of the saturated thiosulfate aqueous solution and twice with 50 mL of water. The resultant was dried with magnesium sulfate to evaporate the solvent. The residue was separately purified using silica gel column chromatography to obtain 360 mg (0.60 mmol) of Intermediate 24(6) (Yield: 95%). The produced compound was identified using LC-MS.

C$_{35}$H$_{21}$IN$_2$: M+ 597.07.

G. Synthesis of Compound 24

2.0 g (3.36 mmol) of Intermediate 24(6) and 620 mg (5.03 mmol) of pyridine-4-yl boronic acid were dissolved in 35.0 mL of tetrahydrofuran, and 190 mg (0.17 mmol) of Pd(PPh$_3$)$_4$ and 1.5 mL of a 5 wt % K$_2$CO$_3$ aqueous solution were added thereto, and then the mixture was refluxed while stirring at 120° C. for 24 hours. After the reaction was terminated, the mixture was cooled to room temperature, and then 20.0 mL of distilled water was added thereto to stop the reaction. The resultant was subjected to extraction three times with 70 mL of ethyl acetate to obtain an organic layer. The organic layer was collected and dried with magnesium sulfate to evaporate the solvent. The residue was separately purified using silica gel column chromatography to obtain 860 mg (1.57 mmol) of Intermediate 24 (Yield: 47%). The produced compound was identified using LC-MS and NMR.

C$_{40}$H$_{25}$N$_3$: M+ 548.20.

1H NMR (CDCl$_3$, 400 MHz) δ (ppm) 7.35~7.40 (m, 1H), 7.54~7.59 (m, 3H), 7.77~7.80 (m, 2H), 8.03~8.07 (m, 1H), 8.42~8.45 (m, 1H), 8.52~8.57 (m, 1H), 8.60~8.63 (m, 1H), 8.70 (dd, 1H, J=7.52, J=5.46), 8.76 (dd, 1H, J=5.01, J=4.99), 8.78~9.15 (m, 11H), 9.20 (dd, 1H, J=4.99, J=1.78), 9.34~9.40 (m, 1H)

Synthesis Example 4: Synthesis of Compound 1

Compound 1 was synthesized as in Synthesis Example 1, except that bromobenzene was used instead of 4-bromo-N,N-diphenylamine in the synthesis of Intermediate 6(1), and phenylboronic acid was used instead of dibenzothiophen-1-yl-boronic acid in the synthesis of Intermediate 6(4). The produced compound was identified using LC-MS and NMR.

C$_{19}$H$_{13}$N: M+ 256.10.

1H NMR (CDCl$_3$, 400 MHz) δ (ppm) 7.46~7.49 (m, 2H), 7.51~7.56 (m, 2H), 7.65~7.70 (m, 2H), 7.78~7.85 (m, 2H), 8.05~8.11 (m, 2H), 8.18~8.21 (m, 1H), 8.73 (q, 1H, J=1.58), 9.01~9.03 (dd, 1H, J=1.76)

Synthesis Example 5: Synthesis of Compound 2

Compound 2 was synthesized as in Synthesis Example 3, except that 2-bromo-3-iodopyridine and Intermediate 6(2) were used instead of 2-iodo-3-bromopyridine and Intermediate 24(2) in the synthesis of Intermediate 24(3), phenyl boronic acid was used instead of naphthalen-1-yl-1-boronic acid in the synthesis of Intermediate 24(4), and pyridin-3-yl-3-boronic acid was used instead of pyridin-4-yl-4-boronic acid in the synthesis of Compound 24. The produced compound was identified using LC-MS and NMR.

C$_{36}$H$_{25}$N$_3$: M+ 500.20.

1H NMR (CDCl$_3$, 400 MHz) δ (ppm) 6.99~7.02 (m, 2H), 7.22~7.25 (m, 4H), 7.30~7.34 (m, 2H), 7.39 (d, 1H, J=8.63), 7.40 (d, 1H, J=8.89), 7.56~7.63 (m, 4H), 7.69~7.80 (m, 4H), 8.22~8.26 (m, 2H), 8.34~8.39 (m, 2H), 8.52 (dd, 2H, J=5.20, J=1.89), 8.70~8.73 (m, 1H), 9.05~9.07 (m, 1H)

Synthesis Example 6: Synthesis of Compound 3

Compound 3 was synthesized as in Synthesis Example 1, except that 2-bromopyridine was used instead of 4-bromo-N,N-diphenylamine in the synthesis of Intermediate 6(1), and naphthalen-1-yl-boronic acid was used instead of dibenzothiophen-1-yl-boronic acid in the synthesis of Intermediate 6(4). The produced compound was identified using LC-MS and NMR.

C$_{22}$H$_{14}$N$_2$: M+ 307.12.

1H NMR (CDCl$_3$, 400 MHz) δ (ppm) 7.66~7.72 (m, 2H), 7.77 (q, 1H, J=8.83), 7.96~8.01 (m, 1H), 8.03~8.07 (m, 1H), 8.18~8.25 (m, 2H), 8.27~8.30 (m, 1H), 8.32~8.38 (m, 2H), 8.67 (q, 1H, J=4.85), 8.70~8.72 (m, 1H), 8.74~8.76 (m, 1H), 8.90~8.92 (m, 1H)

Synthesis Example 7: Synthesis of Compound 4

Compound 4 was synthesized as in Synthesis Example 3, except that 2-bromo-3-iodopyridine was used instead of 2-iodo-3-bromopyridine in the synthesis of Intermediate 24(3), and 2-bromothiophene was used instead of pyridin-4-yl-4-boronic acid in the synthesis of Compound 24. The produced compound was identified using LC-MS and NMR.

C$_{39}$H$_{24}$N$_2$S: M+ 553.17.

1H NMR (CDCl$_3$, 400 MHz) δ (ppm) 7.36~7.41 (m, 1H), 7.54~7.59 (m, 2H), 7.61 (t, 1H, J=8.31), 7.78 (dd, 1H, J=7.44, J=1.99), 7.85~7.99 (m, 5H), 8.11 (dd, 1H, J=5.08, J=5.02), 8.22 (dd, 1H, J=5.66, J=1.77), 8.43~8.50 (m, 2H), 8.57~8.62 (m, 1H), 8.68~8.84 (m, 6H), 8.96~8.99 (m, 1H), 9.05~9.10 (m, 1H), 9.23 (q, 1H, J=5.64)

Synthesis Example 8: Synthesis of Compound 5

Compound 5 was synthesized as in Synthesis Example 3, except that 2-bromothiophene was used instead of pyridin-4-yl-4-boronic acid in the synthesis of Compound 24. The produced compound was identified using LC-MS and NMR.

C$_{39}$H$_{24}$N$_2$S: M+ 553.17.

1H NMR (CDCl$_3$, 400 MHz) δ (ppm) 7.38 (t, 1H, J=7.71), 7.53~7.56 (m, 3H), 7.61 (dd, 1H, J=6.59), 7.76~7.78 (m, 2H), 7.91~7.96 (m, 2H), 8.02 (dd, 1H, J=5.02, J=5.02), 8.09~8.12 (m, 1H), 8.23 (dd, 1H, J=5.03, J=1.82), 8.33~8.38 (m, 1H), 8.62~8.70 (m, 3H), 8.78~8.81 (m, 3H), 8.84 (dd, 1H, J=6.08, J=5.10), 8.91~9.25 (m, 4H)

Synthesis Example 9: Synthesis of Compound 7

Compound 7 was synthesized as in Synthesis Example 1, except that 2-bromo-3-iodo-5-fluoropyridine was used instead of 2-bromo-3-iodopyridine in the synthesis of Intermediate 6(3). The produced compound was identified using LC-MS and NMR.

C$_{39}$H$_{24}$N$_2$S: M+ 553.17.

1H NMR (CDCl$_3$, 400 MHz) δ (ppm) 7.38 (t, 1H, J=7.71), 7.53~7.56 (m, 3H), 7.61 (dd, 1H, J=6.59), 7.76~7.78 (m, 2H), 7.91~7.96 (m, 2H), 8.02 (dd, 1H, J=5.02, J=5.02), 8.09~8.12 (m, 1H), 8.23 (dd, 1H, J=5.03, J=1.82), 8.33~8.38 (m, 1H), 8.62~8.70 (m, 3H), 8.78~8.81 (m, 3H), 8.84 (dd, 1H, J=6.08, J=5.10), 8.91~9.25 (m, 4H)

Synthesis Example 10: Synthesis of Compound 8

Compound 8 was synthesized as in Synthesis Example 2, except that 3-iodo-dibenzofuran was used instead of 4-iodo-isoquinoline in the synthesis of Intermediate 12(1), and 3-bromo-2-iodopyridine was used instead of 3-bromo-2-iodo-6-naphthalene-1-yl-pyridine in the synthesis of Intermediate 12(3). The produced compound was identified using LC-MS and NMR.

C$_{24}$H$_{14}$N$_2$O: M+ 347.11.

1H NMR (CDCl$_3$, 400 MHz) δ (ppm) 7.75~7.80 (m, 2H), 7.86~8.02 (m, 5H), 8.34~8.39 (m, 1H), 8.49~8.53 (m, 1H), 8.57~8.62 (m, 1H), 8.75~8.82 (m, 1H), 9.28 (dd, 1H, J=5.01, J=1.79), 9.50~9.54 (m, 1H)

Synthesis Example 11: Synthesis of Compound 9

Compound 9 was synthesized as in Synthesis Example 3, except that 1-methoxy-4-iodo-benzene was used instead of 3-iodo-9-phenyl-9H-carbazole in the synthesis of Intermediate 24(1), quinolin-2-yl-2-boronic acid was used instead of naphthalen-1-yl-1-boronic acid in the synthesis of Intermediate 24(4), and naphthalen-2-yl-2-boronic acid was used instead of pyridin-4-yl-4-boronic acid in the synthesis of Compound 24. The produced compound was identified using LC-MS and NMR.

$C_{33}H_{22}N_2O$: M+ 463.15.

1H NMR (CDCl$_3$, 400 MHz) δ (ppm) 4.15 (s, 3H), 7.21~7.29 (m, 2H), 7.72~7.80 (m, 7H), 8.13~8.20 (m, 3H), 8.24~8.32 (m, 2H), 8.49~8.53 (m, 1H), 8.59~8.73 (m, 3H), 9.50 (dd, 1H, J=5.01, J=1.81)

Synthesis Example 12: Synthesis of Compound 10

Compound 10 was synthesized as in Synthesis Example 3, except that 2-bromo-3-iodopyridine was used instead of 2-iodo-3-bromopyridine in the synthesis of Intermediate 24(3), pyridin-4-yl-4-boronic acid was used instead of naphthalen-1-yl-1-boronic acid in the synthesis of Intermediate 24(4), and 9,9-dimethyl-9H-fluorene-2-yl-2-boronic acid was used instead of pyridin-4-yl-4-boronic acid in the synthesis of Compound 24. The produced compound was identified using LC-MS and NMR.

$C_{45}H_{31}N_3$: M+ 614.25.

1H NMR (CDCl$_3$, 400 MHz) δ (ppm) 2.26 (s, 3H), 7.36~7.41 (m, 1H), 7.56~7.64 (m, 4H), 7.72~7.81 (m, 4H), 7.98~8.01 (m, 2H), 8.10~8.13 (m, 1H), 8.18 (dd, 1H, J=6.22, J=2.01), 8.47 (dd, 1H, J=5.16, J=0.51), 8.70~8.80 (m, 3H), 8.96~9.15 (m, 9H), 9.41 (dd, 1H, J=5.38, J=1.74)

Synthesis Example 13: Synthesis of Compound 11

Compound 11 was synthesized as in Synthesis Example 3, except that 2-bromo-3-iodopyridine was used instead of 2-iodo-3-bromopyridine in the synthesis of Intermediate 24(3), isoquinolin-4-yl-4-boronic acid was used instead of naphthalen-1-yl-1-boronic acid in the synthesis of Intermediate 24(4), and phenyl boronic acid was used instead of pyridin-4-yl-4-boronic acid in the synthesis of Compound 24. The produced compound was identified using LC-MS and NMR.

$C_{45}H_{31}N_3$: M+ 614.25.

1H NMR (CDCl$_3$, 400 MHz) δ (ppm) 2.26 (s, 3H), 7.36~7.41 (m, 1H), 7.56~7.64 (m, 4H), 7.72~7.81 (m, 4H), 7.98~8.01 (m, 2H), 8.10~8.13 (m, 1H), 8.18 (dd, 1H, J=6.22, J=2.01), 8.47 (dd, 1H, J=5.16, J=0.51), 8.70~8.80 (m, 3H), 8.96~9.15 (m, 9H), 9.41 (dd, 1H, J=5.38, J=1.74)

Synthesis Example 14: Synthesis of Compound 13

Compound 13 was synthesized as in Synthesis Example 1, except that pyridin-4-yl-4-boronic acid was used instead of dibenzothiophen-1-yl-boronic acid in the synthesis of Intermediate 6(4). The produced compound was identified using LC-MS and NMR.

$C_{30}H_{21}N$: M+ 424.17

1H NMR (CDCl$_3$, 400 MHz) δ (ppm) 7.20~7.25 (m, 5H), 7.31~7.35 (m, 3H), 7.47 (dd, 2H, J=8.79, J=0.78), 7.58~7.65 (m, 4H), 7.90~7.94 (m, 2H), 8.53 (dd, 1H, J=5.45, J=1.99), 8.70 (dd, 2H, J=5.45, J=1.32), 8.96 (dd, 1H, J=5.22, J=1.66), 9.73~9.77 (m, 1H)

Synthesis Example 15: Synthesis of Compound 14

Compound 14 was synthesized as in Synthesis Example 3, except that 1-methoxy-4-iodo-benzene was used instead of 3-iodo-9-phenyl-9H-carbazole in the synthesis of Intermediate 24(1), 2-bromo-3-iodopyridine was used instead of 2-iodo-3-bromopyridine in the synthesis of Intermediate 24(3), quinolin-2-yl-2-boronic acid was used instead of naphthalene-1-yl-1-boronic acid in the synthesis of Intermediate 24(4), and naphthalen-2-yl-2-boronic acid was used instead of pyridin-4-yl-4-boronic acid in the synthesis of Compound 24. The produced compound was identified using LC-MS and NMR.

$C_{33}H_{22}N_2O$: M+ 463.19.

1H NMR (CDCl$_3$, 400 MHz) δ (ppm) 4.17 (s, 3H), 7.23~7.29 (m, 2H), 7.59~7.75 (m, 3H), 7.80~7.89 (m, 2H), 7.92~8.00 (m, 2H), 8.04 (dd, 1H, J=6.41, J=5.14), 8.26~8.29 (m, 2H), 8.35~8.37 (m, 1H), 8.42~8.43 (m, 1H), 8.47~8.59 (m, 4H), 8.72~8.75 (s, 1H), 9.20 (dd, 1H, J=5.14, J=1.82)

Synthesis Example 16: Synthesis of Compound 15

Compound 15 was synthesized as in Synthesis Example 1, except that 4-bromoisoquinoline was used instead of 4-bromo-N,N-diphenylamine in the synthesis of Intermediate 6(1), 2-bromo-3-iodo-5-fluoropyridine was used instead of 2-bromo-3-iodopyridine in the synthesis of Intermediate 6(3), and pyridin-2-yl-2-boronic acid was used instead of dibenzothiophen-1-yl-boronic acid in the synthesis of Intermediate 6(4). The produced compound was identified using LC-MS and NMR.

$C_{21}H_{12}FN_3$: M+ 326.10.

1H NMR (CDCl$_3$, 400 MHz) δ (ppm) 7.70~7.75 (m, 1H), 7.83 (dd, 1H, J=8.70, J=5.45), 7.96 (ddd, 1H, J=8.09, J=7.66, J=1.76), 8.18~8.22 (m, 2H), 8.29~8.40 (m, 2H), 8.51 (dd, 1H, J=1.83, J=1.76), 8.78 (d, 1H, J=1.83), 8.82 (dd, 1H, J=5.45, J=1.92), 9.40 (dd, 1H, J=5.47, J=1.99), 9.44~9.49 (m, 1H)

Synthesis Example 17: Synthesis of Compound 16

Compound 16 was synthesized as in Synthesis Example 3, except that N-(4-bromophenyl)-N-phenylnaphthalen-1-amine was used instead of 3-iodo-9-phenyl-9H-carbazole in the synthesis of Intermediate 24(1), 2-bromo-3-iodopyridine was used instead of 2-iodo-3-bromopyridine in the synthesis of Intermediate 24(3), benzo[b]thiophen-2-yl-2-boronic acid was used instead of naphthalen-1-yl-1-boronic acid in the synthesis of Intermediate 24(4), and phenyl boronic acid was used instead of pyridin-4-yl-4-boronic acid in the synthesis of Compound 24. The produced compound was identified using LC-MS and NMR.

$C_{43}H_{28}N_2S$: M+ 605.19.

1H NMR (CDCl$_3$, 400 MHz) δ (ppm) 7.19~7.21 (m, 1H), 7.26~7.30 (m, 3H), 7.40~7.43 (m, 1H), 7.54~7.76 (m, 12H), 7.80~7.90 (m, 4H), 8.01~8.06 (m, 1H), 8.29~8.33 (m, 1H), 8.46 (dd, 1H, J=5.05, J=5.04), 8.58 (dd, 1H, J=5.04, J=1.77), 8.66~8.70 (m, 1H), 8.75~8.80 (m, 1H), 9.13 (dd, 1H, J=5.05, J=1.77)

Synthesis Example 18: Synthesis of Compound 17

Compound 17 was synthesized as in Synthesis Example 3, except that 1-bromodibenzofuran was used instead of 3-iodo-9-phenyl-9H-carbazole in the synthesis of Intermediate 24(1), 2-bromo-3-iodopyridine was used instead of 2-iodo-3-bromopyridine in the synthesis of Intermediate 24(3), benzo[b]furan-2-yl-2-boronic acid was used instead of naphthalen-1-yl-1-boronic acid in the synthesis of Intermediate 24(4), and phenyl boronic acid was used instead of pyridin-4-yl-4-boronic acid in the synthesis of Compound 24. The produced compound was identified using LC-MS and NMR.

$C_{33}H_{19}NO_2$: M+ 462.13.

1H NMR (CDCl$_3$, 400 MHz) δ (ppm) 7.68~7.76 (m, 4H), 7.97~8.05 (m, 3H), 8.09~8.12 (m, 1H), 8.16~8.19 (m, 1H), 8.26~8.34 (m, 2H), 8.40~8.49 (m, 2H), 8.52~8.55 (m, 1H), 8.59~8.66 (m, 3H), 8.76 (dd, 1H, J=5.39, J=1.77), 8.80~8.83 (m, 1H), 9.19 (dd, 1H, J=4.96, J=1.77)

Synthesis Example 19: Synthesis of Compound 18

Compound 18 was synthesized as in Synthesis Example 3, except that 2-bromo-3-iodopyridine was used instead of 2-iodo-3-bromopyridine in the synthesis of Intermediate 24(3), and pyriminidin-5-yl-5-boronic acid was used instead of naphthalen-1-yl-1-boronic acid in the synthesis of Intermediate 24(4). The produced compound was identified using LC-MS and NMR.

$C_{34}H_{21}N_5$: M+ 500.15.

1H NMR (CDCl$_3$, 400 MHz) δ(ppm) 7.29~7.39 (m, 3H), 7.83~7.85 (m, 1H), 7.96~8.00 (m, 1H), 8.19 (dd, 1H, J=6.11, J=2.01), 8.22~8.26 (m, 1H), 8.53~8.62 (m, 3H), 8.77~8.80 (m, 1H), 8.85~8.94 (m, 4H), 9.00~9.12 (m, 4H), 9.29 (dd, 1H, J=5.65, J=1.79), 9.53 (d, 1H, J=2.01)

Synthesis Example 20: Synthesis of Compound 19

Compound 19 was synthesized as in Synthesis Example 1, except that 2-iodo-3-bromopyridine was used instead of 2-bromo-3-iodopyridine in the synthesis of Intermediate 6(3), and pyrimidin-5-yl-5-boronic acid was used instead of dibenzothiophen-1-yl-boronic acid in the synthesis of Intermediate 6(4). The produced compound was identified using LC-MS and NMR.

$C_{29}H_{20}H_4$: M+ 425.17.

1H NMR (CDCl$_3$, 400 MHz) δ (ppm) 7.24~7.44 (m, 8H), 7.58~7.72 (m, 6H), 8.04 (dd, 1H, J=7.10, J=5.26), 8.28~8.30 (m, 1H), 8.84 (dd, 1H, J=0.85, J=0.47), 8.92 (d, 1H, J=1.99), 9.05~9.07 (m, 1H), 9.47 (dd, 1H, J=1.99, J=0.76)

Synthesis Example 21: Synthesis of Compound 20

Compound 20 was synthesized as in Synthesis Example 3, except that 3-bromobenzofuran was used instead of 3-iodo-9-phenyl-9H-carbazole in the synthesis of Intermediate 24(1), 2-bromo-3-iodo-5-fluoropyridine was used instead of 2-iodo-3-bromopyridine in the synthesis of Intermediate 24(3), and pyrimidin-5-yl-5-boronic acid was used instead of naphthalen-1-yl-1-boronic acid in the synthesis of Intermediate 24(4), and pyridin-3-yl-3-boronic acid was used instead of pyridin-4-yl-4-boronic acid in the synthesis of Compound 24. The produced compound was identified using LC-MS and NMR.

$C_{24}H_{13}FN_4O$: M+ 393.11.

1H NMR (CDCl$_3$, 400 MHz) δ (ppm) 7.63~7.67 (m, 1H), 7.90~8.00 (m, 3H), 8.15~8.20 (m, 1H), 8.58~8.60 (m, 1H), 8.64 (d, 1H, J=1.69), 8.85~8.90 (m, 1H), 8.95 (d, 1H, J=2.01), 9.04 (d, 1H, J=2.01), 9.33 (dd, 1H, J=5.40, J=5.14), 9.66~9.71 (m, 2H)

Synthesis Example 22: Synthesis of Compound 21

Compound 21 was synthesized as in Synthesis Example 1, except that 3-bromo-1-phenyl-1H-indole was used instead of 4-bromo-N,N-diphenylamine in the synthesis of Intermediate 6(1), and 2-bromo-3-iodo-6-phenyl-pyridine was used instead of 2-bromo-3-iodopyridine in the synthesis of Intermediate 6(3), and pyrimidin-5-yl-5-boronic acid was used instead of dibenzothiophen-1-yl-boronic acid in the synthesis of Intermediate 6(4). The produced compound was identified using LC-MS and NMR.

$C_{31}H_{20}N_4$: M+ 449.17.

1H NMR (CDCl$_3$, 400 MHz) δ (ppm) 7.54~7.57 (m, 1H), 7.76~7.96 (m, 10H), 8.24~8.31 (m, 1H), 8.50~8.59 (m, 2H), 8.68 (dd, 1H, J=6.26, J=1.77), 8.93 (dd, 1H, J=5.34, J=1.77), 9.02 (d, 1H, J=2.01), 9.20 (dd, 1H, J=6.26, J=5.34), 9.39 (dd, 1H, J=5.09, J=4.69), 9.50 (d, 1H, J=2.01)

Synthesis Example 23: Synthesis of Compound 22

Compound 22 was synthesized as in Synthesis Example 3, except that 3-bromobenzothiophene was used instead of 3-iodo-9-phenyl-9H-carbazole in the synthesis of Intermediate 24(1), 2-iodo-3-bromo-5-phenylpyridine was used instead of 2-iodo-3-bromopyridine in the synthesis of Intermediate 24(3), and pyrimidin-5-yl-5-boronic acid was used instead of naphthalen-1-yl-1-boronic acid in the synthesis of Intermediate 24(4), and naphthalen-2-yl-2-boronic acid was used instead of pyridin-4-yl-4-boronic acid in the synthesis of Compound 24. The produced compound was identified using LC-MS and NMR.

$C_{39}H_{23}N_3S$: M+ 566.16.

1H NMR (CDCl$_3$, 400 MHz) δ (ppm) 7.68~7.72 (m, 1H), 7.90~7.95 (m, 3H), 8.03~8.11 (m, 2H), 8.18 (dd, 1H, J=7.76, J=2.00), 8.47~8.51 (m, 1H), 8.59~8.75 (m, 6H), 8.80 (dd, 1H, J=4.79, J=1.78), 8.90~9.01 (m, 3H), 9.13~9.16 (m, 1H), 9.24~9.26 (m, 2H), 9.35~9.40 (m, 2H), 9.69 (d, 1H, J=1.78)

Synthesis Example 24: Synthesis of Compound 23

Compound 23 was synthesized in the same manner as in Synthesis Example 3, except that 4-bromo-N,N-diphenylamine was used instead of 3-iodo-9-phenyl-9H-carbazole in the synthesis of Intermediate 24(1), 2-bromo-3-iodopyridine was used instead of 2-iodo-3-bromopyridine in the synthesis of Intermediate 24(3), pyrimidin-5-yl-5-boronic acid was used instead of naphthalen-1-yl-1-boronic acid in the synthesis of Intermediate 24(4), and deuterated phenyl-boronic acid was used instead of pyridin-4-yl-4-boronic acid in the synthesis of Compound 24. The produced compound was identified using LC-MS and NMR.

$C_{35}H_{19}D_5N_4$: M+ 506.23.

1H NMR (CDCl$_3$, 400 MHz) δ (ppm) 724~7.27 (m, 4H), 7.32~7.35 (m, 2H), 7.44~7.52 (m, 3H), 7.58~7.64 (m, 4H), 7.72~7.83 (m, 5H), 7.89~7.91 (m, 1H), 8.50 (dd, 1H, J=8.49, J=1.69), 9.00 (d, 1H, J=1.83), 9.30 (dd, 1H, J=5.12, J=1.69), 9.44 (d, 1H, J=1.83)

Synthesis Example 25: Synthesis of Compound 25

Compound 25 was synthesized as in Synthesis Example 1, except that N-4(-bromophenyl)-N-phenylnaphthalen-1-amine was used instead of 4-bromo-N,N-diphenylamine in the synthesis of Intermediate 6(1), and 2-bromo-3-iodo-4-phenyl-pyridine was used instead of 2-bromo-3-iodopyridine in the synthesis of Intermediate 6(3). The produced compound was identified using LC-MS and NMR.

$C_{47}H_{30}H_2S$: M+ 655.22.

1H NMR (CDCl$_3$, 400 MHz) δ (ppm) 7.19~7.35 (m, 6H), 7.39~7.46 (m, 2H), 7.53~7.62 (m, 2H), 7.65~7.89 (m, 9H), 8.20~8.28 (m, 2H), 8.32~8.38 (m, 2H), 8.52 (dd, 1H, J=5.47, J=5.12), 8.74 (dd, 1H, J=6.49, J=5.37), 8.83 (dd, 1H, J=6.49, J=4.98), 8.88~8.90 (m, 1H), 8.98~9.02 (m, 1H), 9.22 (d, 1H, J=5.12), 9.24 (dd, 1H, J=5.47)

Example 1

An anode was prepared by cutting a Corning 15 Ω/cm² (120 nm) ITO glass substrate to a size of 50 mm×50 mm×0.7 mm, ultrasonically cleaning the glass substrate using isopropyl alcohol and pure water for five minutes each, irradiating the substrate with UV light for 30 minutes, and exposing the substrate to ozone to clean. Then, the glass substrate was disposed in a vacuum deposition apparatus.

2-TNATA was deposited on an ITO layer (anode) on the glass substrate to form an HIL having a thickness of 600 Å, and then 4,4'-bis[N-(1-naphthyl)-N-phenylamino]biphenyl (NPB) was deposited on the HIL to form an HTL having a thickness of 300 Å.

Then, ADN, as a host, and Compound 18, as a dopant, were co-deposited on the HTL at a weight ratio of 98:2 to form an EML with a thickness of 300 Å.

Then, Alq₃ was deposited on the EML to form an ETL having a thickness of 300 Å, and LiF was deposited on the ETL to form an EIL having a thickness of 10 Å. Then, Al was deposited on the EIL to a thickness of 3000 Å, thereby forming a second electrode (cathode). As a result, an organic light-emitting diode (emitting blue light) was prepared.

Example 2

An organic light-emitting diode was manufactured as in Example 1, except that Compound 40 was used instead of Compound 18 in the formation of the EML.

Example 3

An organic light-emitting diode was manufactured as in Example 1, except that Compound 68 was used instead of Compound 18 in the formation of the EML.

Comparative Example 1

An organic light-emitting diode was manufactured as in Example 1, except that DPVBi was used instead of Compound 18 in the formation of the EML.

Example 4

An organic light-emitting diode (emitting green light) was manufactured as in Example 1, except that Compound 3 was used instead of ADN as the host of the EML, Ir(ppy)₃ was used instead of Compound 18 as the dopant, and BCP was deposited between the EML and the ETL to form an HBL with a thickness of 50 Å.

Example 5

An organic light-emitting diode was manufactured as in Example 4, except that Compound 26 was used instead of Compound 3 in the formation of the EML.

Example 6

An organic light-emitting diode was manufactured as in Example 3, except that Compound 29 was used instead of Compound 3 in the formation of the EML.

Comparative Example 2

An organic light-emitting diode was manufactured as in Example 1, except that CBP was used instead of Compound 3 in the formation of the EML.

Comparative Example 3

An organic light-emitting diode was manufactured as in Example 1, except that Compound A was used instead of Compound 3 in the formation of the EML.

Compound A

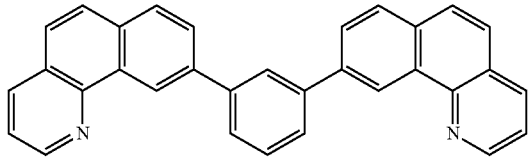

Compound A was synthesized via the following Reaction Scheme.

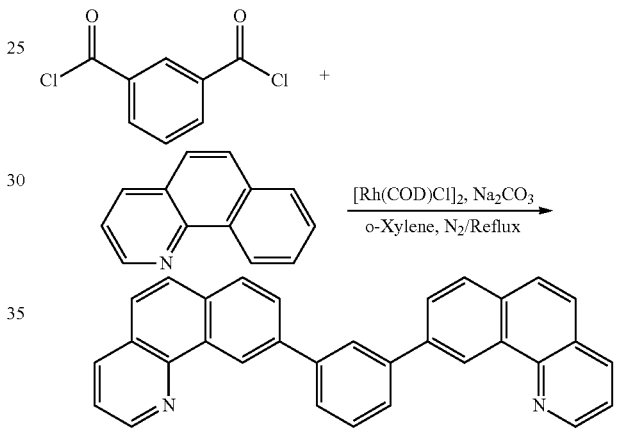

25 mg (0.05 mmol) of [Rh(COD)Cl]₂ and 213 mg (2.0 mmol) of Na₂CO₃ were added to a 25 mL flask filled with nitrogen, and then 1.0 g of 4 Å molecular sieves, 224 mg (1.25 mmol) of benzo[h]quinoline, 100 mg (0.5 mmol) of isophthaloyl dichloride, and 5 mL of o-xylene were sequentially added thereto. The flask was refluxed at 145° C. for 36 hours while stirring, and then cooled to room temperature. The resultant was filtered using a celite pad, and the celite pad was washed with 20 mL of toluene and dried to evaporate the solvent. The residue was separately purified using silica gel column chromatography to obtain 96 mg (0.22 mmol) of Compound A (Yield: 44%). The produced compound was identified using LC-MS and NMR.

$C_{47}H_{30}N_2S$: M+ 433.16.

1H NMR (CDCl₃, 400 MHz) δ (ppm) 7.81~7.88 (m, 3H), 7.96 (dd, 1H, J=8.19, J=7.55), 8.06~8.11 (m, 1H), 8.14~8.24 (m, 3H), 8.32~8.34 (m, 2H), 8.36~8.48 (m, 5H), 8.53~8.55 (m, 1H), 8.70~8.76 (m, 3H), 9.18 (dd, 1H, J=5.10, J=1.74), 9.22 (dd, 1H, J=5.10, J=1.64)

Evaluation Example 1

The driving voltage, current density, brightness, color of emitted light, efficiency, and lifespan of the organic light-emitting diodes manufactured according to Examples 1 to 6 and Comparative Examples 1 to 3 were evaluated using a PR650 Spectroscan Source Measurement Unit (Photo-Reaserch). The results are shown in Table 1 below.

TABLE 1
| | EML | | Driving voltage (V) | Current Density (mA/cm$^2$) | Brightness (Cd/m$^2$) | Efficiency (Cd/A) | Color | Life-span (hr) |
| --- | --- | --- | --- | --- | --- | --- | --- | --- |
| | Host | Dopant | | | | | | |
| Ex. 1 | ADN | Comp. 6 | 6.2 | 50 | 2,579 | 5.16 | blue | 30 |
| Ex. 2 | ADN | Comp. 16 | 5.9 | 50 | 2,376 | 4.75 | blue | 38 |
| Ex. 3 | ADN | Comp. 25 | 5.7 | 50 | 2,671 | 5.34 | blue | 34 |
| Comp. Ex. 1 | ADN | DPVBi | 7.5 | 50 | 1,522 | 3.04 | blue | 15 |
| Ex. 4 | Comp. 2 | Ir(ppy)$_3$ | 5.2 | 50 | 18,729 | 37.5 | green | 101 |
| Ex. 5 | Comp. 12 | Ir(ppy)$_3$ | 5.1 | 50 | 16,581 | 33.2 | green | 92 |
| Ex. 6 | Comp. 14 | Ir(ppy)$_3$ | 5.4 | 50 | 18,052 | 36.1 | green | 104 |
| Comp. Ex. 2 | CBP | Ir(ppy)$_3$ | 6.8 | 50 | 10,902 | 21.8 | green | 60 |
| Comp. Ex. 3 | Comp. A | Ir(ppy)$_3$ | 7.0 | 50 | 12,153 | 24.3 | green | 57 |
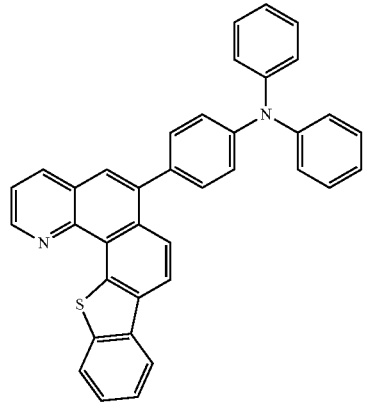
6
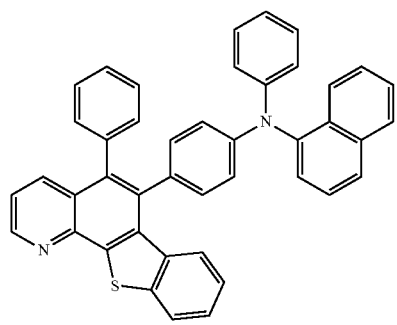
16

TABLE 1-continued
| | EML | | Driving voltage | Current Density | Brightness | Efficiency | | Life-span |
|---|---|---|---|---|---|---|---|---|
| | Host | Dopant | (V) | (mA/cm$^2$) | (Cd/m$^2$) | (Cd/A) | Color | (hr) |
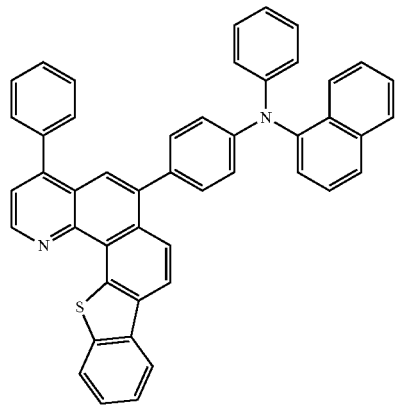
25
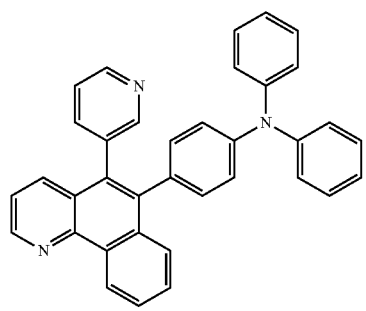
2
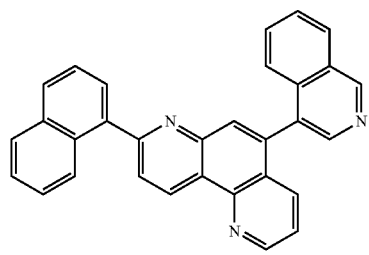
12
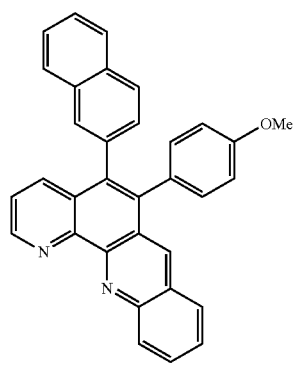
14

The lifespan shown in Table 1 is the time at which the brightness of each of the OLEDs decreased to 97% of the initial brightness (measured at a constant current of 10 mA/cm$_2$).

Referring to Table 1, the organic light-emitting diodes manufactured according to Examples 1 to 3 had lower driving voltages, higher brightness, better efficiency, better color purity, and longer lifespans than the organic light-emitting diode manufactured according to Comparative Example 1. Also, the organic light-emitting diodes manufactured according to Examples 4 to 6 had lower driving voltages, higher brightness, better efficiency, better color purity, and longer lifespans than the organic light-emitting diodes manufactured according to Comparative Examples 2 and 3. Organic light-emitting diodes including the condensed-cyclic compounds according to embodiments of the present invention may have low driving voltages, high brightness, high efficiency, and long lifespans.

While the present invention has been illustrated and described with reference to certain exemplary embodiments, it will be understood by those of ordinary skill in the art that various changes and modifications may be made to the described embodiments without departing from the spirit and scope of the present invention as defined by the following claims.

What is claimed is:

1. A condensed-cyclic compound represented by Formula 1:

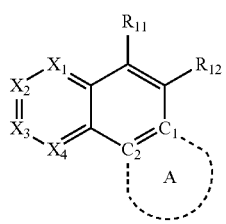

Formula 1 wherein:
$X_1$ is N or $C(R_1)$, $X_2$ is N or $C(R_2)$, $X_3$ is N or $C(R_3)$, and $X_4$ is N or $C(R_4)$, wherein at least one of $X_1$ through $X_4$ is N;

ring A is a substituted or unsubstituted naphthalene, a substituted or unsubstituted pyrimidine, a substituted or unsubstituted isoquinoline, a substituted or unsubstituted benzothiophene, a substituted or unsubstituted benzofuran, a substituted or unsubstituted dibenzothiophene, or a substituted or unsubstituted dibenzofuran;

each of $R_1$ through $R_4$, $R_{11}$ and $R_{12}$ is independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —Si($R_{31}$)($R_{32}$)($R_{33}$), or —N($R_{34}$)($R_{35}$); and each of $R_{31}$ through $R_{35}$ is independently a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group; and at least one of $R_{11}$ or $R_{12}$ is a substituted or unsubstituted $C_3$-$C_{60}$ cycloalkyl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted phenyl group, a substituted or unsubstituted pentalenyl group, a substituted or unsubstituted indenyl group, a substituted or unsubstituted naphthyl group, a substituted or unsubstituted anthracenyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted phenalenyl group, a substituted or unsubstituted anthraquinolyl group, a substituted or unsubstituted fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentacenyl group, a substituted or unsubstituted tetraphenylenyl group, a hexaphenyl group, a substituted or unsubstituted rubicenyl group, a substituted or unsubstituted coronenyl group, a substituted or unsubstituted trinaphthylenyl group, a substituted or unsubstituted heptaphenyl group, a substituted or unsubstituted heptacenyl group, a substituted or unsubstituted pyranthrenyl group, a substituted or unsubstituted ovalenyl group, or a substituted or unsubstituted hexacenyl group.

2. The condensed-cyclic compound of claim 1, wherein $X_1$ is $C(R_1)$, $X_2$ is $C(R_2)$, $X_3$ is $C(R_3)$, and $X_4$ is N.

3. The condensed-cyclic compound of claim 1, wherein $X_1$ is N, $X_2$ is $C(R_2)$, $X_3$ is $C(R_3)$, and $X_4$ is $C(R_4)$.

4. The condensed-cyclic compound of claim 1, wherein each of $R_1$ through $R_4$ is independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{10}$ alkyl group, a substituted or unsubstituted $C_1$-$C_{10}$ alkoxy group, a substituted or unsubstituted $C_6$-$C_{14}$ aryl group, or a substituted or unsubstituted $C_2$-$C_{14}$ heteroaryl group.

5. The condensed-cyclic compound of claim 1, wherein each of $R_1$ through $R_4$ is independently a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkyl group or a $C_1$-$C_{10}$ alkoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, or a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, or a chrysenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a fluoro-$C_1$-$C_{10}$ alkyl group, and a $C_1$-$C_{10}$ alkoxy group; an indolyl group; a benzoimidazolyl group; a carbazolyl group; an imidazolyl group; an imidazolinyl group; an imidazopyridinyl group; an imidazopyrimidinyl group; a pyridinyl group; a pyrimidinyl group; a triazinyl group; a quinolinyl group; an indolyl group, a benzoimidazolyl group, a carbazolyl group, an imidazolyl group, an imidazolinyl group, an imidazopyridinyl group, an imidazopyrimidinyl group, a pyridinyl group, a pyrimidinyl group, a triazinyl group, or a quinolinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a fluoro-$C_1$-$C_{10}$ alkyl group, a $C_1$-$C_{10}$ alkoxy group, a phenyl group, or a naphthyl group.

6. The condensed-cyclic compound of claim 1, wherein each of $R_1$ through $R_4$ is independently a hydrogen atom, a deuterium atom, a halogen atom, a cyano group, a methyl group, an ethyl group, a propyl group, a butyl group, a pentyl group, a methoxy group, an ethoxy group, a propoxy group, a butoxy group, a pentoxy group, a phenyl group, or a naphthyl group.

7. The condensed-cyclic compound of claim 1 wherein:
ring A is selected from Formulae 2B, 2E, 2G, 2H and 2I below:

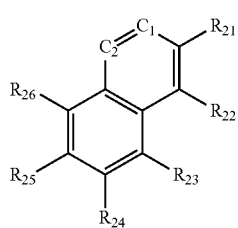

Formula 2B

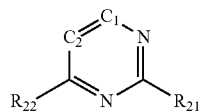

Formula 2E

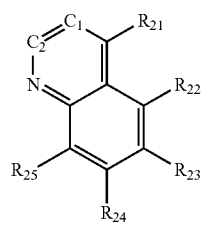

Formula 2F

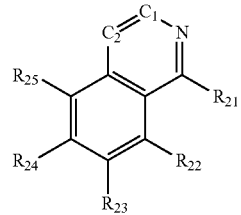

Formula 2G

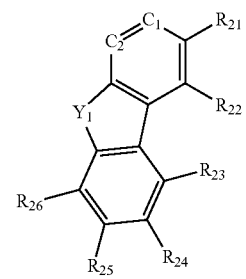

Formula 2I wherein each of $R_{21}$ through $R_{26}$ is independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, or a substituted or unsubstituted $C_6$-$C_{60}$ aryloxy group, or a substituted or unsubstituted $C_6$-$C_{60}$ arylthio group; and
$Y_1$ is S or O.

8. The condensed-cyclic compound of claim 7, wherein ring A is represented by Formula 2H or 2I.

9. The condensed-cyclic compound of claim 7, wherein in Formulae 2B, 2E, 2G, 2H and 2I, each of $R_{21}$ through $R_{26}$ is independently a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkyl group or a $C_1$-$C_{10}$ alkoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, or a chrysenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group; an indolyl group; a benzoimidazolyl group; a carbazolyl group; an imidazolyl group; an imidazolinyl group; an imidazopyridinyl group; an imidazopyrimidinyl group; a pyridinyl group; a pyrimidinyl group; a triazinyl group; a quinolinyl group; and an indolyl group, a benzoimidazolyl group, a carbazolyl group, an imidazolyl group, an imidazolinyl group, an imidazopyridinyl group, an imidazopyrimidinyl group, a pyridinyl group, a pyrimidinyl group, a triazinyl group, or a quinolinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, or a naphthyl group.

10. The condensed-cyclic compound of claim 7, wherein in each of Formulae 2B, 2E, 2G, 2H and 2I, each of $R_{21}$ through $R_{26}$ is a hydrogen atom.

11. The condensed-cyclic compound of claim 1, wherein:
    $R_{11}$ and $R_{12}$ are each independently selected from a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ alkoxy group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentacenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted indolyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzofuranyl group, a substituted or unsubstituted triazinyl group, or a substituted or unsubstituted oxadiazolyl group; and at least one of $R_{11}$ or $R_{12}$ is a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentacenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted indolyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzofuranyl group, a substituted or unsubstituted triazinyl group, or a substituted or unsubstituted oxadiazolyl group.

12. The condensed-cyclic compound of claim 1, wherein:
    $R_{11}$ and $R_{12}$ are each independently selected from a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{10}$ alkyl group, a substituted or unsubstituted $C_1$-$C_{10}$ alkoxy group, or a group represented by one of Formulae 3A through 3P; and at least one of $R_{11}$ or $R_{12}$ is a group represented by one of Formulae 3A through 3P:

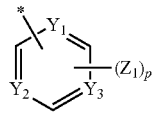

Formula 3A

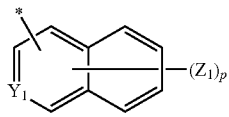

Formula 3B

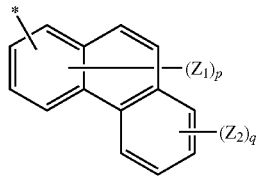

Formula 3C

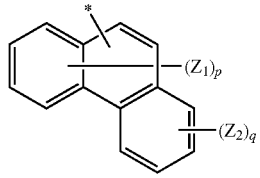

Formula 3D

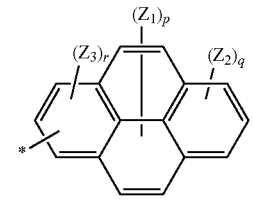

Formula 3E

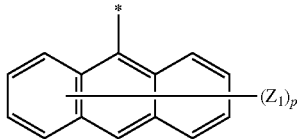

Formula 3F

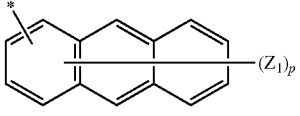

Formula 3G

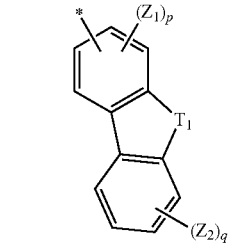

Formula 3H

-continued

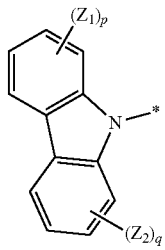

Formula 3I

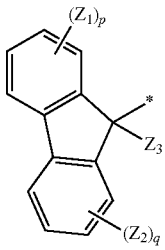

Formula 3J

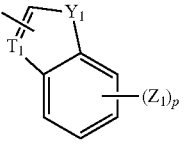

Formula 3K

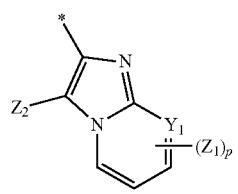

Formula 3L

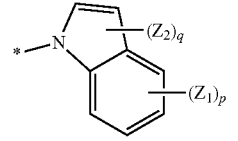

Formula 3M

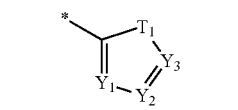

Formula 3N

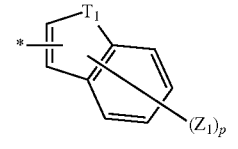

Formula 3O

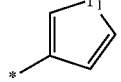

Formula 3P wherein:

each of $Y_1$ through $Y_3$ is independently =N— or =C($Z_{11}$)—;

$T_1$ is —S—, —O—, —N($Z_{12}$)—, or —C($Z_{13}$)($Z_{14}$)—;

each of $Z_1$ through $Z_3$ and $Z_{11}$ through $Z_{14}$ is independently a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ cycloalkyl group; a $C_6$-$C_{60}$ aryl group; a $C_6$-$C_{60}$ aryloxy group; a $C_6$-$C_{60}$ arylthio group; a $C_2$-$C_{60}$ heteroaryl group; a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_6$-$C_{60}$ aryl group, a $C_6$-$C_{60}$ aryloxy group, a $C_6$-$C_{60}$ arylthio group, or a $C_2$-$C_{60}$ heteroaryl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group; —N($Q_{11}$)($Q_{12}$); or —Si($Q_{13}$)($Q_{14}$)($Q_{15}$);

wherein each of $Q_{11}$ through $Q_{15}$ is independently a $C_3$-$C_{60}$ cycloalkyl group; a $C_6$-$C_{60}$ aryl group; a $C_6$-$C_{60}$ aryloxy group; a $C_6$-$C_{60}$ arylthio group; a $C_2$-$C_{60}$ heteroaryl group; or a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_6$-$C_{60}$ aryl group, a $C_6$-$C_{60}$ aryloxy group, a $C_6$-$C_{60}$ arylthio group, or a $C_2$-$C_{60}$ heteroaryl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

p is an integer from 1 to 9;
q is an integer from 1 to 4; and
r is an integer from 1 to 3.

13. The condensed-cyclic compound of claim 12, wherein each of $Z_1$ through $Z_3$ and $Z_{11}$ through $Z_{14}$ is independently a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a methyl group; an ethyl group; a propyl group; a butyl group; a pentyl group; a methoxy group; an ethoxy group; a propoxy group; a butoxy group; a pentoxy group; a methyl group, an ethyl group, a propyl group, a butyl group, a pentyl group, a methoxy group, an ethoxy group, a propoxy group, a butoxy group, or a pentoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, or a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, or a chrysenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, a propyl group, a butyl group, a pentyl group, a methoxy group, an ethoxy group, a propoxy group, a butoxy group, or a pentoxy group; a carbazolyl group; an imidazolyl group; an imidazolinyl group; an imidazopyridinyl group; an imidazopyrimidinyl group; a pyridinyl group; a pyrimidinyl group; a triazinyl group; a quinolinyl group; a carbazolyl group, an imidazolyl group, an imidazolinyl group, an imidazopyridinyl group, an imidazopyrimidinyl group, a pyridinyl group, a pyrimidinyl group, a triazinyl group, or a quinolinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, a propyl group, a butyl group, a pentyl group, a methoxy group, an ethoxy group, a propoxy group, a butoxy group, or a pentoxy group; or —N($Q_{11}$)($Q_{12}$), wherein each of $Q_{11}$ and $Q_{12}$ is independently a phenyl group; a naphthyl group; a fluorenyl group; a phenanthrenyl group; an anthryl group; a pyrenyl group; a chrysenyl group; or a phenyl group, a naphthyl group, a fluorenyl group, a phenanthrenyl group, an anthryl group, a pyrenyl group, or a chrysenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, a propyl group, a butyl group, a pentyl group, a methoxy group, an ethoxy group, a propoxy group, a butoxy group, or a pentoxy group.

14. The condensed-cyclic compound of claim 1, wherein:
$R_{11}$ and $R_{12}$ are each independently selected from a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, or a group represented by one of Formulae 4-1 through 4-49; and
at least one of $R_{11}$ or $R_{12}$ is a group represented by one of Formulae 4-1 through 4-49:

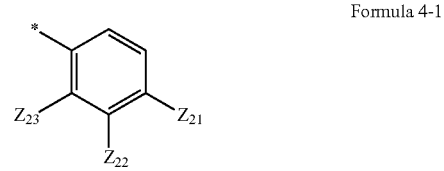

Formula 4-1

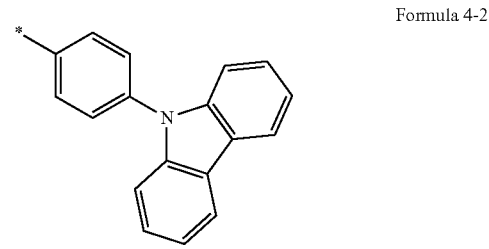

Formula 4-2

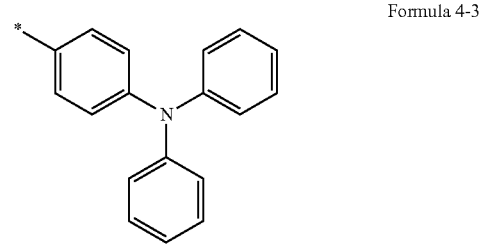

Formula 4-3

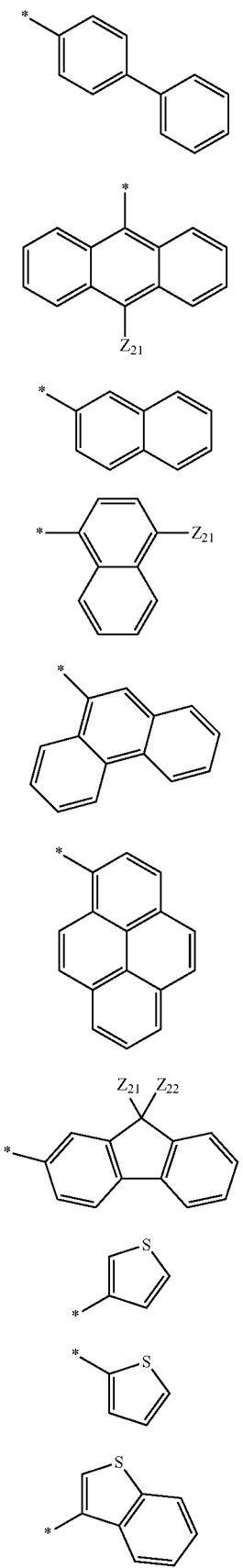
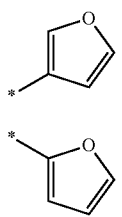
Formula 4-4
Formula 4-5
Formula 4-6
Formula 4-7
Formula 4-8
Formula 4-9
Formula 4-10
Formula 4-11
Formula 4-12
Formula 4-13
Formula 4-14
Formula 4-15
Formula 4-16
Formula 4-17
Formula 4-18
Formula 4-19
Formula 4-20
Formula 4-21
Formula 4-22

-continued
Formula 4-23
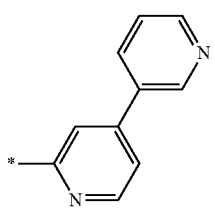
Formula 4-24
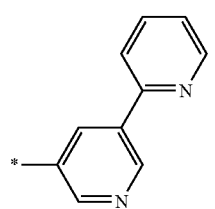
Formula 4-25
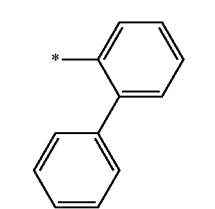
Formula 4-26
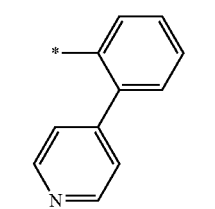
Formula 4-27
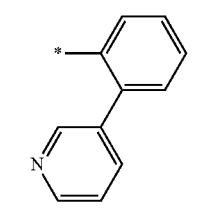
Formula 4-28
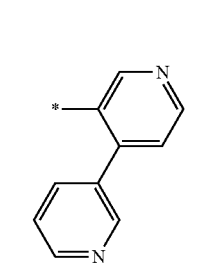
Formula 4-29
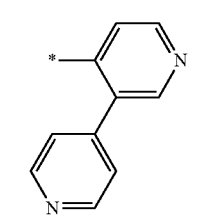
-continued
Formula 4-30
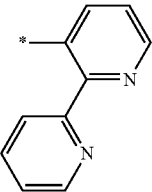
Formula 4-31
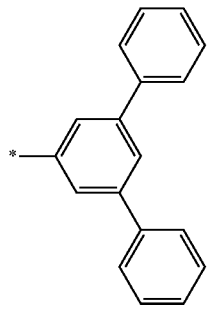
Formula 4-32
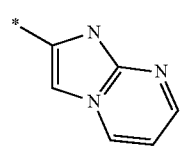
Formula 4-33
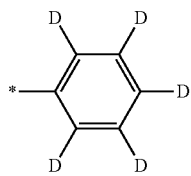
Formula 4-34
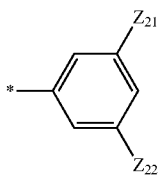
Formula 4-35
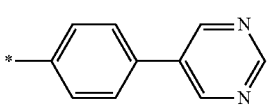
Formula 4-36
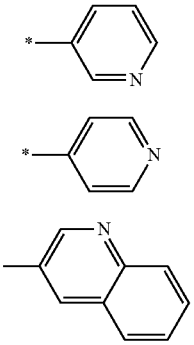
Formula 4-37
Formula 4-38
Formula 4-39
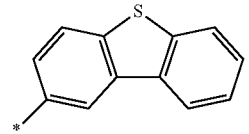

-continued

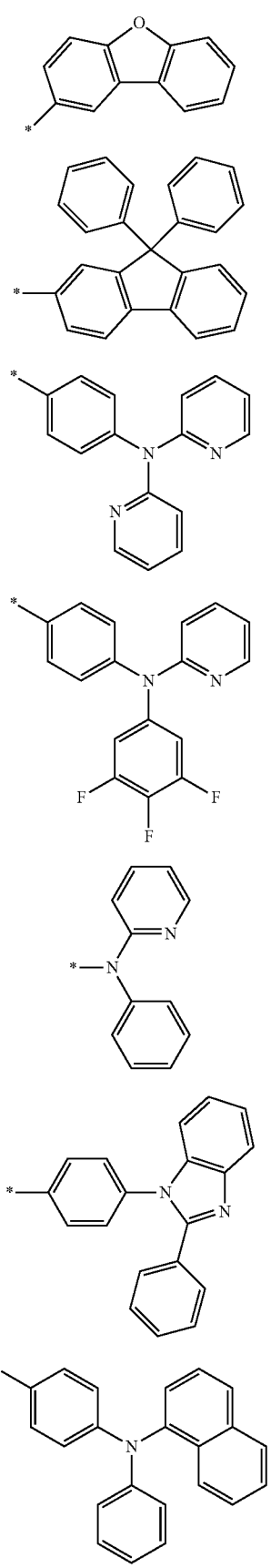

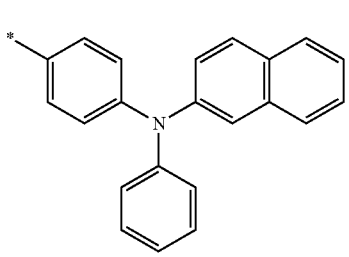

Formula 4-47

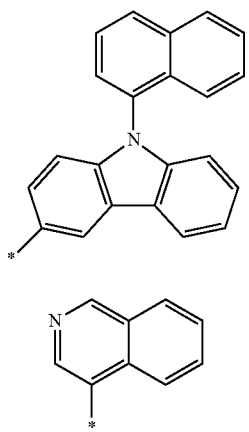

Formula 4-48

Formula 4-49 wherein each of $Z_{21}$ through $Z_{23}$ is independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, a propyl group, a butyl group, a pentyl group, a methoxy group, an ethoxy group, a propoxy group, a butoxy group, and a pentoxy group; or a methyl group, an ethyl group, a propyl group, a butyl group, a pentyl group, a methoxy group, an ethoxy group, a propoxy group, a butoxy group, or a pentoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, or a phosphoric acid group or a salt thereof.

15. A condensed-cyclic compound represented by one of Formulae 1C, 1D or 1E:

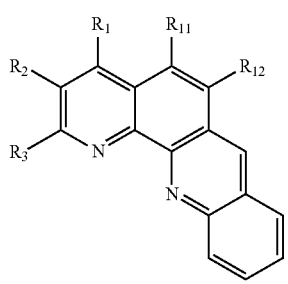

Formula 1C

-continued

Formula 1D

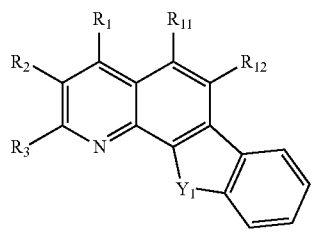

Formula 1E

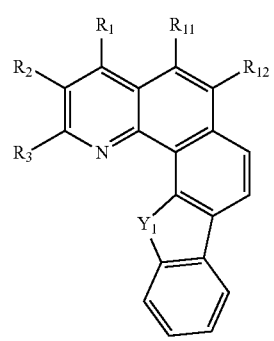

wherein:

Y$_1$ is S or O, each of R$_1$ through R$_3$ is independently a hydrogen atom, a deuterium atom, a halogen atom, a cyano group, a methyl group, an ethyl group, a propyl group, a butyl group, a pentyl group, a methoxy group, an ethoxy group, a propoxy group, a butoxy group, a pentoxy group, a phenyl group, or a naphthyl group, R$_{11}$ and R$_{12}$ are each independently selected from a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a C$_1$-C$_{10}$ alkyl group, a C$_1$-C$_{10}$ alkoxy group, or a group represented by one of Formulae 4-1 through 4-49; and at least one of R$_{11}$ and R$_{12}$ is a group represented by one of Formulae 4-1 through 4-49:

Formula 4-1

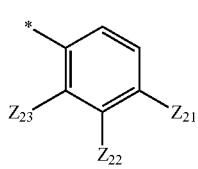

Formula 4-2

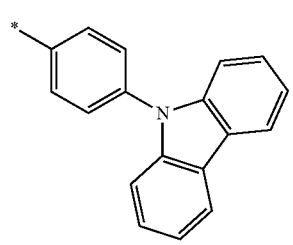

-continued

Formula 4-3

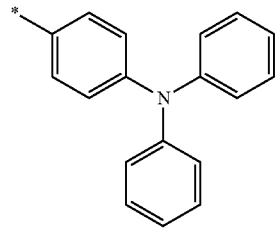

Formula 4-4

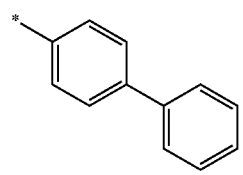

Formula 4-5

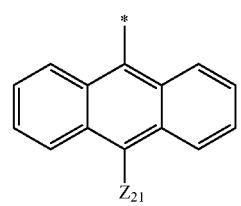

Formula 4-6

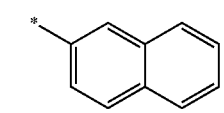

Formula 4-7

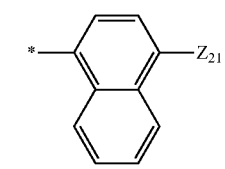

Formula 4-8

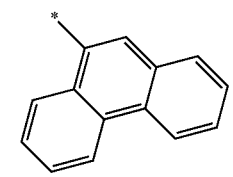

Formula 4-9

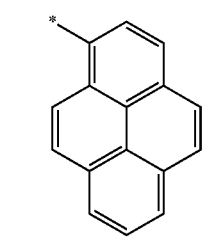

Formula 4-10

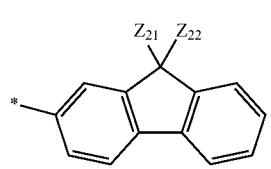

Formula 4-11

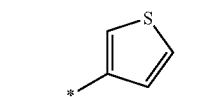

| | |
|---|---|
| Formula 4-12 | Formula 4-22 |
| Formula 4-13 | Formula 4-23 |
| Formula 4-14 | Formula 4-24 |
| Formula 4-15 | Formula 4-25 |
| Formula 4-16 | Formula 4-26 |
| Formula 4-17 | Formula 4-27 |
| Formula 4-18 | Formula 4-28 |
| Formula 4-19 | |
| Formula 4-20 | |
| Formula 4-21 | |

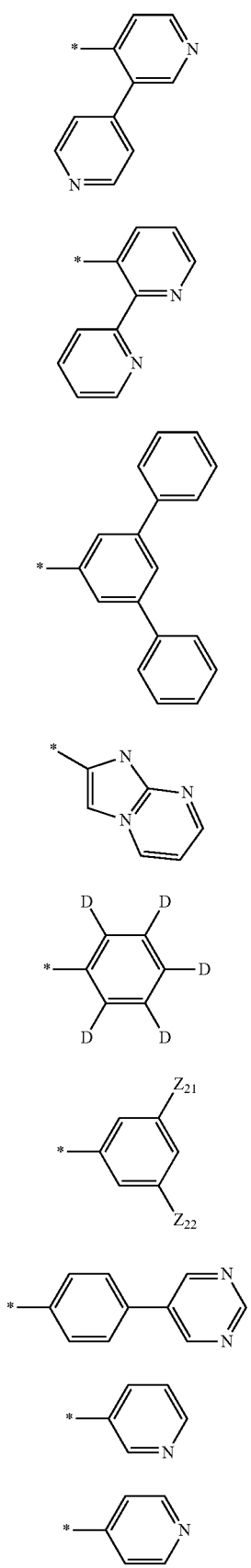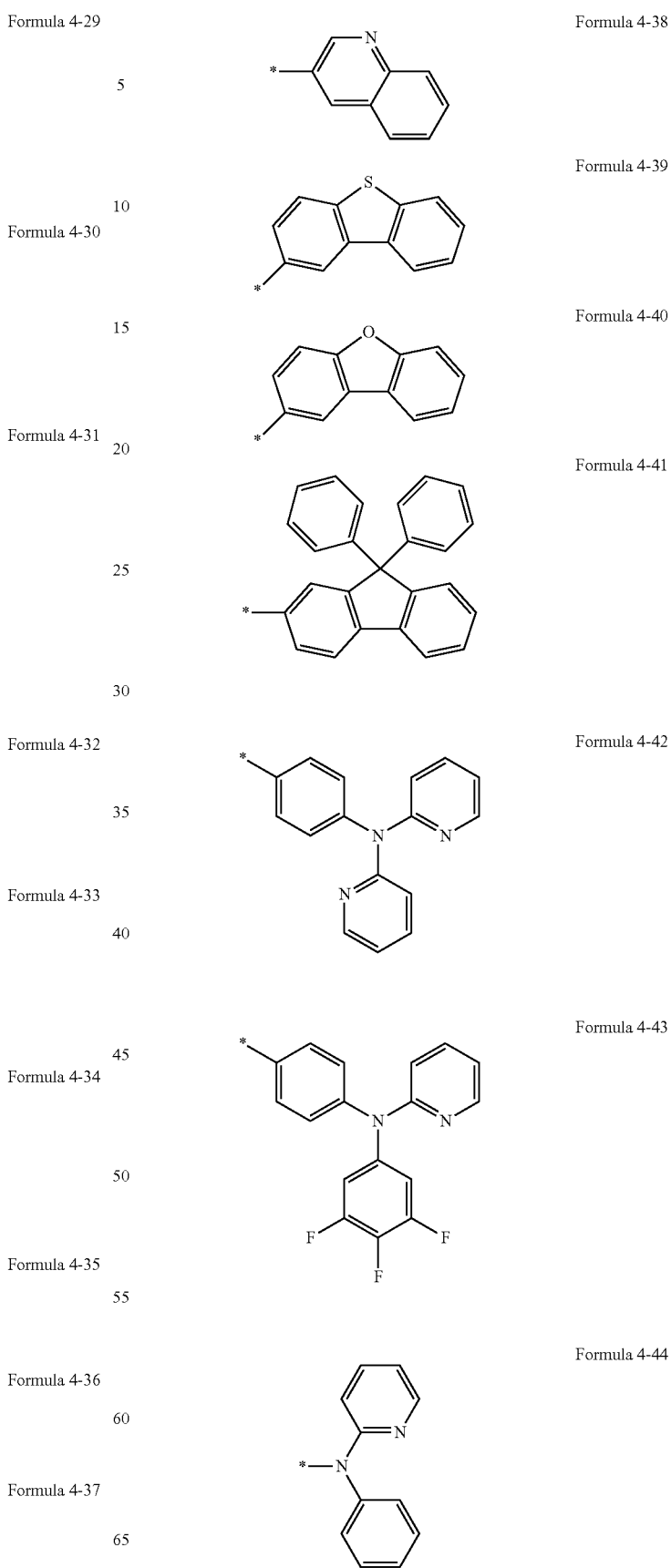

-continued

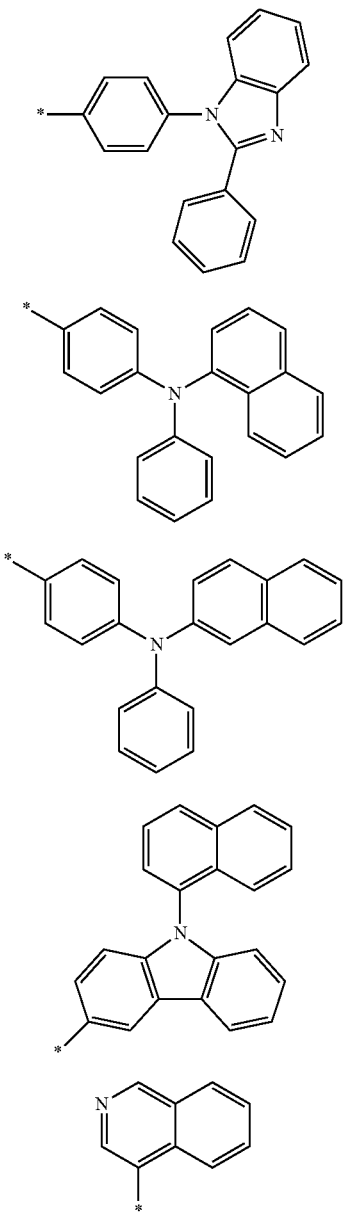

Formula 4-45

Formula 4-46

Formula 4-47

Formula 4-48

Formula 4-49 wherein each of $Z_{21}$ through $Z_{23}$ is independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, a propyl group, a butyl group, a pentyl group, a methoxy group, an ethoxy group, a propoxy group, a butoxy group, or a pentoxy group; or a methyl group, an ethyl group, a propyl group, a butyl group, a pentyl group, a methoxy group, an ethoxy group, a propoxy group, a butoxy group, or a pentoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, or a phosphoric acid group or a salt thereof.

16. A condensed-cyclic compound represented by one of Compounds 3 through 7, 9, 11, 14 and 16 through 25:

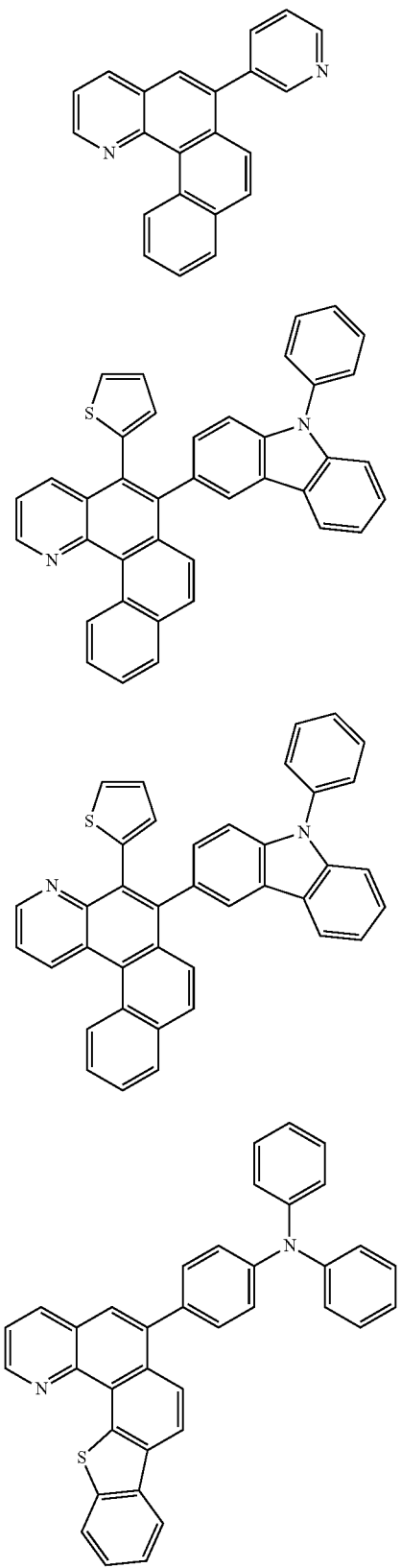

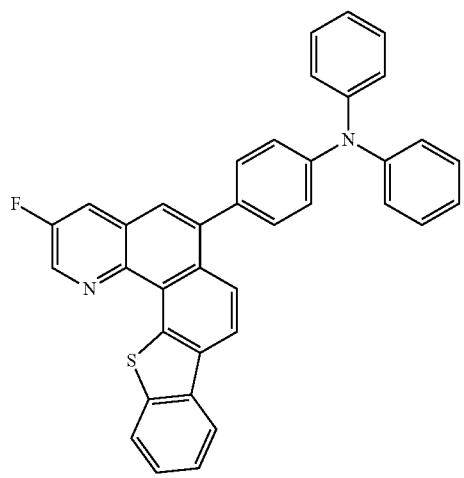
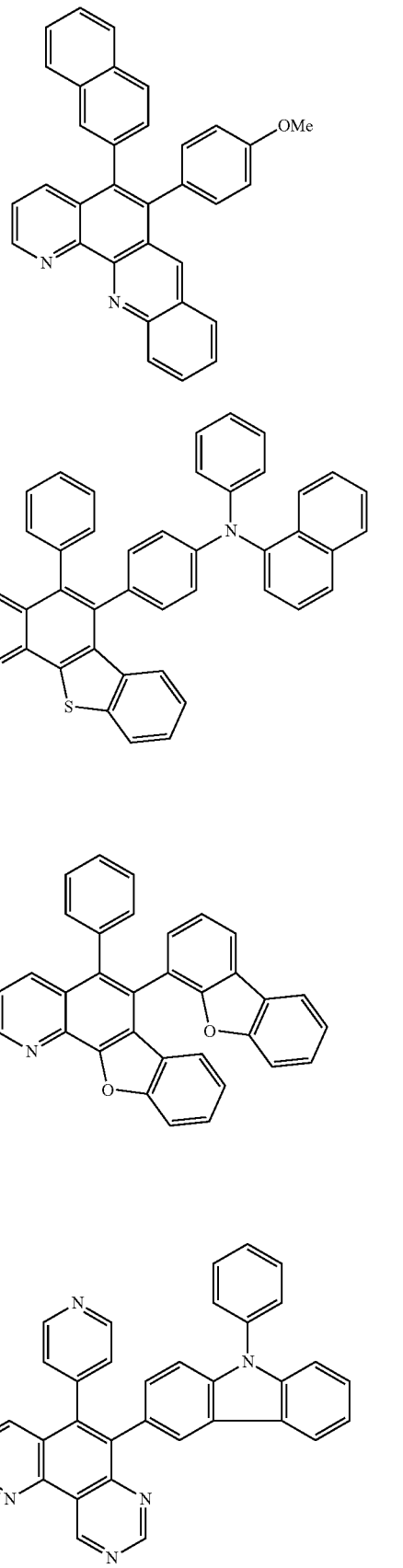

19
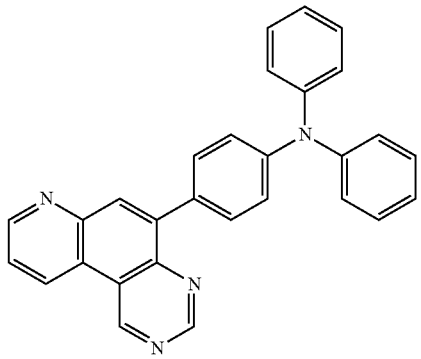

20
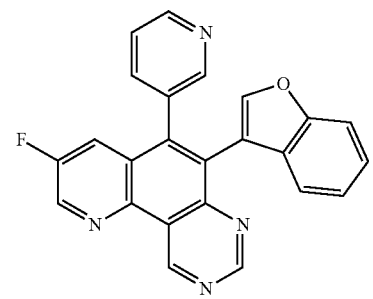

21
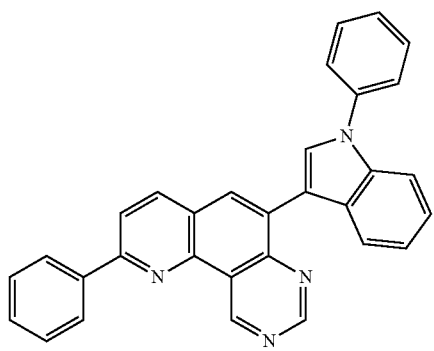

22
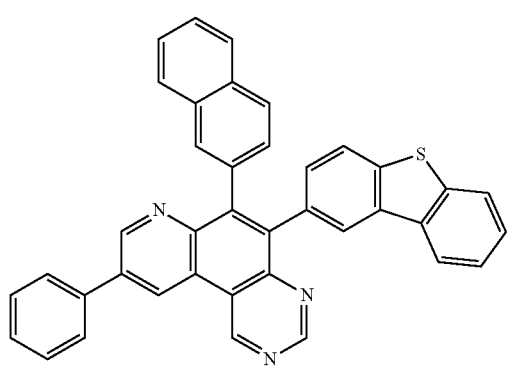

23
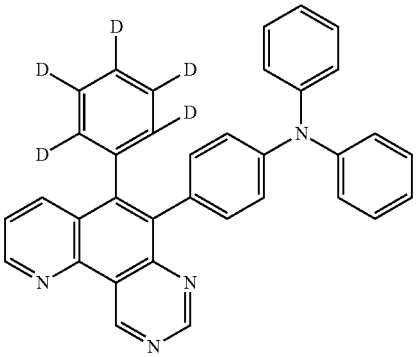

24
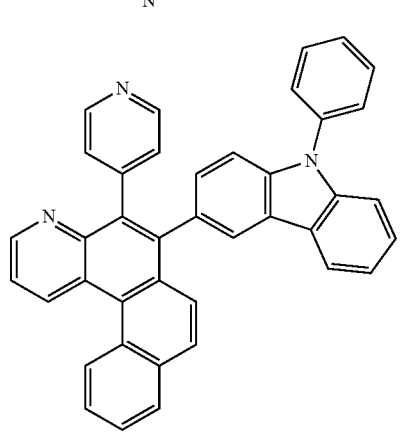

25
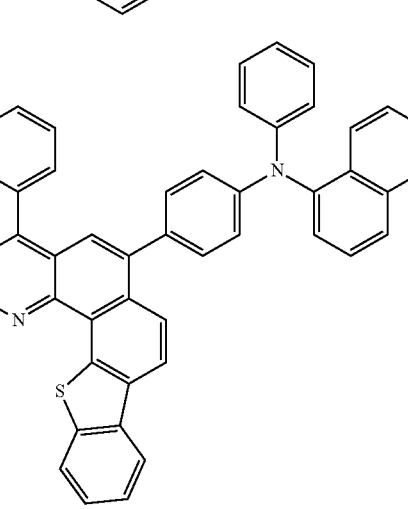

17. An organic light-emitting diode comprising: a first electrode; a second electrode facing the first electrode; and an organic layer between the first electrode and the second electrode, wherein the organic layer comprises at least one condensed-cyclic compound according to claim 1.

18. The organic light-emitting diode of claim 17, wherein the organic layer comprises at least one of a hole injection layer, a hole transport layer, a functional layer having both hole injecting and hole transporting capabilities, a buffer layer, an electron blocking layer, an emission layer, a hole blocking layer, an electron transport layer, an electron injection layer, or a functional layer having both electron injecting and electron transporting capabilities.

19. The organic light-emitting diode of claim 17, wherein the organic layer comprises an emission layer that comprises the condensed-cyclic compound.

20. The organic light-emitting diode of claim 19, wherein the condensed-cyclic compound contained in the emission layer is a fluorescent dopant.

21. The organic light-emitting diode of claim 20, wherein the condensed-cyclic compound contained in the emission layer is represented by Formula 1D or 1E:

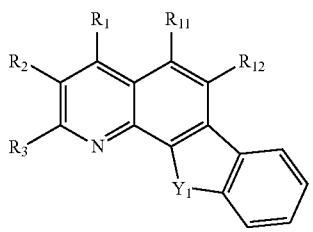

Formula 1D

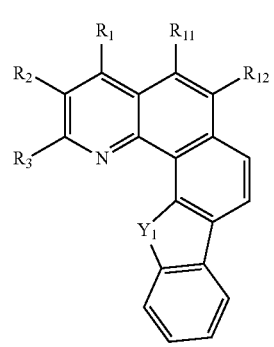

Formula 1E wherein:

$Y_1$ is S or O;

each of $R_1$ to $R_3$ is independently a hydrogen atom, a deuterium atom, a halogen atom, a cyano group, a methyl group, an ethyl group, a propyl group, a butyl group, a pentyl group, a methoxy group, an ethoxy group, a propoxy group, a butoxy group, a pentoxy group, a phenyl group, or a naphthyl group;

$R_{11}$ and $R_{12}$ are each independently selected from a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, or a group represented by one of Formulae 4-1 through 4-49; and at least one of $R_{11}$ or $R_{12}$ is a group represented by one of Formulae 4-1 through 4-49:

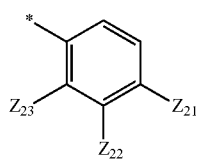

Formula 4-1

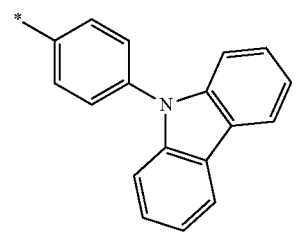

Formula 4-2

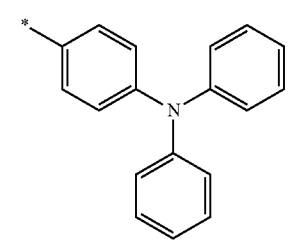

Formula 4-3

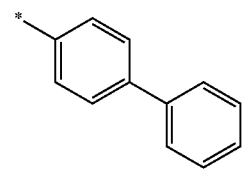

Formula 4-4

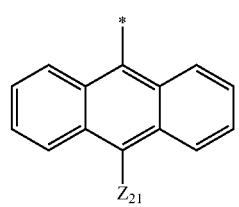

Formula 4-5

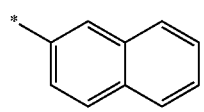

Formula 4-6

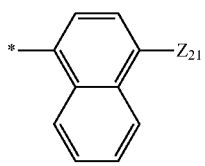

Formula 4-7

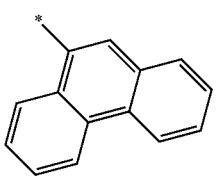

Formula 4-8

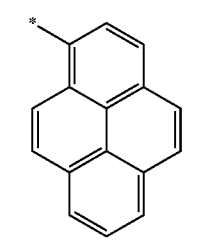

Formula 4-9

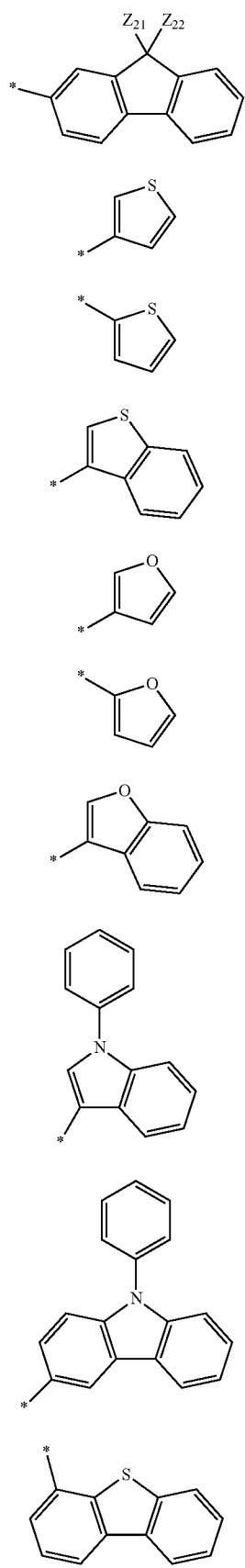
Formula 4-10
Formula 4-11
Formula 4-12
Formula 4-13
Formula 4-14
Formula 4-15
Formula 4-16
Formula 4-17
Formula 4-18
Formula 4-19
Formula 4-20
Formula 4-21
Formula 4-22
Formula 4-23
Formula 4-24
Formula 4-25
Formula 4-26
Formula 4-27

Formula 4-28

Formula 4-29

Formula 4-30

Formula 4-31

Formula 4-32

Formula 4-33

Formula 4-34

Formula 4-35

Formula 4-36

Formula 4-37

Formula 4-38

Formula 4-39

Formula 4-40

Formula 4-41

Formula 4-42

Formula 4-43

Formula 4-44

133

-continued

Formula 4-45

Formula 4-46

Formula 4-47

Formula 4-48

Formula 4-49 wherein each of $Z_{21}$ through $Z_{23}$ is independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, a propyl group, a butyl group, a pentyl group, a methoxy group, an ethoxy group, a propoxy group, a butoxy group, or a pentoxy group; or a methyl group, an ethyl group, a propyl group, a butyl group, a pentyl group, a methoxy group, an ethoxy group, a propoxy group, a butoxy group, or a pentoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, or a phosphoric acid group or a salt thereof.

134

22. The organic light-emitting diode of claim 20, wherein the emission layer further comprises at least one anthracene-based compound represented by Formulae 400 or 401:

Formula 400

$Ar_{114}$—$(Ar_{112})_h$—[anthracene with $(Ar_{115})_i$ and $(Ar_{116})_j$]—$(Ar_{111})_g$—$Ar_{113}$ Formula 401

[structure with $Ar_{122}$, $Ar_{126}$, $Ar_{127}$, $(Ar_{125})_k$, $(Ar_{124})_l$, $Ar_{123}$]

wherein:

each of $Ar_{111}$ and $Ar_{112}$ is independently a substituted or unsubstituted $C_6$-$C_{60}$ arylene group;

each of $Ar_{113}$ through $Ar_{116}$ and $Ar_{122}$ through $Ar_{125}$ is independently a substituted or unsubstituted $C_1$-$C_{10}$ alkyl group or a substituted or unsubstituted $C_6$-$C_{60}$ aryl group;

each of $Ar_{126}$ and $Ar_{127}$ is independently a $C_1$-$C_{10}$ alkyl group; and each of g, h, i, j, k, and l is independently an integer from 0 to 4.

23. The organic light-emitting diode of claim 22, wherein each of $Ar_{111}$ and $Ar_{112}$ is independently a phenylene group, a naphthalene group, a phenanthrenylene group, or a pyrenylene group; or a phenylene group, a naphthalene group, a phenathrenylene group, a fluorenylene group, or a pyrenylene group substituted with at least one of a phenyl group, a naphthyl group, or an anthryl group, each of $Ar_{113}$ through $Ar_{116}$ and $Ar_{122}$ through $Ar_{125}$ is independently selected from a $C_1$-$C_{10}$ alkyl group substituted with at least one of a phenyl group, a naphthyl group, or an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, or a fluorenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, a fluorenyl group, or

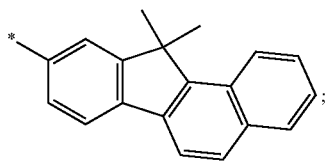 [SMILES: *c1ccc2c(c1)C(C)(C)c1c-2ccc2ccccc12]

each of $Ar_{126}$ and $Ar_{127}$ is independently a methyl group, an ethyl group, or a propyl group; and each of g, h, i, j, k, and l is independently 0, 1 or 2.

24. The organic light-emitting diode of claim 20, wherein the emission layer emits blue light.

25. The organic light-emitting diode of claim 19, wherein the condensed-cyclic compound contained in the emission layer is a phosphorescent host.

26. An organic light-emitting diode comprising: a first electrode; a second electrode facing the first electrode; and an organic layer between the first electrode and the second electrode, wherein the organic layer comprises at least one condensed-cyclic compound according to claim 7, wherein the organic layer comprises an emission layer and the emission layer comprises at least one of the at least one condensed-cyclic compounds, and the at least one condensed-cyclic compound contained in the emission layer is represented by Formula 1C:

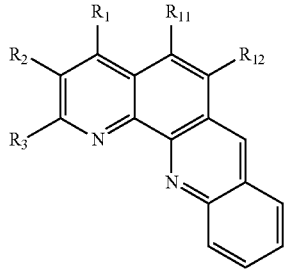

Formula 1C wherein:
each of $R_1$ to $R_3$ is independently a hydrogen atom, a deuterium atom, a halogen atom, a cyano group, a methyl group, an ethyl group, a propyl group, a butyl group, a pentyl group, a methoxy group, an ethoxy group, a propoxy group, a butoxy group, a pentoxy group, a phenyl group, or a naphthyl group, $R_{11}$ and $R_{12}$ are each independently selected from a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid or a salt thereof, a $C_1$-$C_{10}$ alkyl group, a $C_1$-$C_{10}$ alkoxy group, or a group represented by one of Formulae 4-1 through 4-49; and at least one of $R_{11}$ or $R_{12}$ is a group represented by one of Formulae 4-1 through 4-49:

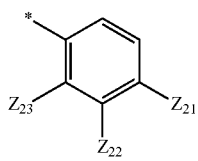

Formula 4-1

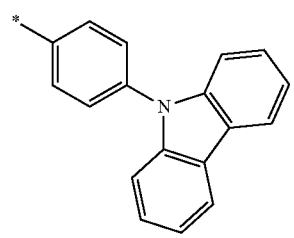

Formula 4-2

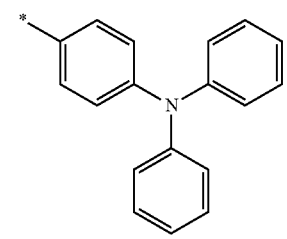

Formula 4-3

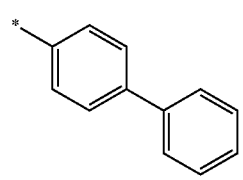

Formula 4-4

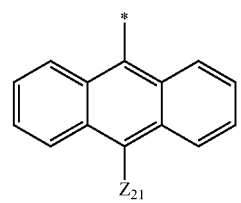

Formula 4-5

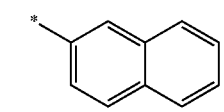

Formula 4-6

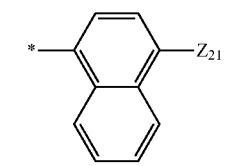

Formula 4-7

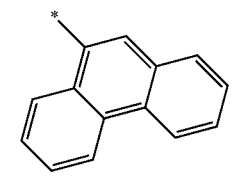

Formula 4-8

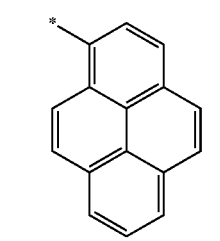

Formula 4-9

Formula 4-10

Formula 4-11

Formula 4-12

Formula 4-13

Formula 4-14

Formula 4-15

Formula 4-16

Formula 4-17

Formula 4-18

Formula 4-19

Formula 4-20

Formula 4-21

Formula 4-22

Formula 4-23

Formula 4-24

Formula 4-25

Formula 4-26

Formula 4-27

Formula 4-28

Formula 4-29

Formula 4-30

Formula 4-31

Formula 4-32

Formula 4-33

Formula 4-34

Formula 4-35

Formula 4-36

Formula 4-37

Formula 4-38

Formula 4-39

Formula 4-40

Formula 4-41

Formula 4-42

Formula 4-43

Formula 4-44

-continued

Formula 4-45

Formula 4-46

Formula 4-47

Formula 4-48

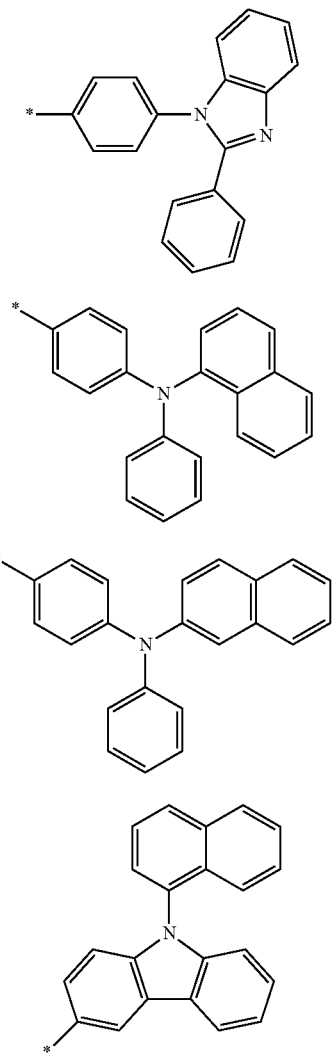

-continued

Formula 4-49

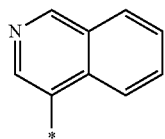

wherein each of $Z_{21}$ through $Z_{23}$ is independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, a propyl group, a butyl group, a pentyl group, a methoxy group, an ethoxy group, a propoxy group, a butoxy group, or a pentoxy group; or a methyl group, an ethyl group, a propyl group, a butyl group, a pentyl group, a methoxy group, an ethoxy group, a propoxy group, a butoxy group, or a pentoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof.

27. The organic light-emitting diode of claim 25, wherein the emission layer emits green light.

28. The organic light-emitting diode of claim 18, wherein the organic layer comprises at least one of a hole injection layer, a hole transport layer, or a functional layer having hole injecting and transporting capabilities, and at least one of the hole injection layer, the hole transport layer, or the functional layer having hole injecting and transporting capabilities comprises a charge-generating material.

29. The organic light-emitting diode of claim 18, wherein the organic layer comprises an electron transport layer that comprises an electron transporting organic compound and a metal complex.

* * * * *